(12) United States Patent  (10) Patent No.: US 8,946,381 B2
Fear et al.  (45) Date of Patent: Feb. 3, 2015

(54) COMPOSITIONS AND USES THEREOF FOR THE TREATMENT OF WOUNDS

(75) Inventors: Mark Fear, Mundaring (AU); Paul Watt, Mount Claremont (AU); Richard Hopkins, North Perth (AU); Nadia Milech, Daglish (AU)

(73) Assignees: Phylogica Limited, Subiaco (AU); The McComb Foundation, Inc., Wembley (AU)

(*) Notice: Subject to any disclaimer, the term of this patent is extended or adjusted under 35 U.S.C. 154(b) by 810 days.

(21) Appl. No.: 12/441,691

(22) PCT Filed: Feb. 6, 2007

(86) PCT No.: PCT/AU2007/000121
§ 371 (c)(1),
(2), (4) Date: Feb. 17, 2010

(87) PCT Pub. No.: WO2008/034162
PCT Pub. Date: Mar. 27, 2008

(65) Prior Publication Data
US 2010/0166835 A1    Jul. 1, 2010

Related U.S. Application Data

(60) Provisional application No. 60/826,208, filed on Sep. 19, 2006.

(51) Int. Cl.
| A61K 38/00 | (2006.01) |
| A61K 38/16 | (2006.01) |
| A61L 15/00 | (2006.01) |
| A61L 15/16 | (2006.01) |
| C07K 14/47 | (2006.01) |

(52) U.S. Cl.
CPC ............. *C07K 14/4703* (2013.01); *A61K 38/00* (2013.01); *C07K 2319/00* (2013.01)
USPC ........ 530/324; 514/18.6; 514/18.9; 514/21.3; 424/445; 424/447

(58) Field of Classification Search
None
See application file for complete search history.

(56) References Cited

U.S. PATENT DOCUMENTS

| 5,516,637 | A |  | 5/1996 | Huang et al. |
| 5,763,239 | A |  | 6/1998 | Short et al. |
| 5,783,431 | A |  | 7/1998 | Peterson et al. |
| 5,821,047 | A |  | 10/1998 | Garrard et al. |
| 5,834,247 | A |  | 11/1998 | Comb et al. |
| 5,843,698 | A |  | 12/1998 | Sorensen |
| 6,074,815 | A |  | 6/2000 | Sorensen |
| 6,083,715 | A |  | 7/2000 | Georgiou et al. |
| 6,150,127 | A |  | 11/2000 | Sorensen |
| 6,174,673 | B1 |  | 1/2001 | Short et al. |
| 6,190,908 | B1 |  | 2/2001 | Kang |
| 6,221,355 | B1 | * | 4/2001 | Dowdy ....................... 424/192.1 |
| 6,225,530 | B1 |  | 5/2001 | Weigel et al. |
| 6,238,884 | B1 |  | 5/2001 | Short et al. |
| 6,297,004 | B1 |  | 10/2001 | Russell et al. |
| 6,316,223 | B1 |  | 11/2001 | Payan et al. |
| 6,319,690 | B1 |  | 11/2001 | Little et al. |
| 6,361,969 | B1 |  | 3/2002 | Galeotti |
| 6,436,694 | B1 |  | 8/2002 | Tally et al. |
| 6,475,726 | B1 |  | 11/2002 | Tally et al. |
| 6,521,425 | B2 |  | 2/2003 | Perler et al. |
| 6,560,542 | B1 |  | 5/2003 | Mandell et al. |
| 6,579,675 | B2 |  | 6/2003 | Kamb |
| 6,583,108 | B1 |  | 6/2003 | Tamburini et al. |
| 6,583,275 | B1 |  | 6/2003 | Doucette-Stamm et al. |
| 6,610,820 | B1 | * | 8/2003 | Bonny ........................... 530/300 |
| 6,720,139 | B1 |  | 4/2004 | Zyskind et al. |
| 6,720,413 | B1 |  | 4/2004 | Schweinfest et al. |
| 6,846,625 | B1 |  | 1/2005 | Tally et al. |
| 6,962,904 | B1 | * | 11/2005 | Sandberg et al. ............. 514/18.8 |
| 7,041,868 | B2 | * | 5/2006 | Greene et al. .................... 602/48 |
| 7,053,046 | B2 | * | 5/2006 | McGrath ....................... 514/21.6 |
| 7,117,096 | B2 |  | 10/2006 | Luo et al. |
| 7,303,885 | B1 | * | 12/2007 | Brunner et al. ................. 435/7.1 |
| 2002/0150906 | A1 |  | 10/2002 | Debe |
| 2002/0155564 | A1 |  | 10/2002 | Medrano et al. |
| 2002/0164735 | A1 |  | 11/2002 | Olson et al. |
| 2005/0287580 | A1 |  | 12/2005 | Watt et al. |
| 2007/0031832 | A1 | * | 2/2007 | Watt et al. .......................... 435/6 |

(Continued)

FOREIGN PATENT DOCUMENTS

| AU | 1860395 | 7/1995 |
| AU | 4808597 | 5/1998 |

(Continued)

OTHER PUBLICATIONS

Schuetz et al . 2005. Expert Opin Drug Deliv. 2:533-548.*
Hess et al. 2004. J. Cell Sci 117:5695-5973.*
Vives et al. 1997. J. Biol Chem 272:16010-16017.*
Bennett, B.L., "c-Jun N-Terminal Kinase-Dependent Mechanisms in Respiratory Disease," Eur. Respir. Journal, 2006, pp. 651-661, vol. 28.
Florin, I. et al., "Identification of Novel AP-1 Target Genes in Fibroblasts Regulated During Cutaneous Wound Healing," Oncogene, 2004, pp. 7005-7017, vol. 23, No. 42.
Nguyen, C. et al., "Chemogenomic Identification of Ref-1/AP-1 as a Therapeutic Target for Asthma," Proc. Nat. Acad. Sci., Feb. 4, 2003, pp. 1169-1173, vol. 100, No. 3.
PCT International Search Report, PCT Application No. PCT/AU2007/000092, Apr. 2, 2007, 3 pages.
PCT International Preliminary Examination Report, PCT Application No. PCT/AU2007/000092, Mar. 24, 2009, 7 pages.
PCT International Search Report and Written Opinion, PCT Application No. PCT/AU2007/000121, Apr. 5, 2007, 8 pages.

(Continued)

*Primary Examiner* — Shulamith H Shafer
(74) *Attorney, Agent, or Firm* — Fenwick & West LLP

(57) ABSTRACT

The present invention provides a topical composition comprising (i) an amount of an AP-1 signaling inhibitor sufficient to reduce, delay or prevent apoptosis and/or necrosis induced by dermal wounding and/or to induce and/or enhance proliferation of a cell; and (ii) a suitable carrier or excipient e.g., a topical carrier or excipient or other carrier or excipient for dermal application. For example, the AP-1 signaling inhibitor is a peptide analog comprising the sequence set forth in SEQ ID NO: 104. The present invention also provides a method of treating a dermal wound comprising topically administering said topical composition to a subject suffering from a dermal wound.

21 Claims, 25 Drawing Sheets

(56) References Cited

U.S. PATENT DOCUMENTS

| | | |
|---|---|---|
| 2007/0060514 A1 | 3/2007 | Bonny |
| 2009/0170722 A1 | 7/2009 | Watt et al. |
| 2010/0029552 A1* | 2/2010 | Watt et al. .............. 514/12 |

FOREIGN PATENT DOCUMENTS

| | | |
|---|---|---|
| AU | 2258799 | 7/1999 |
| AU | 756617 B2 | 1/2003 |
| AU | 771534 B2 | 3/2004 |
| CN | 1629637 | 6/2005 |
| EP | 1277835 A1 | 1/2003 |
| EP | 1776958 A2 | 4/2007 |
| EP | 1811033 A1 | 7/2007 |
| WO | WO 95/17412 | 6/1995 |
| WO | WO 98/15172 | 4/1998 |
| WO | WO 98/16835 | 4/1998 |
| WO | WO 99/35282 | 7/1999 |
| WO | WO 00/68373 | 11/2000 |
| WO | WO 00/76308 | 12/2000 |
| WO | WO 01/11086 | 2/2001 |
| WO | WO 01/32156 A2 | 5/2001 |
| WO | WO 03/012055 | 2/2003 |
| WO | WO 03/040168 | 5/2003 |
| WO | WO 03/046147 | 6/2003 |
| WO | WO 03/076621 | 9/2003 |
| WO | WO 2004/074479 | 9/2004 |
| WO | WO 2004/074479 A1 | 9/2004 |
| WO | WO 2006/017913 | 2/2006 |
| WO | WO 2006/017913 A1 | 2/2006 |
| WO | WO 2007/031098 A1 | 3/2007 |
| WO | WO 2008/034161 A1 | 3/2008 |
| WO | WO 2008/034162 A1 | 3/2008 |
| WO | WO 2008/154700 A1 | 12/2008 |

OTHER PUBLICATIONS

PCT International Preliminary Examination Report, PCT Application No. PCT/AU2007/000121, Mar. 24, 2009, 4 pages.

PCT International Search Report and Written Opinion, PCT Application No. PCT/AU2008/000903, Oct. 15, 2008, 13 pages.

PCT International Preliminary Report on Patentability, PCT Application No. PCT/AU2008/000903, Dec. 22, 2009, 7 pages.

RefSeq Accession No. XP_975325.1, NCBI Sequence Viewer v2.0, 1 page, [Online] [Retrieved on May 3, 2007].

RefSeq Accession No. YP_284595.1, NCBI Sequence Viewer v2.0, 2 pages, [Online] [Retrieved on May 3, 2007].

Yates, S. et al."Transcription Factor Activation in Response to Cutaneous Injury: Role of AP-1 in Reepithelialization," Wound Repair Regeneration, 2002, pp. 5-15, vol. 10, No. 1.

Hooper, R.G. et al., "Established ARDS Treated with a Sustained Course of Adrenocortical Steroids," Chest, 1990, pp. 138-143, vol. 97.

"Acute Respiratory Distress Syndrome Treatment & Management," Medscape Reference, WebMD LLC, 1994-2013, 3 pages [Online] [Retrieved on Feb. 21, 2013] Retrieved from the Internet<URL:http://emedicine.medscape.com/article/165139-treatment>.

"Acute Respiratory Distress Syndrome (ARDS)—IHACares," IHA, 2 pages, [Online] [Retrieved on Feb. 21, 2013] Retrieved from the Internet<URL:http://www.ihacares.com/index.cfm/HealthAdvisors/AdultHealthAdvisor/crs-aha-aha-acute.respiratory.distress.syndrome/>.

Alekshun, M.N., "Beyond Comparison—Antibodies From Genome Data?" Nature Biotechnology, Dec. 2001, pp. 1124-1125, vol. 19.

Amann, E. et al., "ATG Vectors for Regulated High-Level Expression of Cloned Genes in Escherichia coli," Gene, 1985, pp. 183-190, vol. 40.

Amstutz, P. et al., "In vitro Display Technologies: Novel Developments and Applications," Current Opinion in Biotechnology, 2001, pp. 400-405, vol. 12.

Andre, S. et al. (Jan. 17, 2005). "Identification of Peptide Ligands for Malignancy- and Growth-Related Galectins Using Random Phage-Display and Designed Combinatorial Peptide Libraries," Bioorganic & Medicinal Chemistry 13(2):563-573.

Angrist, M. (1998) "Less is More: Compact Genomes Pay Dividends," Genome Research 8:683-685.

Arenkov, P. et al (2000). "Protein Microchips: Use for Immunoassay and Enzymatic Reactions," Analytical Biochemistry 278:123-131.

Balaban, N. et al. (Apr. 17, 1998). "Autoinducer of Virulence as a Target for Vaccine and Therapy Against Staphylococcus aureus," Science 280:438-440.

Basbous, J. et al. (Oct. 31, 2003). "The HBZ Factor of Human T-cell Leukemia Virus Type 1 Dimerizes with Transcription Factors JunB and c-Jun Modulates Their Transcriptional Activity," The Journal of Biological Chemistry 278 (44): 43620-43627.

Baud, F. et al. (Oct. 26, 1999). "Measures of Residue Density in Protein Structures," Proc. Natl. Acad. Sci. USA 96:12494-12499.

Behrens, A. et al. (Mar. 1999). "Amino-Terminal Phosphorylation of c-Jun Regulates Stress-Induced Apoptosis and Cellular Proliferation," Nature Genetics 21:326-329.

Berzofsky, J.A. (Sep. 6, 1985). "Intrinsic and Extrinsic Factors in Protein Antigenic Structure," Science 229(4717):932-940.

Blum, J.H. et al. (Feb. 29, 2000), "Isolation of Peptide Aptamers That Inhibit Intracellular Processes," Proc. Natl. Acad. Sci. USA 97(5):2241-2246.

Bonaldo, M. et al. (1997). "Normalisation and Subtraction: Two Approaches to Facilitate Gene Discovery," Genome Res. 6:791-806.

Bremnes, T. et al. (1998). "Selection of Phage Displayed Peptides From a Random 10-mer Library Recognising a Peptide Target," Immunotechnology 4:21-28.

Britten, R.J. et al. (Aug. 9, 1968). "Repeated Sequences in DNA," Science 161(3841):529-540.

Brodin, N.T. et al (May 15, 1990). "Rat Monoclonal Antibodies Produced Against Rat Colorectal Adenocarcinomas Define Tumor- and Colon-Associated, Auto-Immunogenic Antigens," Int. J. Cancer 45(5):902-910.

Burioni, R. et al. (1998). "A New Subtraction Technique for Molecular Cloning of Rare Antiviral Antibody Specificities From Phage Display Libraries," Res. Virol. 149:327-330.

Campbell, A.P. et al. (1997). "Solution Secondary Structure of a Bacterially Expressed Peptide from the Receptor Binding Domain of Pseudomonas aeruginosa Pili Strain PAK: A Heteronuclear Multidimensional NMR Study," Biochem. 36(42):12791-12801.

Caponigro, G. et al. (Jun. 1998). "Transdominant Genetic Analysis of a Growth Control Pathway," Proc. Natl. Acad. Sci USA 95:7508-7513.

Chapman, M.D, et al. (Nov. 1984). "Recognition of two Dermatophagoides pteronyssinus-specific Epitopes on Antigen P1 by using Monoclonal Antibodies: Binding to Each Epitope can be Inhibited by Serum from Dust Mite-Allergic Patients," J Immunol 133(5):2488-2495.

Chevray, P.M. et al. (Jul. 1992). "Protein Interaction Cloning in Yeast: Identification of Mammalian Proteins that React with the Leucine Zipper of Jun," Proc. Natl. Acad. Sci. USA 89: 5789-5793.

Choi, Y. et al. (Mar. 2003). "Identification of Bioactive Moleculesby Adipogenesis Profiling of Organic Compounds," FASEB Meeting on Experimental Biology: Translating the Genome, San Diego, CA, Apr. 11-15 2003, 17(4-5):A605, Abstract No. 377.23, one page.

Colas et al. (Apr. 11, 1996). "Genetic Selection of Peptide Aptamers That Recognize and Inhibit Cyclin-Dependent Kinase 2," Nature 380:548-550.

Colbère-Garapin et al. (1981). "A New Dominant Hybrid Selective Marker for Higher Eukaryotic Cells," J. Mol. Biol. 150:1-14.

Cordwell, S.J. (1999). "Microbial Genomes and 'Missing' Enzymes: Redefining Biochemical Pathways," Arch. Microbiol. 172:269-279.

Davies, J.M. et al. (Jun. 2000). "Use of Phage Display Technology to Investigate Allergen-Antibody Interactions," J. Allergy Clin. Immunol. 105(6):1085-1092 2000.

De Soultrait et al. (2002). "A Novel Short Peptide is a Specific Inhibitor of the Human Immunodeficiency Virus Type 1 Integrase," J. Mol. Biol. 318:45-58.

Dent et al. (1999). "The Genetics of Ivermectin Resistance in Caenorhabditis elegans," Proc. Natl. Acad. Sci. USA 97:2674-2679.

(56) References Cited

OTHER PUBLICATIONS

DeRossi et al. (1994). "The Third Helix of the Antennapedia Homeodomain Translocates Through Biological Membranes," J. Biol. Chem. 269:10444-10450.
Deveraeux et al. (1984). "A Comprehensive Set of Sequence Analysis Programs for the VAX," Nucl. Acids Res. 12:387-395.
DeVito et al. (2002). "An Array of Target-Specific Screening Strains for Antibacterial Discovert," Nature Biotechnology 20:478-483.
Erdos, G. et al. (2006). "Construction and Characterization of a Highly Redundant *Pseudonomas aeruginosa* Genomic Library Prepared From 12 Clinical Isolates: Application to Studies of Gene Distribution Among Populations," Intl. Journal of Pediatric Otorhinolaryngology 70:1891-1900.
Estus, S. et al. (Dec. 1994). "Altered Gene Expression in Neurons During Programmed Cell Death: Identification of c-Jun as Necessary for Neuronal Apoptosis," The Journal of Cell Biology 127(6):1717-1727.
Faber et al. (1999). "Polyglutamine-Mediated Dysfunction and Apoptotic Death of a *Caenorhabditis elegans* Sensory Neuron," Proc. Natl. Acad. Sci. 96:179-184.
Fabret et al. (2000). "Efficient Gene Targeted Random Mutagenesis in Genetically Stable *Escherichia coli* strains," Nucl. Acids Res. 28:e95.
Fahraeus et al. (1996) "Inhibition of prb Phosphorylation and Cell-Cycle Progression by a 20-Residue Peptide Derived From p16 CDKN2/INK4An," Curr. Biol. 6(1):84-91.
Fang, Y. et al. (2002). "G-Protein-Coupled Receptor Microarrays," ChemBioChem., 3: 987-991.
Fehrsen et al. (1999). "Cross-Reactive Epitope Mimics in a Fragmented-Genome Phage Display Library Derived from the Rickettsia, Cowdria ruminantium," Immunotechnology 4:175-184.
Filipe, S.R. (2001). "The Role of murMN Operon in Penicillin Resistance and Antibiotic Tolerance of *Streptococcus pneumoniae*," Microbial Drug Resistance 7(4):303-316.
Fitzgerald (2000). "In vitro Display Technologies—New Tools for Drug Discovery," Drug Discovery Today 5:253-258.
Franzoni et al. (1997). "Structure of the C-Terminal Fragment 300-320 of the Rat Angiotensin II AT 1a Receptor and Its Relevance with Respect to G-Protein-Coupling," J. Biol. Chem. 272:9734-9741.
Furmonaviciene, R. et al. (1999). "The Use of Phage-Peptide Libraries to Define the Epitope Specificity of a Mouse Monoclonal Anti-Der p 1 Response," Clin. Exp. Allergy 29:1563-1571.
Futch, W.S. Jr. et al. (Mar. 15, 2003). "Dissection of Macrophage Tumoricidal and Protozoacidal Activities Using T-Cell Hybridomas and Recombinant Lymphokines," Infection and Immunity 50(3): 709-715.
Garcia, M. et al. (Mar. 15, 2002). "The Mitochondrial Toxin 3-Nitropropionic Acid Induces Striatal Neurodegeneration via a c-Jun N-Terminal Kinase/c-Jun Module," The Journal of Neuroscience 22(6):2174-2184, J. Neuroscience, 22: 2174-2184.
Gargala, G. et al. (1999). "Enzyme Immunoassay Detection of *Cryptosporidium parvum* Inhibition by Sinefungin in Sporozoite Infected HCT-8 Enterocytic Cells," International Journal of Parasitology 29: 703-709.
Gegg et al. (1997). "Probing Minimal Independent Folding Units in Dihydrofolate Reductase by Molecular Dissection," Protein Sci. 6:1885-1892.
GenBank Accession No. AAH36335 (last updated May 20, 2005), located at <http://www.ncbi.nlm.nih.gov/entrez/viewer.fcgi?db=protein&id=23273658>, last visited Apr. 1, 2008, three pages.
GenBank Accession No. AAN49594 (last updated Feb. 1, 2006), <http://www.ncbi.nlm.nih.gov/entrez/viewer.fcgi?db=protein&d=24196153>, last visited Apr. 1, 2008, two pages.
GenBank Accession No. AAS70149 (last updated Jan. 4, 2006), <http://www.ncbi.nlm.nih.gov/entrez/viewer.fcgi?db=protein&d=45600665>, last visited Apr. 1, 2008, two pages.
GenBank Accession No. AAV59791 (last updated Jan. 21, 2005), <http://www.ncbi.nlm.nih.gov/entrez/viewer.fcgi?db=protein&d=55736149>, last visited Apr. 1, 2008, three pages.
GenBank Accession No. CAD25932 (last updated Apr. 16, 2005), <http://www.ncbi.nlm.nih.gov/entrez/viewer.fcgi?db=protein&d=19069547>, last visited Apr. 1, 2008, two pages.
GenBank Accession No. CAH10659 (last updated Sep. 22, 2004), <http://www.ncbi.nlm.nih.gov/entrez/viewer.fcgi?db=protein&d=50949409>, last visited Apr. 1, 2008, two pages.
Getzoff et al. (1987). "Mechanisms of Antibody Binding to a Protein," Science 235:1191-1196.
Granger-Schnarr, M. et al. (May 1992). "Transformation and Transactivation Suppressor Activity of the c-Jun Leucine Zipper Fused to a Bacterial Repressor," Proc. Natl. Acad. Sci. USA 89:4236-4239.
Greene et al. (1992). "IgE Binding Structures of the Major House Dust Mite Allergen DER P 1," Mol. Immunology 29:257-262.
Haley, K.J. et al. (Aug. 1998). "Tumor Necrosis Factor Induces Neuroendocrine Differentiation in Small Cell Lung Cancer Cell Lines," American Journal of Physiology 275(2 pt 1):L311-L321.
Halstead, J.R. et al. (1999). "A Family 26 Mannanase Produced by *Clostridium thermocellum* as a Component of the Cellulosome Contains a Domain Which is Conserved in Mannanases from Anaerobic Fungi," Microbiology 145:3101-3108.
Hegde S. S. et al. (Mar. 9, 2001). "FemABX Family Members Are Novel Nonribosomal Peptidyltransferases and Important Pathogen-SpecificDrug Targets," The Journal of Biological Chemistry 276(10):6998-7003.
Hengeveld et al.(2002). "Functional and Structural Characterization of a Synthetic Peptide Representing the N-Terminal Domain of Prokaryotic Pyruvate Dehydrogenase," Biochem. 41:7490-7500.
Heymann et al. (1989). "Antigenic and Structural Analysis of Group II Allergens (Der f II and Der p II) From House Dust Mites (*Dermatophagoides* spp.)" J. Allergy Clin. Immunol 83:1055-1067.
Hofmann et al. (1996). "Rapid Retroviral Delivery of Tetracycline-Inducible Genes in a Single Autoregulatory Cassette," Proc. Natl. Acad. Sci. 93:5185-5190.
Hoogenboom et al. (1991). "Multi-Subunit Proteins on the Surface of Filamentous Phage: Methodologies for Displaying Antibody (Fab) Heavy and Light Chaims," Nucleic acids Res. 19:4133-4137.
Horng et al. (2002). "Characterization of Large Peptide Fragments Derived from the N-Terminal Domain of the Ribosomal Protein L9: Definition of the Minimum Folding Motif and Characterization of Local Electrostatic Interactions," Biochem. 41:13360-13369.
Hosen, N. et al. (2004). "Identification of a Gene Element Essential for Leukemia-Specific Expression of Transgenes," Leukemia 18:415-419.
Houshmand et al. (1999). "Use of Bacteriophage T7 Displayed Peptides for Determination of Monoclonal Antibody Specificity and Biosensor Analysis of the Binding Reaction," Anal. Biochem. 268:363-370.
Humphrey et al. (1997). "Chemical Synthesis of Natural Product Peptides; Coupling Methods for the Incorporation of Noncoded Amino Acids into Peptides," Chem. Rev. 97:2243-2266.
International Preliminary Report on Patentability mailed on Feb. 20, 2007, for PCT Application No. PCT/AU2005/001255, filed Aug. 22, 2005, ten pages.
International Search Report mailed on Aug. 16, 2005, for PCT Application No. PCT/AU2005/000801, filed Jun. 3, 2005, eight pages.
International Search Report mailed on Nov. 17, 2005, for PCT Application No. PCT/AU2005/001255, filed Aug. 22, 2005, six pages.
Irbäck, et al. (1996). "Evidence for Nonrandom Hydrophobicity Structures in Protein Chains," Proc. Natl. Acad. Sci. 93:9533-9538.
Kabouridis, P. S. (Nov. 2003). "Biological Applications of Protein Transduction Technology," Trends in Biotechnology 21(11): 498-503.
Kinzler et al. (1989). "Whole Genome PCR: Application to the Identification of Sequences Bound by Gene Regulatory Proteins," Nucleic Acids Res. 17:3645-3653.
Kolonin et al. (Nov. 1998). "Targeting Cyclin-Dependent Kinases in Drosophilia with Peptide Aptamers," Proc. Natl, Acad. Sci. 95:14266-14271.
Koncz et al. (1987). "Expression and Assmebly of Functional Bacterial Luciferase in Plants," Proc. Natl. Acad. Sci. 84:131-135.
Koo, J.H. et al. (Mar. 8, 2001). "Purification and Characterization of Bex, an OMP Parter," Annual Meeting of the Federation of American

(56) References Cited

OTHER PUBLICATIONS

Societies for Experimental Biology on Experimental Biology Orlando, FL, Mar. 31-Apr. 4, 2001, 15(5):A894, Abstract No. 695.14, one page.

Kopczynski et al. (1998). "A High Throughput Screen to Identify Secreted and Transmembrane Proteins Involved in Drosophilia embryogenesis," Proc. Natl. Acad. Sci. 95:9973-9978.

Lambros, C. et al. (Jun. 1979). "Synchronization of *Plasmodium falciparum* Erythrocytic Stages in Culture," J. Parasitology 65(3):418-420.

Layne, M.D. et al. (Jun. 18, 1998). "Aortic Carboxypeptidase-Like Protein, Novel Protein with Discoidin and Carboxypeptidase-Like Domains, Is Up-Regulated During Vascular Smooth Muscle Cell Differentiation ," The Journal of Biological Chemistry 273(25):15654-15660.

Lee, et al (1994). "Structure-Antigenicity Relationship of Peptides from the Pre-s2 Region of the Hepatitus B Virus Surface Antigen," Biochem Mol Biol Int. 34(1):159-168.

Lee, Y. et al. (2003). "ProteoChip: A Highly Sensitive Protein Microarray Prepared by a Novel Method of Protein Immobilization for Application of Protein-Protein Interaction Studies," Proteomics, 3:2289-2304.

Leitner, A. et al. (1998) "A Mimotope Defined by Phage Display Inhibits IgE Binding to the Plant Panallergen Profiling," Eur. J. Immunol 28:2921-2927.

Lesley et al. (1991). "Use of in vitro Protein Syntheses from Polymerase Chain Reaction-Generated Templates to Study Interaction of *Escherichia coli* Transcription Factors with Core RNA Polymerase and for Epitope Mapping of Monoclonal Antibodies," J. Biol. Chem. 266:2632-2638.

Lessel, et al. (1997). "Creation and characterization of a new, non-redundant fragment data bank," Protein Engineering 10(6):659-664.

Lind, et al. (1988). "The Binding of Mouse Hybridoma and Human IgE Antibodies to the Major Fecal Allergen, Der p 1, of *Dermatophagoides pteronyssinus,*" J. Immunol 40:4256-4262.

Maidhof, H. et al. (Jun. 1991). "femA, Which Encodes a Factor Essential for Expression of Methicillin Resistance, Affects Glycine Content of Peptidoglycan in Methicillin-Resistant and Methicillin-Susceptible *Staphylococcus aureus* Strains," Journal of Bacteriology 173(11):3507-3513.

Marcello et al. (Sep. 1994). "Specific Inhibition of Herpes Virus Replication by Receptor-Mediated Entry of an Antiviral Peptide Linked to *Escherichia coli* Enterotoxin B Subunit," Proc. Natl. Acad. Sci. 91:8994-8998.

Marsh et al. (2000). "Expanded Polyglutamine Peptides Alone are Intrinsically Cytotoxic and Cause Neurodegeneration in Drosophilia," Hum. Mol. Genet. 9:13-25.

Mazmanian, S. K. et al. (Jul. 30, 1999). "*Staphylococcus aureus* Sortase, an Enzyme that Anchors Surface Proteins to the Cell Wall," Science, 285:760-763.

Mazmanian, S. K. et al. (May 9, 2000) "*Staphylococcus aureus* Sortase Mutants Defective in the Display of Surface Proteins and in the Pathogenesis of Animal Infections,"Proc. Natl. Acad. Sci. 97(10):5510-5515.

McCafferty et al. (1990). "Phage Antibodies: Filamentous Phage Displaying Antibody Variable Domains," Nature 348:552-554.

McConnell et al. (1994). "Constrained Peptide Libraries as a Tool for Finding Mimotopes," Gene 151:115-118.

McElveen, J.E. (1998). "Primary Sequence and Molecular Model of the Variable Region of a Mouse Monoclonal Anti-Der p 1 Antibody Showing a Similar Epitope Specificity as Human IgE," Clinical and Experimental Allergy 28:1427-1434.

Mennuni et al. (1997). "Identification of a Novel Type 1 Diabetes-Specific Epitope by Screening Phage Libraries with Sera from Pre-Diabetic Patients," J. Mol. Biol. 268:599-606.

Michiels, F. et al. (Nov. 2002). "Arrayed Adenoviral Expression Libraries for Functional Screening," Nature Biotechnology 20:1154-1157.

Miller, V.L. et al. (Sep. 2001). "Identification of Regions of All Required for the Invasion and Serum Resistance Phenotypes," Molecular Microbiology 41(5): 1053-1062.

Morris et al. (2000). "Translocating Peptides and Proteins and Their Use for Genen Delivery," Curr. Opinion Biotech. 11:461-466.

Morris et al. (2001). "A Peptide Carrier for the Delivery of Biologically Active Proteins into Mammalian Cells," Nature Biotech. 19:1173-1176.

Mulligan et al. (1981). "Selection for Animal Cells that Express the *Escherichia coli* Gene Coding for Xanthine-Guanine Phosphoribosyltransferase," Proc. Natl. Acad. Sci. USA 78:2072-2076.

Nedelkov, D. et al. (2001). "Analysis of Native Proteins from Biological Fluids by Biomolecular Interaction Analysis Mass Spectrometry (BIA/MS): Exploring the Limit of Detection, Identification of Non-Specific Binding and Detection of Multi-Protein Complexes," Biosensors & Bioelectronics 16:1071-1078.

Needleman et al. (1970). "A General Method Applicable to the Search for Similaritiesin the Amino Acid Sequence of Two Proteins," J. Mol. Biol. 48:443-453.

Neidigh et al. (2002). "Designing a 20-Residue Protein," Nature Structural Biology 9:425-430.

Nelson , K.E. et al. (Oct. 2000). "Status of Genome Projects for Nonpathogenic Bacteria and Archaea," Nature Biotechnology 18:1049-1054.

Nelson R.W. et al. (2000). "Biosensor Chip Mass Spectrometry: A Chip-Based Proteomics Approach," Electrophoresis 21: 1155-1163.

Nelson, R.W. et al. (1999). "BIA/MS of Epitope-Tagged Peptides Directly from *E.coli* Lysate: Multiplex Detection and Protein Identification at Low-Fermtomole to Subfemtomole Levels," Anal. Chem. 71:2858-2865.

Nemoto N. et al. (1999). "Fluorescence Labeling of the C-Terminus of Proteins with a Puromycin Analogue in Cell-Free Translation Systems," FEBS Letters 462:43-46.

Ness et al. (2002). "Synthetic Shuffling Expands Functional Protein Diversity by Allowing Amino Acids to Recombine Independently," Nature Biotechnology 20:1251-1255.

Norman et al. (1999). "Genetic Selection of Peptide Inhibitors of Biological Pathways," Science 285:591-595.

Oefner, P.J. et al. (1996). "Efficient Random Subcloning of DNA Sheared in a Recirculating Point-Sink Flow System," Nucleic Acids Research 24(20):3879-3886.

O'Hare et al. (1981). "Transformation of Mouse Fibroblasts to Methotrexate Resistance by a Recombinant Plasmid Expressing a Prokaryotic Dihydrofolate Reductase," Proc. Natl. Acad. Sci. USA 78:1527-1531.

Palzkill et al. (1998). "Mapping Protein-Ligand Interactions Using Whole Genome Phage Display Libraries," Gene 221:79-83.

Pande et al. (1994). "Nonrandomness in Protein Sequences: Evidence for a Physically Driven Stage of Evolution?" Proc. Natl. Acad. Sci. USA 91:12972-12975.

Pavlickova, P. et al. (2003). "Microarray of Recombinant Antibodies Using a Streptavidin Sensor Surface Self-Assembled onto a Gold Layer," BioTechniques 34(1):124-130.

Phelan et al. (May 1998). "Intercellular Delivery of Functional p53 by the Herpes Virus Protein VP22," Nature Biotechnol. 16:440-443.

Pincus et al. (1998). "Peptides that Mimic the Group B Streptococcal Type III Capsular Polysaccharide Antigen," J. Immunol 160:293-298.

Pini et al. (Aug. 21, 1998). "Design and Use of a Phage Display Library," J. Biol. Chem. 21769-21776.

Postier, B.L. et al. (2003). "The Construction and Use of Bacterial DNA Microarrays Based on an Optimized Two-Stage PCR Strategy," BMC Genomics, vol. 4, 11 pages.

Raivich, G. et al., (2006). "Role of the AP-1 Transcription Factor c-Jun in Developing, Adult and Injured Brain," Progress in Neurobiology. 78:347-363.

Read et al. (2001). "Finding Drug Targbets in Microbial Genomes," Drug Disc. Today 6:887-892.

Richter et al. (2000). "Refolding, Purification, and Characterization of Human Recombinant pde4a Constructs Expressed in *Escherichia coli,*" Protein Expression and Purification 19:375-383.

(56) References Cited

OTHER PUBLICATIONS

Robben et al. (2002). "Selection and Identification of Dense Granule Antigen GRA3 by *Toxoplasma gindii* Whole Genome Phage Display," J. Biol. Chem. 277:17544-17547.

Roberts et al. (1997). "RNA-Peptide Fusions for the in vitro Selection of Peptides and Proteins," Proc. Natl. Acad. Sci. USA 94:12297-12302.

Rogers et al. (1997). "Behavioral and Functional Analysis of Mouse Phenotype: SHIRPA, a Proposed Protocol for Comprehensive Phenotype Assessment," Mamm. Genome 8:711-713.

Rohrer, S. et al. (Aug. 1999). ":The Essential *Staphylococcus aureus* Gene fmhB is Involved in the First Step of Peptidoglycan Pentaglycine Interpeptide Formation," Proc. Natl. Acad. Sci. USA, 96: 9351-9356.

Rosenthal, P. J. et al. (Jul. 1996). "Antimalarial Effects of Vinyl Sulfone Cysteine Proteinase Inhibitors," Antimicrobial Agents and Chemotherapy 40(7): 1600-1603.

Sali, A., et al. (1993). "Comparative Protein Modelling by Satisfaction of Spatial Restraints," J. Mol. Biol. 234, 779-815.

Sambook et al. (1989). Chapters 12.2 in Molecular Cloning: a Laboratory Manual Second Edition. Cold Spring Harbor Laboratory Press, USA.

Santerre et al. (1984). "Expression of Prokaryotic Genees for Hygromycin B and G418 Resistance as Dominant-Selection Markers in Mouse L Cells," Gene 30:147-156.

Satyal et al. (2000). "Polyglutamine Aggregates Alter Protein Folding Homeostatis in *Caenorhabditis elegans*," Proc. Natl. Acad. Sci. USA 97:5750-5755.

Shafikhani et al. (1997). "Generation of Large Libraries of Random Mutants in *Bacillus subtilis* by PCR-based Plasmid Multimerization," BioTechniques 23:304-310.

Shimatake et al. (1981). "Purified λ Regulatory Protein cII Positively Activates Promoters for Lysogenic Development," Nature 292:128-132.

Sieber et al. (2001). "Libraries of Hybrid Proteins from Distantly Related Sequences," Nature Biotechnology 19:456-460.

Soares, M.B. (1997). "Identification and Cloning of Differentially Expressed Genes," Curr. Opinion Biotechnol. 8:542-546.

Stengelin et al. (1988). "Isolation of cDNAs for Two Distinct Human Fc Receptors by Ligand Affinity Cloning," EMBO Journal 7:1053-1059.

Stranden, A.M. et al. (Jan. 1997). "Cell Wall Monoglycine Cross-Bridges and Mathicillin Hypersusceptibility in a femAB Null Mutant of Methicillin-Resistant *Staphylococcus aureus*," Journal of Bacteriology 179(1): 9-16.

Studier et al. (1986). "Use of Bacteriophage T7 RNA Polymerase to Direct Selective High-Level Expression of Cloned Genes," J. Mol. Biol. 189:113-130.

Sugita et al. "Combined Use of Oligonucleotide and Tissue Microarrays Identifies Cancer/Testis Antigens as Biomarkers in Lung Carcinoma," Cancer Res 62:3971-3979, 2002.

Supplementary Partial European Search Report for EP Application No. 04712970.5 mailed Apr. 26, 2006, five pages.

Supplementary Partial European Search Report for EP Application No. 04712970.5 mailed Aug. 3, 2006, seven pages.

Theiss, H.D. et al. (2003). "Enhancement of Gene Transfer With Recombinant Adeno-Associated Virus (rAAV) Vectors into Primary B-Cell Chronic Lymphocytic Leukemia Cells by CpG-oligodeoxynucleotides," Experimental Hematology 31:1223-1229.

Thomas et al. (1990). "Expression in *Escherichia coli* of a High-Molecular-Weight Protective Surface Antigen Found in Nontypeable and Type B *Haemophilus influenzae*," Infect. & Immun. 58:1909-1913.

Thumm, G. et al. (1997). "Studies on Prolysostaphin Processing and Characterization of the Lysostaphin Immunity Factor (Lif) of *Staphylococcus simulans* Biovar Staphylolyticus," Molecular Microbiology 23(6):1251-1265.

Tiozzo, E. et al. (1998). "Wide-Spectrum Antibiotic Activity of Synthetic, Amphipathic Peptides," Biochem. & Biophys. Res. Comm. 249(1):202-206.

Tokmakov et al. (1997) "Inhibition of MAPK Pathway by a Synthetic Peptide Corresponding to the Activation Segment of MAPK," Biochem. Biophys. Res. Comm. 252:214-219.

Tokmakov et al. (1997)."Phosphorylation-Sensitive Secondary Structure in a Synthetic Peptide Corresponding to the Activation Loop of MAP Kinase," Biochem. Biophys. Res. Commun. 236:243-247.

Tortosa, P. et al (Mar. 2000). "Characterisation of ylbF, a New Gene Involved in Competence Development and Sporulation in *Bacillus subtilis*," Molecular Microbiology 35(5) :1110-1119.

Tripet et al. (1997). "Demonstration of Coiled-Coli Interactions Within the Kinesin Neck Region Using Synthetic Peptides," J. Biol. Chem. 272:8946-8956.

Urbanek, M. et al. (Jan. 2003). "Variation in Resistin Gene Promoter Not Associated With Polycystic Ovary Syndrome," Diabetes 52: 214-217.

Valentini, S.R. et al (Feb. 1994). "Glucocorticoid-Regulated Gene in Transformed to Normal Phenotypic Reversion," Brazilian J Med Biol Res 27(2): 541-546.

Van Regenmortel M.H.V. (1989). "Structural and Functional Approaches to the Study of Protein Antigenicity," Immunology Today 10:266-272.

Vidal et al. (1999). "Yeast Forward and Reverse 'n'-hybrid Systems," Nucl. Acids Res. 27:919-929.

Vranken et al. (2002). "Solution Structures of a 30-Residue Amino-Terminal Domain of the Carp Granulin-1 Protein and its Amino-Terminally Truncated 3-30 Subfragment: Implications for the Conformational Stability of the Stack of Two β-Hairpins," Proteins 47:14-24.

Wang et al. (2004). "Predicting protein secondary structure by a support vector machine based on a new coding scheme," Genome Informatics 15(2)181-190.

Wang et al (2005). "PISCES: recent improvements to a PDB sequence culling server," Nucleic Acids Research 33:W94-W98.

Wigler et al. (1980). "Transformation of Mammalian Cells with an Amplifiable Dominant-Acting Gene," Proc. Natl. Acad. Sci. USA 77:3567-3570.

Wittrup, K.D. (2001). "Protein Engineering by Cell-Surface Display," Current Opinion in Biotechnology 12:395-399.

Wong, et al. (1996). "Use of Tagged Random Hexamer Amplification (TRHA) to Clone and Sequence Minute Quantities of DNA-Application to a 180 kb Plasmid Isolated From Sphingomonas F199," Nucleic Acids. Res. 24:3778-3783.

Xu et al. (2001). "Dominant Effector Genetics in Mammalian Cells," Nature Genetics 27:23-29.

Xu et al. (Nov. 1997). "Cells That Register Logical Relationships Among Proteins," Proc. Natl. Acad. Sci. USA 94:12473-12478.

Yang (1999). "Cloning, Expression, and Characterization of a DNA Binding Domain of gpNul, a Phage λ DNA Packaging Protein," Biochem. 38:465-477.

Yang et al. (1998). "A 20-Kilodalton N-Terminal Fragment of the D15 Protein Contains a Protective Epitope(s) Against Haemophilus influenzae Type A and Type B," Infect. And Immun. 66:3349-3354.

Yang et al. (2000). "An Integrated Approach to the Analysis and Modeling of Protein Sequences and Structures. III. A Comparative Study of Sequence Conservation in Protein Structural Families using Multiple Structural Alignments," J. Mol. Biol. 301:691-711.

Yang, P. et al (Dec. 17, 1999). "Direct Activation of the Fission Yeast PAK Shk1 by the Novel SH3 Domain Protein, Skb5," The Journal of Biological Chemistry 274(51): 36052-36057.

Yao, S. et al. (1998). "Uncoiling c-Jun Coiled Coils. Inhibitory Effects of Truncated Fos Peptides on Jun Dimerization and DNA binding In Vitro," Biopolymers 47(4):277-283.

Yao, S.Q. et al. (1997). "Inhibiting Dimerization and DNA Binding of c-Jun," In Peptides: Frontiers of Peptide Science, Proceedings of the 15th Amernican Peptide Symposium, Nashville, TN, Jun. 14-19, 1997, Tam, J.P. et al. eds. Kluwer Academic Publishers, Dordrecht, Netherlands, pp. 751-752.

Yasueda et al. (1996). "Species-Specific Measurement of the Second Group of Dermatophagoides Mite Allergens, Der p 2 and Der f 2, Using a Monoclonal Antibody-based ELISA," Clin. Exp. Allergy. 26:171-177.

(56) References Cited

OTHER PUBLICATIONS

Young, K.H. (1998). "Yeast Two-Hybrid: So Many Interactions, (in) so Little Time," Biology of Reproduction 58:302-311.

Zhang et al. (1992). "Whole Genome Amplification From a Single Cell: Implications for Genetic Analysis," Proc. Natl. Acad. Sci. USA 89:5847-5851.

Zhou, J.M. et al. (2002). "A Novel Strategy by the Action of Ricin that Connects Phenotype and Genotype Without Loss of the Diversity of Libraries," J. Am. Chem. Soc. 124(4):538-543.

Zhou, X-F. et al. (Feb. 1999). "Ligand-Activated Retinoic Acid Receptor Inhibits AP-1 Transactivation by Disrupting c-Jun/c-Fos Dimerization," Mol. Endocrin. 13(2):276-285.

* cited by examiner ated States Patent US 8,946,381 B2

COMPOSITIONS AND USES THEREOF FOR THE TREATMENT OF WOUNDS

RELATED APPLICATION DATA

The present invention application is the National Stage of International Application No. PCT/AU2007/000121 which is herein incorporated in its entirety by reference, and claims the benefit of U.S. Provisional Application No. claims priority from U.S. Patent Application No. 60/826,208 filed Sep. 19, 2006 the contents of which is herein incorporated by reference in its entirety.

FIELD OF THE INVENTION

The present invention relates to topical formulations for the treatment of dermal wounds e.g., involving apoptosis and/or necrosis.

BACKGROUND OF THE INVENTION

General

This specification contains nucleotide and amino acid sequence information prepared using PatentIn Version 3.3, presented herein after the claims. Each nucleotide sequence is identified in the sequence listing by the numeric indicator <210> followed by the sequence identifier (e.g., <210>1, <210>2, <210>3, etc). The length and type of sequence (DNA, protein (PRT), etc), and source organism for each nucleotide sequence, are indicated by information provided in the numeric indicator fields <211>, <212> and <213>, respectively. Nucleotide sequences referred to in the specification are defined by the term "SEQ ID NO:", followed by the sequence identifier (e.g., SEQ ID NO: 1 refers to the sequence in the sequence listing designated as <400>1).

The designation of nucleotide residues referred to herein are those recommended by the IUPAC-IUB Biochemical Nomenclature Commission, wherein A represents Adenine, C represents Cytosine, G represents Guanine, T represents thymine, Y represents a pyrimidine residue, R represents a purine residue, M represents Adenine or Cytosine, K represents Guanine or Thymine, S represents Guanine or Cytosine, W represents Adenine or Thymine, H represents a nucleotide other than Guanine, B represents a nucleotide other than Adenine, V represents a nucleotide other than Thymine, D represents a nucleotide other than Cytosine and N represents any nucleotide residue.

As used herein the term "derived from" shall be taken to indicate that a specified integer may be obtained from a particular source albeit not necessarily directly from that source.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each embodiment described herein is to be applied mutatis mutandis to each and every other embodiment unless specifically stated otherwise.

Each embodiment describing a composition comprising a peptide shall be taken to apply mutatis mutandis to a formulation comprising a retro-inverted form of that peptide, e.g., comprising two or more retro-inverted amino acids. Preferably, the retro-inverted form of the peptide comprises a reversed amino acid sequence and all amino other than glycine are D-amino acids.

Each embodiment herein describing an amount of an AP-1 signaling inhibitor sufficient to reduce, delay or prevent apoptosis shall be taken to apply mutatis mutandis to an amount of an AP-1 signaling inhibitor sufficient to reduce, delay or prevent necrosis.

Each embodiment herein describing an amount of an AP-1 signaling inhibitor sufficient to reduce, delay or prevent apoptosis shall be taken to apply mutatis mutandis to an amount of an AP-1 signaling inhibitor sufficient to reduce, delay or prevent apoptosis and necrosis.

Each embodiment herein describing an amount of an AP-1 signaling inhibitor sufficient to reduce, delay or prevent necrosis shall be taken to apply mutatis mutandis to an amount of an AP-1 signaling inhibitor sufficient to reduce, delay or prevent apoptosis.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific embodiments described herein, which are intended for the purpose of exemplification only. Functionally-equivalent products, compositions and methods are clearly within the scope of the invention, as described herein.

The present invention is performed without undue experimentation using, unless otherwise indicated, conventional techniques of molecular biology, microbiology, virology, recombinant DNA technology, peptide synthesis in solution, solid phase peptide synthesis, and immunology. Such procedures are described, for example, in the following texts that are incorporated by reference:

Sambrook, Fritsch & Maniatis, Molecular Cloning: A Laboratory Manual, Cold Spring Harbor Laboratories, New York, Second Edition (1989), whole of Vols I, II, and III;

DNA Cloning: A Practical Approach, Vols. I and II (D. N. Glover, ed., 1985), IRL Press, Oxford, whole of text;

Oligonucleotide Synthesis: A Practical Approach (M. J. Gait, ed., 1984) IRL Press, Oxford, whole of text, and particularly the papers therein by Gait, pp 1-22; Atkinson et al., pp 35-81; Sproat et al., pp 83-115; and Wu et al., pp 135-151;

Animal Cell Culture: Practical Approach, Third Edition (John R. W. Masters, ed., 2000), ISBN 0199637970, whole of text;

Perbal, B., A Practical Guide to Molecular Cloning (1984);

Methods In Enzymology (S. Colowick and N. Kaplan, eds., Academic Press, Inc.), whole of series;

J. F. Ramalho Ortigão, "The Chemistry of Peptide Synthesis" In: Knowledge database of Access to Virtual Laboratory website (Interactiva, Germany);

Barany, G. and Merrifield, R. B. (1979) in *The Peptides* (Gross, E. and Meienhofer, J. eds.), vol. 2, pp. 1-284, Academic Press, New York.

Bodanszky, M. (1984) *Principles of Peptide Synthesis*, Springer-Verlag, Heidelberg.

Bodanszky, M. & Bodanszky, A. (1984) *The Practice of Peptide Synthesis*, Springer-Verlag, Heidelberg.

Bodanszky, M. (1985) *Int. J. Peptide Protein Res.* 25, 449-474.

Golemis (2002) Protein-Protein Interactions: A Molecular Cloning Manual (Illustrated), Cold Spring Harbor Laboratory, New York, ISBN 0879696281.

Smith et al., (2002) Short Protocols in Molecular Biology: A Compendium of Methods from Current Protocols in Molecular Biology, 5th Edition (Illustrated), John Wiley & Sons Inc., ISBN 0471250929.

Sambrook and Russell (2001) Molecular Cloning, Cold Spring Harbor Laboratory, New York, ISBN 0879695773.

DESCRIPTION OF THE RELATED ART

Skin (or dermal layers of a subject) is a highly complex organ covering the external surface of the body of a subject and merging, at various body openings, with the mucous membranes of the alimentary and other canals. It has multiple functions such as, for example, preventing water loss from the body. However, the primary function of the skin is as a protective barrier to prevent physical, chemical and bacterial agents damaging deeper tissues.

Skin comprises three layers, an outer layer, called the epidermis or cuticle, an inner layer or dermis and a fat layer or subdermis or hypodermis. The epidermis is several cells thick and has an external, horny layer of dead cells that are constantly shed from the surface and replaced from below by a basal layer of cells, called the stratum germinativum. The epidermis is made up primarily of keratinocytes, with the remaining cells being dendritic cells such as Langerhans cells and melanocytes. The epidermis is essentially cellular and non-vascular, there being relatively little extracellular matrix except for the layer of collagen and other proteins beneath the basal layer of keratinocytes. Keratinocytes of the basal layer are constantly dividing, and daughter cells subsequently move outwards, where they undergo a period of differentiation and are eventually sloughed off from the surface.

The dermis comprises of a network of collagenous extracellular material, elastic fibers, blood vessels, nerves, hair follicles with associated sebaceous glands (collectively known as the pilosebaceous unit), fibroblasts and sweat glands. The interface between the epidermis and dermis is extremely irregular and consists of a succession of papillae, or finger like projections. Beneath the basal epidermal cells along this interface the specialized extracellular matrix is organized into a distinct structure called the basement membrane.

Below the dermis lies a layer of fat, i.e., the hypodermis. The depth of this layer differs from one person to another. The hypodermis contains larger blood vessels and nerves, and is made up of clumps of adipose cells. The hypodermis lies on the muscles and bones, to which the whole skin structure is attached by connective tissue.

Dermal Wounds

The dermal layers of a subject may be damaged or wounded by any of a variety of insults, such as, for example, a burn and/or development of an ulcer and/or an infection. Complex wounds, such as, burns and ulcers are of particular concern, because these wounds may damage all layers of the skin, i.e., is a full-thickness wound, often requiring a skin graft for treatment. Moreover, such complex wounds are often chronic, because the body is unable to successfully heal the wound by the normal healing process. Many dermal wounds involve apoptosis of cells in one or more zones within the wound, for example ulcers and burns (see, for example, Iwasaki et al., *Br. J. Dermatol.*, 137: 647-348, 1997 and Herouy et al., *J Invest Dermatol.* 123: 1210-2, 2004).

In this respect, apoptosis is a form of programmed cell death in which a cell is broken down without inducing an inflammatory response, in contrast to necrosis in which results in induction of an inflammatory response. Without being bound by theory or mode of action, the distinction between the process of apoptosis and necrosis may be viewed as somewhat artificial, since some evidence suggests that the process of apoptosis coexists with and sometimes even leads to necrosis. Alternatively, or in addition, the two processes may be viewed as sharing some inducing and/or signaling and/or effector components. Several intracellular signaling pathways have been implicated in the induction of apoptosis, including the c-Jun N-terminal Kinase (JNK or SAPK) signal transduction pathway. For a detailed review of the role of the role of the JNK signal transduction pathway in apoptosis, refer to Kanda and Miura *J. Biochem.*, 136: 1-6, 2004).

Ulcers

Dermal skin ulcers are lesions on the skin caused by superficial loss of tissue, e.g., dermis and/or epidermis tissue and/or hypodermis, which fail to heal normally. This tissue loss is a result of necrosis and/or apoptosis of skin cells which is/are generally caused by vascular insufficiency and/or pressure. Examples of dermal skin ulcers include decubitus ulcers, diabetic ulcers, venous stasis ulcers and arterial ulcers. Decubitus ulcers are chronic ulcers that are caused by pressure applied to areas of the skin for extended periods of time. Wounds of this type are also often referred to as bedsores or pressure sores. Venous stasis ulcers are caused by stagnation of blood or other fluids from defective veins. Arterial ulcers refer to necrotic skin in the area around arteries having poor blood flow.

Decubitus ulcers are generally observed in subjects requiring prolonged periods in which they are immobile, e.g., in a bed. The prevalence of pressure ulcers in hospitals in UK and in USA is approximately 7-8%. In this respect, pressure ulcers are found in approximately 20-30% of subjects suffering from spinal cord injury, 3-10% of nursing home residents and 3-11% of subjects suffering from an acute injury. The estimated cost per annum for the care of pressure ulcers in UK is £150 million and in USA is USD 3 billion (Braddock et al., *Int. J. Dermatol.*, 38: 808-817, 1999).

Dermal ulcers are also a common complication and frequent cause of hospitalization for subjects suffering from diabetes. For example, in USA, the National Institute of Diabetes and Digestive and Kidney Diseases estimates that of the 16 million diabetic subjects, 15% will develop a diabetic ulcer. The cost of treatment of each diabetic ulcer case is estimated to be USD 10,000.00 to USD 15,000.00 per annum.

As for venous stasis ulcers and arterial ulcers, the development of these forms of wound increases markedly with increasing age (Braddock et al, *Int. J. Dermatol.*, 38: 808-817, 1999). In this respect, venous leg ulcers are the most common form of chronic wound with an incidence of over 2.5 million cases each year in USA alone (Onegnas et al., *Emerg. Med.*, 25: 45-53, 1999). The cost of treatment for venous stasis ulcers and arterial ulcers is estimated at approximately USD2 billion to USD3 billion per annum in USA alone (McGuckin et al., *Advances in Wound Care*, 11: 344-346, 1998).

Burns

A burn is a dermal wound generally caused by heat, electricity, a chemical or radiation. In a thermal burn (i.e., caused by heat), the initial wound is caused by heat necrosis of cells. The extent of the wound is then determined by the rate of dissipation or absorption of heat, which depends on several factors, such as, for example, the level of peripheral circulation, water content of the affected tissue, and the thickness of the skin (Artz and Yarbrough, In: Thermal, Chemical and Electrical Trauma, Text Book of Surgery, 9th ed., New York, Appleton-Century-Crafts, 1970). Electrical burns result from the heat produced by the flow of electricity through the resistance of body tissues (Latha and Babu *Burns*, 27: 309-317, 2001). Chemical burns are generally caused by chemical reactions rather than hyperthermic injury. For example, chemical reactions that result in a burn include coagulation of cellular proteins by reduction, corrosion, oxidation, formation of salts, poisoning of the cellular protoplasm or desiccation (Jelenko et al., *J. Trauma*, 10: 877-884, 1970).

A burn is generally characterized by the following three zones:
(i) Zone of coagulation—this is the area of the skin in which there is irreversible tissue loss as a result of coagulation of proteins in the skin cells caused by the burn;
(ii) Zone of stasis—is the area of the skin surrounding the zone of coagulation characterized by decreased perfusion. Suitable treatment may prevent loss of tissue in the zone of stasis thereby reducing the severity of a burn. However, in the absence of suitable treatment, cells in the zone of stasis die by necrosis and/or apoptosis resulting in tissue loss; and
(iii) Zone of hyperanemia—is the area of skin surrounding the zone of stasis in which tissue perfusion is increased relative to the level of perfusion in the zone of stasis. Tissue in this area generally recovers unless there is continued hypoperfusion or severe sepsis.

The depth of injury from a burn is described as first, second, or third degree. First-degree burns are the most shallow (superficial), affecting only the epidermis. Second-degree burns extend into the dermis. Third-degree burns involve all three layers of skin (epidermis, dermis, and fat layer), usually destroying the sweat glands, hair follicles, and nerve endings as well.

Biochemically, a burn is a severe form of trauma accompanied by a hypermetabolic response characterized by high cardiac output, increased oxygen consumption, compromised immune response and protein and fat catabolism (Pierre, E., et al. 1996. Growth hormone therapy in the treatment of burns. In: M. H. Torosian, ed. Growth hormone in critical illness: research and clinical studies. R. G. Landes Co, Texas. Pp 105-116). Such a hypermetabolic response may cause death in some subjects. The burn wound supports this vulnerable hypermetabolic state by producing and releasing thromboxane and pro-inflammatory cytokines (Meyer, et al. *J. Trauma* 31: 1008-1012, 1996). Thus, wound healing is important to survival and recovery in burn patients.

The American Burns Association estimates that there are approximately 1-2 million burn injuries each year. Of these, approximately 70,000 burn injuries require intensive care treatment and approximately 10,000-12,000 burn injuries result in death. The cost of intensive care treatment for burns is estimated to be in excess of USD 100 million per year in USA alone.

Current Therapies for Dermal Wounds
Wound Dressing or Skin Replacement

Generally, current treatments for dermal wounds involve covering a wound to reduce the risk of infection and to protect the wound site during wound healing. For example, such treatments involve debridement, or removal of dead and/or damaged cells from the site of the wound; treatment with antibiotics, if necessary; and regular dressing. However, in many cases, these forms of treatment are ineffective in the treatment of chronic wounds or severe wounds. In such cases, a skin graft using skin from the subject, artificial skin or skin from a cadaver is generally used to cover the wound. However, skin grafts are only useful in the case of well-vascularized wounds (Braddock et al., *Int. J. Dermatol.*, 38: 808-817, 1999). Accordingly, skin grafts may not be useful for the treatment of severe burns, i.e., in which vascular tissue in the hypodermis has been damaged or destroyed, or in subjects suffering from reduced circulation, e.g., diabetic subjects.

Moreover, notwithstanding that artificial skin demonstrates good biocompatibility and healing characteristics for the treatment of wounds, these materials are very expensive, which limits their widespread use. Whilst, cadaver skin is a relatively efficient and cheap approach for wound coverage, the risk of transmission of infections, e.g., human immunodeficiency virus (HIV), cytomegalovirus (CMV), herpes simplex virus (HSV) and/or hepatitis is a significant concern, thereby limiting application of cadaver skin.

Keratinocyte-Based Therapies

Svensjo et al., *J. Surg. Res.*, 99: 211-221, 2001 describe enhanced wound healing in wounds to which autologous keratinocyte suspensions were applied, e.g., by spray application. Such autologous keratinocyte suspensions also reduce scarring as a result of wound healing (Garner *Plast. Reconstr. Surg.*, 102: 135-139, 1998). Such reduced scarring is considered to be a result of keratinocytes suppressing collagen synthesis by fibroblasts during wound healing (Garner, supra; and Harrison et al., *British Journal of Dermatology*, 154: 401-410, 2006).

One disadvantage of such keratinocyte-based therapies is the time required to produce an autologous keratinocyte suspension for application to a subject. For example, sufficient time is required to obtain keratinocytes from a subject and culture a sufficient number of cells to treat a wound. Clearly this form of treatment is not amenable to the rapid treatment of a dermal wound.

Moreover, application of cultured cells to a subject increases the risk of infection as a result of contamination during the culturing process.

Photodynamic Treatment

U.S. Pat. No. 5,913,884 describes a photodynamic method for modulating wound healing by administering an effective amount of a photosensitizer targeted to macrophages by conjugation to a targeting moiety, e.g., low-density lipoprotein and photoactivating the photosensitizer. However, Parekh et al. *Lasers Surg. Med.* 24: 375-81, 1999, show that two porphyrin-based photodynamically active agents, have no effect on skin wound healing in a rat model of wound healing. Furthermore, Kubler et al. *Laser Surg. Med.* 18: 397-405, 1996 have shown that photodynamic therapy actually results in delayed wound healing Growth Factors The identification of growth factors as mediators of many of the processes integral to tissue repair has lead to interest in the development of therapeutics to enhance wound healing (Bennett and Schultz, *Am. J. Surg.*, 165: 728-732, 1993). Pierce and Mustoe *Ann. Rev. Med.*, 46: 467-481, 1995. Growth factors are reported to represent candidate therapeutics because they stimulate recruitment and/or production of cells required for wound healing, e.g. platelets, macrophages, endothelial cells, and/or fibroblasts. Furthermore, because growth factors bind to and signal through cell surface receptors, they do not require cellular uptake to exert a biological effect. Accordingly, growth factors are amenable to topical application to wounds.

For example, topical application of insulin-like growth factor (IGF)-I, has been shown to attenuate the hypermetabolic response associated with burns and to improve wound healing (Meyer et al., supra). IGF-I treatment improves wound healing by stimulating collagen formation and the mitogenicity of fibroblasts and keratinocytes (Martin, *Science* 276: 75-81, 1997). However, there are adverse side effects of treatment with IGF-I, such as hypoglycemia, mental status changes, edema, fatigue and headache, which limit the therapeutic utility of IGF-I in the treatment of burns (Jabri, et al. *Diabetes* 43: 369-374, 1994). These adverse side effects are most likely due to supra-physiological doses of free IGF-I, which are required for biological efficacy (Jabri et al., supra).

Furthermore, notwithstanding that epidermal growth factor (EGF) shows positive effects in in vitro wound healing assays, in vivo studies showed that EGF had little effect on venous ulcers (Falanga et al., *J. Dermatol. Surg. Oncol.*, 18: 604-606, 1992). Similarly, despite positive in vitro results, in vivo studies have shown that administration of interleukin-1 are ineffective in the treatment of pressure ulcers (Robson et al., *Wound Repair Regen.*, 2: 177-185, 1994).

SUMMARY OF INVENTION

The present invention is based in part on the production by the inventors of topical formulations of peptides that inhibit AP-1 signaling, e.g., by inhibiting c-Jun homodimerization and/or heterodimerization, and in part, on the finding that such topical formulations inhibit or delay or reduce apoptosis and/or necrosis following dermal wounding in vivo and promote wound healing in vivo.

Alternatively, or in addition, such a topical formulation enhances proliferation of a cell, e.g., a cell in a wound and/adjacent to a wound, e.g., a keratinocyte. Such a topical formulation preferably enhances wound healing and reduces scar formation.

For example, in a rodent model of full-thickness burn injury, the inventor found that treatment with a topical formulation of one or more peptide inhibitors of AP-1 signaling (e.g., by inhibiting c-Jun dimerization) inhibits, reduces or delays apoptosis and/or necrosis in the epidermis e.g., in the zone of stasis. Wound healing is also promoted or enhanced, as determined, for example, by early and/or more rapid re-epithelialization of the wound and separation of the eschar. Without being limited to any theory or mode of action, the inhibited, delayed or reduced apoptosis and/or necrosis may promote healing of a burn wound.

The present inventors also found that treatment with a topical formulation of one or more peptide inhibitors of AP-1 signaling reduced scar formation. Without being bound by theory or mode of action, the reduced scar formation may be a result of enhanced proliferation of a cell involved in wound healing, e.g., a keratinocyte.

It is understood by those skilled in the art that these data are readily extended to other dermal wounding contexts that involve apoptosis and/or necrosis.

The peptide inhibitor(s) used by the inventors have been demonstrated to inhibit AP-1 signaling as determined by binding to human c-Jun in yeast cells, and AP-1 regulated transcription in mammalian cells. The peptides were identified using a reverse hybrid screening technology that employed dual counter selection using the cytotoxic compounds cycloheximide and 5-fluoro orotic acid (5-FOA), in which only cells in which an interaction between JUN1 and JUNZ is disrupted could be rescued (Example 1). Peptides that rescued yeast cells in primary reverse hybrid screens were then expressed in mammalian cells expressing luciferase under operable control of AP-1 enhancer elements, to confirm their ability to inhibit AP-1 regulated transcription.

By virtue of their activity in yeast cells in preventing JUN1/JUNZ dimerization, the identified peptides are candidate AP-1 signaling inhibitory peptides that inhibit AP-1 signaling by direct inhibition of c-Jun homodimerization and/or heterodimerization. Such a mechanism of action is entirely consistent with the ability of the peptides to also prevent expression of a luciferase reporter gene in mammalian cells.

The AP-1 binding peptides can also be validated by other related methodologies, such as forward two hybrid screens using c-Jun as a bait. Peptide inhibitors of c-Jun/dependent autoactivation in two hybrid assays can be captured using counterselection approaches such as those described above. Similarly binding inhibitors of c-Jun to AP1 binding sites can be validated through standard one hybrid assays using this promoter element. A subset of such c-Jun binding, or DNA binding peptides might be expected to also inhibit AP1 signaling.

It is also possible that certain peptides inhibit AP-1 signaling by indirect means e.g., involving factors upstream of c-Jun that are conserved between yeasts and mammals. For example, yeast cells possess a stress-responsive MAPK (SAPK) cascade; a multistep phosphorelay system; and AP-1-like transcription factor (Yap 1) that govern the response of yeasts to oxidative stress (Ikner et al., *Mutation Res.* 569, 13-27, 2005), and which may be involved in regulating the apoptotic response to cytotoxic compounds used in the reverse hybrid screens. The yeast MAPK (SAPK) cascade involves signaling from a complex comprising yeast homologs of human Cdc42 and Pak1 (i.e., Cdc42 and Step 20, respectively) to the MAPKKK Ste11, which regulates the MAPKK Pbs2 and, in turn, the MAPK Hog1 to regulate gene expression, membrane transport, cell cycle progression, etc. The yeast phosphorelay system appears to converge on Pbs2 MAPKK of the Hog1 SAPK cascade and is initiated by the transmembrane protein Shot which activates Pbs2 through the MAPKKK Ste11 of the Hog1 SAPK cascade. The AP-1-like transcription factor (Yapl) appears to serve as an oxidative stress sensor that directly regulates transcription albeit independently of the SAPK pathway. Without being bound by any theory or mode of action, the present inventors reason that a peptide identified in a counter selection screen such as a reverse hybrid screening of yeast cells may rescue yeast cells from an event upstream of Hog1 in yeast that would otherwise lead to activation of these stress responses (including cell-cycle modulation) leading to cell death. If the same peptide also recognizes a homologous mammalian AP-1 pathway component upstream of c-Jun and/or INK, inhibition of that component would also explain the observed reduction in AP-1 mediated activation of luciferase reporter gene expression observed in mammalian cells.

Accordingly, the identified peptides from yeast reverse hybrid screens not to be limited by their ability to inhibit c-Jun dimerization, and are designated herein as "AP-1 inhibitors" or "AP-1 complex formation inhibitors" or "AP-1 signaling inhibitors" or similar term. It is to be understood that such terminology includes any compound that directly inhibits or reduces c-Jun dimerization and/or inhibits or reduces upstream indirect effects e.g., acting on phosphorylation of Cdc42, Pak1 or Rac1, or dimerization of Cdc42, Pak1 or Rac1 in mammalian cells. Preferred AP-1 signaling inhibitory compounds will inhibit later steps in the AP-1 signaling pathway e.g., c-Jun dimerization, to thereby provide greater specificity than, for example, a JNK inhibitory peptide.

It is also to be understood that the term "c-Jun dimerization" includes c-Jun self-dimerization or homodimerization, and heterodimerization between c-Jun and another protein e.g., ATF-2, c-Fos or JNK and preferably between c-Jun and ATF-2 or between c-Jun and c-Fos (i.e., a c-Jun heterodimer) or an analog of said isolated peptide or protein domain.

The results obtained by the inventors also suggest that a topical composition comprising any inhibitor of AP-1 signaling is useful for the treatment of a dermal wound.

Accordingly, the present invention provides a topical composition comprising (i) an amount of an AP-1 signaling inhibitor sufficient to reduce, delay or prevent apoptosis and/or necrosis induced by dermal wounding and/or to induce and/or enhance proliferation of a cell; and (ii) a suitable carrier or excipient e.g., a topical carrier or excipient or other carrier or excipient for dermal application.

For example, the present invention provides a topical composition comprising (i) an amount of an AP-1 signaling inhibitor sufficient to reduce, delay or prevent apoptosis induced by dermal wounding; and (ii) a suitable carrier or excipient e.g., a topical carrier or excipient or other carrier or excipient for dermal application.

For example, the present invention provides a topical composition comprising (i) an amount of an AP-1 signaling inhibitor sufficient to reduce, delay or prevent necrosis induced by dermal wounding; and (ii) a suitable carrier or excipient e.g., a topical carrier or excipient or other carrier or excipient for dermal application.

For example, the present invention provides a topical composition comprising (i) an amount of an AP-1 signaling inhibitor sufficient to reduce, delay or prevent apoptosis and necrosis induced by dermal wounding; and (ii) a suitable carrier or excipient e.g., a topical carrier or excipient or other carrier or excipient for dermal application.

In another example, the present invention provides a topical composition comprising (i) an amount of an AP-1 signaling inhibitor sufficient to induce and/or enhance proliferation of a cell; and (ii) a suitable carrier or excipient e.g., a topical carrier or excipient or other carrier or excipient for dermal application. For example, the cell is in a wound or adjacent to a wound, e.g., the cell is a keratinocyte.

In one example, an inhibitor of AP-1 signaling interacts with JNK or a nucleic acid encoding same to reduce expression and/or activity thereof. For example, an inhibitor interacts with JNK and prevents JNK from phosphorylating a protein, such as, for example, c-Jun and/or ATF2 and/or c-Fos and/or Bcl-$X_L$ and/or Bim and/or Bmf.

Alternatively, or in addition, an inhibitor of JNK-mediated signal transduction interacts with and reduces or prevents activity of another molecule involved in INK-mediated signal transduction. Suitable molecules will be apparent to the skilled artisan and/or are described herein. Examples of molecules involved in JNK-mediated signal transduction are depicted in FIG. 1. For example, an inhibitor inhibits and/or reduces activity and/or expression of a molecule that interacts with JNK, e.g., a protein phosphorylated and/or activated by JNK or nucleic acid encoding same and prevents activity or expression of that molecule. For example, an inhibitor reduces or prevents the expression and/or activity of c-Jun, ATF2, c-Fos and/or NFAT4. For instance, an inhibitor reduces or prevents formation of a heterodimer and/or homodimer comprising c-Jun.

Suitable inhibitors will be apparent to the skilled artisan based on the description herein, and include, for example, a peptide, a peptide analogue, an antibody, an antibody fragment, a nucleic acid, or a small molecule. For example, an inhibitor of AP-1 signaling is a peptide, e.g., a peptide selected individually or collectively from the group consisting of:
(i) a peptide encoded by a nucleic acid comprising a sequence set forth in any one of SEQ ID NOs: 1-25;
(ii) a peptide comprising a sequence set forth in any one of SEQ ID NOs: 26-73, 122-125, 130 or 132; and
(iii) an analogue of (i) or (ii) selected from the group consisting of (a) the sequence of (i) or (ii) comprising one or more non-naturally-occurring amino acids; (b) the sequence of (i) or (ii) comprising one or more non-naturally-occurring amino acid analogues; (c) an isostere of (i) or (ii); (d) a retro-peptide analogue of (i) or (ii); and (e) a retro-inverted peptide analogue of (i) or (ii).

By "individually" is meant that the invention encompasses the recited peptides or groups of peptides separately, and that, notwithstanding that individual peptides or groups of peptides may not be separately listed herein the accompanying claims may define such peptides or groups of peptides separately and divisibly from each other.

By "collectively" is meant that the invention encompasses any number or combination of the recited peptides or groups of peptides, and that, notwithstanding that such numbers or combinations of peptides or groups of peptides may not be specifically listed herein the accompanying claims may define such combinations or sub-combinations separately and divisibly from any other combination of peptides or groups of peptides.

For example, the inhibitor is a retro-inverted peptide analogue capable of inhibiting or reducing AP-1 signaling. For example, the retro-inverted peptide analogue comprises an amino acid sequence set forth in any one of SEQ ID NOs: 73-120, 125-128 or 130. In one exemplified form of the invention, the retro-inverted peptide analogue comprises an amino acid sequence set forth in SEQ ID NO: 104.

Because JNK-mediated signal transduction occurs within a cell, a suitable inhibitor is capable of entering a cell. In one example, an inhibitor is conjugated to or fused to a protein transduction domain. A suitable protein transduction domain will be apparent to the skilled artisan based on the description herein and includes a HIV-tat basic region peptide (e.g., comprising a sequence set forth in any one of SEQ ID NOs: 137-144) or a retroinverted analogue thereof (e.g., comprising a sequence set forth in any one of SEQ ID NOs: 144-152). Another suitable protein transduction domain is a Kaposi fibroblast growth factor (FGF) hydrophobic peptide protein transduction domain (e.g., comprising an amino acid sequence set forth in SEQ ID NO: 159 or 160) or a retro-inverted analog thereof (e.g., comprising an amino acid sequence set forth in SEQ ID NO: 161 or 162).

As used herein, the term "dermal wounding" shall be taken to mean a lesion to one or more layers of skin of a subject, wherein said lesion comprises one or more apoptotic dermal cells and/or one or more necrotic dermal cells. For example, a trauma to a dermal layer of a subject induces cells in one or more dermal layers of a subject to undergo apoptosis and/or necrosis. Accordingly, damage to a dermal layer of a subject characteristic of the wound is mediated by or promoted by apoptosis and/or necrosis. The term "dermal wound" shall be taken to include a wound that affects an epidermal layer of a subject and/or a dermal layer of a subject and/or a hypodermal layer of a subject.

As will be apparent to the skilled artisan from the foregoing definition of dermal wounding, the present invention provides a topical composition suitable for the treatment of a wound mediated by or promoted by apoptosis and/or necrosis. For example, the wound is a chronic wound. Examples of suitable wounds include, an ulcer, such as for example, a decubitis ulcer and/or a diabetic ulcer and/or a venous ulcer and/or an arterial ulcer. In one example of the invention, the dermal wound is a burn, e.g., a thermal burn and/or a chemical burn and/or an electrical burn and/or a radiation-induced burn. Alternatively, a burn is induced or mediated by a cold temperature. In one exemplified form of the invention, a dermal wound is a thermal burn.

An "amount of an inhibitor sufficient to prevent or reduce apoptosis and/or necrosis" or "amount of an inhibitor sufficient to prevent or reduce apoptosis" or "amount of an inhibitor sufficient to prevent or reduce necrosis" will be understood by the skilled artisan to mean that the topical composition comprises a sufficient quantity of an inhibitor to reduce the number of cells undergoing apoptosis and/or necrosis induced by dermal wounding and/or to prevent or delay or inhibit apoptosis and/or necrosis in a cell induced by dermal wounding. The skilled artisan will be aware that such an amount will vary depending on the inhibitor used, e.g., as a result of variation in the bioactivity of an inhibitor, and/or the severity of the wound. Accordingly, this term is not to be construed to limit the invention to a specific quantity, e.g., weight of an inhibitor, rather the present invention encompasses any amount of the inhibitor sufficient to prevent or reduce apoptosis and/or necrosis induced by dermal wounding. Methods for detecting apoptosis and/or necrosis and/or for determining the amount of an inhibitor sufficient to reduce or delay or prevent apoptosis and/or necrosis will be apparent to the skilled artisan and/or described herein.

An "amount of an inhibitor sufficient to induce and/or enhance proliferation of a cell" will be understood by the skilled artisan to mean that the topical composition comprises a sufficient quantity of an inhibitor to induce a cell to divide or proliferate and/or to enhance the rate of proliferation and/or regularity at which a cell divides. The skilled artisan will be aware that such an amount will vary depending on the inhibitor used, e.g., as a result of variation in the bioactivity of an inhibitor, and/or the severity of the wound. Accordingly, this term is not to be construed to limit the invention to a specific quantity, e.g., weight of an inhibitor, rather the present invention encompasses any amount of the inhibitor sufficient to induce and/or enhance proliferation of a cell in a wound. Methods for detecting cellular proliferation and/or for determining the amount of an inhibitor sufficient to induce and/or enhance proliferation of a cell will be apparent to the skilled artisan and/or described herein.

In one example, the topical composition as described herein according to any embodiment comprises an amount of an AP-1 signaling inhibitor sufficient to additionally induce re-epithelialization of a wound. As used herein, the term "re-epithelialization" shall be taken to mean the process by which one or more dermal layer(s) is produced over and/or within a wound. In this respect, the term "re-epithelialization" does not require the dermal layer(s) be restored such that they are the same as the dermal layers before wounding. For example, re-epithelialization may result in the formation of a scar, e.g., a keloid scar, a hypertrophic scar or a contracture. In one example, the topical composition as described herein according to any embodiment comprises an amount of an inhibitor of JNK-mediated signal transduction sufficient to induce re-epithelialization of a wound with reduced scar formation, e.g., compared to a wound to which the inhibitor has not been applied.

As used herein, the term "suitable carrier or excipient" shall be taken to mean a compound or mixture thereof that is suitable for use in a topical formulation albeit not necessarily limited in use to that context. In contrast, a "topical carrier or excipient" is compound or mixture thereof that is described in the art only with reference to a use in a topical formulation. The term "carrier or excipient for dermal application" shall be taken to mean a compound or mixture thereof that is suitable for application to one or more dermal layers not necessarily to the external layer of skin, and which may be suitable for use in other contexts.

A carrier and excipient useful in the topical composition of the present invention will generally not inhibit to any significant degree a relevant biological activity of the active compound e.g., the carrier or excipient will not significantly inhibit the inhibitory activity of the active compound with respect to c-Jun dimerization or apoptosis and/or necrosis. For example, the carrier or excipient provides a buffering activity to maintain the compound at a suitable pH to thereby exert its biological activity, e.g., the carrier or excipient is phosphate buffered saline.

Alternatively, or in addition, the carrier or excipient comprises a compound that enhances cellular uptake of the inhibitor and/or enhances transdermal delivery of the inhibitor. For example, the carrier or excipient comprises a skin penetration enhancer, such as, for example, dipropylene glycol and/or oleyl alcohol. Alternatively, or in addition, a carrier or excipient comprises a liposome to facilitate cellular uptake.

Alternatively, or in addition, the carrier or excipient comprises a compound that enhances the activity of an AP-1 signaling inhibitor and/or reduce inhibition of an AP-1 signaling inhibitor, e.g., a protease inhibitor and/or a DNase inhibitor and/or a RNase inhibitor to thereby enhance the stability of the inhibitor.

In one example, the topical composition as described herein according to any embodiment comprises an additional compound, such as, for example, a growth factor to enhance re-epithelialization of a wound and/or an antibiotic and/or an anaesthetic. Suitable additional compounds will be apparent to the skilled artisan based on the description herein.

The skilled artisan will be aware that the topical composition may be in a variety of forms, such as, for example, a liquid or a cream or a gel or a lotion. For example, the topical composition is a liquid, e.g., a saline liquid and/or a liquid comprising glucose. Such a liquid is suitable for application to a wound by, for example, spraying or washing or direct contact.

The present invention also provides a topical composition comprising (i) an amount of a retroinverted peptide comprising an amino acid sequence set forth in SEQ ID NO: 104 sufficient to reduce or prevent apoptosis and/or necrosis induced by dermal wounding and/or induce proliferation of a cell; and (ii) a suitable carrier or excipient e.g., a topical carrier or excipient or other carrier or excipient for dermal application. For example, the carrier or excipient is phosphate buffered saline.

The present invention also provides a wound dressing comprising a topical composition as described herein according to any embodiment. For example, the present invention provides a wound dressing such as, for example, a fabric bandage or a plastic bandage or a gauze bandage or a gauze dressing or a trauma dressing impregnated with a topical composition as described herein according to any embodiment. Alternatively, or in addition, the dressing comprises a scaffold, e.g., a biodegradable scaffold. For example, the scaffold comprises collagen and/or poly(lactic) acid and/or poly(glycolic) acid and/or fibrin. Such a scaffold may be porous or non-porous or a mixture thereof. An advantage of such scaffolds is that they adapt to the shape of a wound and deliver a therapeutic compound to the site of wounding. Moreover, as the wound heals, the scaffold breaks down, thereby reducing biological waste.

The present invention also provides a method for producing a topical composition described herein according to any embodiment. For example, such a method comprises mixing or otherwise combining an amount of an AP-1 signaling inhibitor sufficient to reduce or prevent apoptosis and/or necrosis induced by dermal wounding and a suitable carrier or excipient e.g., a topical carrier or excipient or other carrier or excipient for dermal application.

In one example, the method additionally comprises producing or obtaining an AP-1 signaling inhibitor. For example, a peptide inhibitor or a nucleic acid inhibitor is produced synthetically or recombinantly, using a method known in the art and/or described herein. Methods for the production of other AP-1 signaling inhibitors will be apparent to the skilled artisan based on the description herein.

The present invention also provides a method of treatment of a dermal wound, the method comprising topically administering to a subject in need thereof a topical composition as described herein according to any embodiment, for a time and under conditions sufficient for the AP-1 signaling inhibitor to reduce or prevent apoptosis and/or necrosis induced by dermal wounding, thereby treating the dermal wound.

As used herein, the term "topically administering" shall be taken to mean that a topical composition is applied to a dermal layer of a subject. For example, a topical composition is administered to a dermal wound and, optionally to a region of a dermal layer surrounding said dermal wound. In this respect, the present invention contemplates direct application of an AP-1 signaling inhibitor to a dermal layer of a subject, e.g., by spraying a liquid composition or direct application of a gel or cream. The present invention also contemplates application an AP-1 signaling inhibitor by way of a wound dressing or an artificial skin comprising a topical composition as described herein according to any embodiment. In this respect, as exemplified herein the present inventors have applied a wound dressing comprising an AP-1 signaling inhibitor to a subject suffering from a thermal burn to treat said burn.

In one example, a peptide AP-1 signaling inhibitor is administered to a subject by producing a recombinant cell expressing said peptide and topically administering a topical composition comprising said cell to said subject. For example, the cell is a stem cell, such as, for example a pluripotent or multipotent stem cell or other stem cell capable of differentiating to produce a dermal cell. For example, the cell is an epidermal stem cell or a follicular stem cell.

In one example, a topical composition comprising a nucleic acid AP-1 signaling inhibitor is administered to a subject by particle bombardment.

As used herein, the term "subject in need thereof" shall be taken to mean a subject that has developed or suffers from a dermal wound, e.g., a chronic dermal wound. For example, the subject suffers from an ulcer, such as, for example, a decubitis ulcer and/or a diabetic ulcer and/or a venous ulcer and/or an arterial ulcer. In another example, the subject suffers from a surgical wound, such as, for example, an incision. Treatment with a topical composition described herein according to any embodiment will improve healing of such a wound. In one example of the invention, a subject suffers from a burn, e.g., a thermal burn and/or a chemical burn and/or an electrical burn and/or a radiation-induced burn. In one exemplified form of the invention, a subject in need of treatment suffers from a thermal burn.

A method of treatment as described herein according to any embodiment shall not be taken to be limited to a single application of a topical composition described herein according to any embodiment. Rather, the present invention also contemplates repeated topical administration of a topical composition as described herein according to any embodiment. For example, a topical composition is applied each time that a dermal wound is washed and/or dressed.

In one example, a method of treatment as described herein according to any embodiment additionally comprises providing or obtaining a topical composition as described herein according to any embodiment or information concerning same. For example, the present invention provides a method of treatment of a subject in need thereof, said method comprising:
(i) determining a subject suffering from or developing a dermal wound;
(ii) obtaining a topical composition as described herein according to any embodiment; and
(iii) topically administering said topical composition to said subject.

The present invention also provides a method of treatment of a subject in need thereof, said method comprising:
(i) identifying a subject suffering from or developing a dermal wound; and
(ii) recommending topical administration of a topical composition as described herein according to any embodiment.

Alternatively, a method of treatment comprises topically administering or recommending topical administration of a topical composition as described herein according to any embodiment to a subject previously identified as suffering from a dermal wound.

The present invention also provides for the use of an amount of an AP-1 signaling inhibitor sufficient to reduce or prevent apoptosis and/or necrosis induced by dermal wounding and/or induce and/or enhance proliferation of a cell in the manufacture of a medicament for dermal application for the treatment of a dermal wound.

The present invention also provides the use of an AP-1 signaling inhibitor in the manufacture of a topical composition for the treatment of a dermal wound.

The present invention also provides the use of a topical composition as described herein according to any embodiment in the manufacture of a medicament for dermal application for the treatment of a dermal wound.

The present invention also provides a topical composition as described herein according to any embodiment for topical application for treating a dermal wound.

The present invention also provides a method for identifying a compound suitable for topical administration for the treatment of a dermal wound, said method comprising:
(i) identifying a compound capable of inhibiting or reducing AP-1 signaling;
(ii) topically administering an amount of the compound identified at (i) sufficient to reduce or prevent apoptosis and/or necrosis induced by dermal wounding to a dermal wound;
(iii) comparing the level of apoptosis and/or necrosis and/or the amount of wound healing in the wound to the level of apoptosis and/or necrosis and/or the amount of wound healing in a dermal wound to which the compound has not been administered; and
(iv) selecting a compound that reduces the level of apoptosis and/or necrosis and/or enhances the level of wound healing in a dermal wound to which it is administered compared to the level of apoptosis and/or necrosis and/or wound healing in a dermal wound to which the compound has not been administered, thereby identifying a compound suitable for topical administration for the treatment of a dermal wound.

The present invention also provides a method for identifying a compound suitable for topical administration for the treatment of a dermal wound, said method comprising:
(i) identifying a compound capable of inhibiting or reducing AP-1 signaling;
(ii) topically administering to a cell the compound identified at (i) for a time and under conditions sufficient for cellular proliferation;

(iii) comparing the level of proliferation of the cell to the proliferation of a cell or cellular proliferation to which the compound has not been administered; and
(iv) selecting a compound that enhances the level of proliferation of the cell to which it is administered compared to the level of proliferation of the cell to which the compound has not been administered, thereby identifying a compound suitable for topical administration for the treatment of a dermal wound. For example, the cell is a cell in vitro. Alternatively, the cell is in a dermal wound or in a dermal layer of a subject.

For example, the dermal wound is a thermal burn. For instance, the dermal wound is a thermal burn induced by applying a hot solid surface to the skin of a subject, e.g., a surface having a temperature of at least about 90° C. or at least about 95° C.

In one example, the method additionally comprises:
(v) optionally, determining the structure of the compound;
(vi) optionally, providing the name or structure of the compound; and
(vii) providing the compound.

DETAILED DESCRIPTION OF THE PREFERRED EMBODIMENTS

AP-1 Signaling Inhibitors

Figure 1:
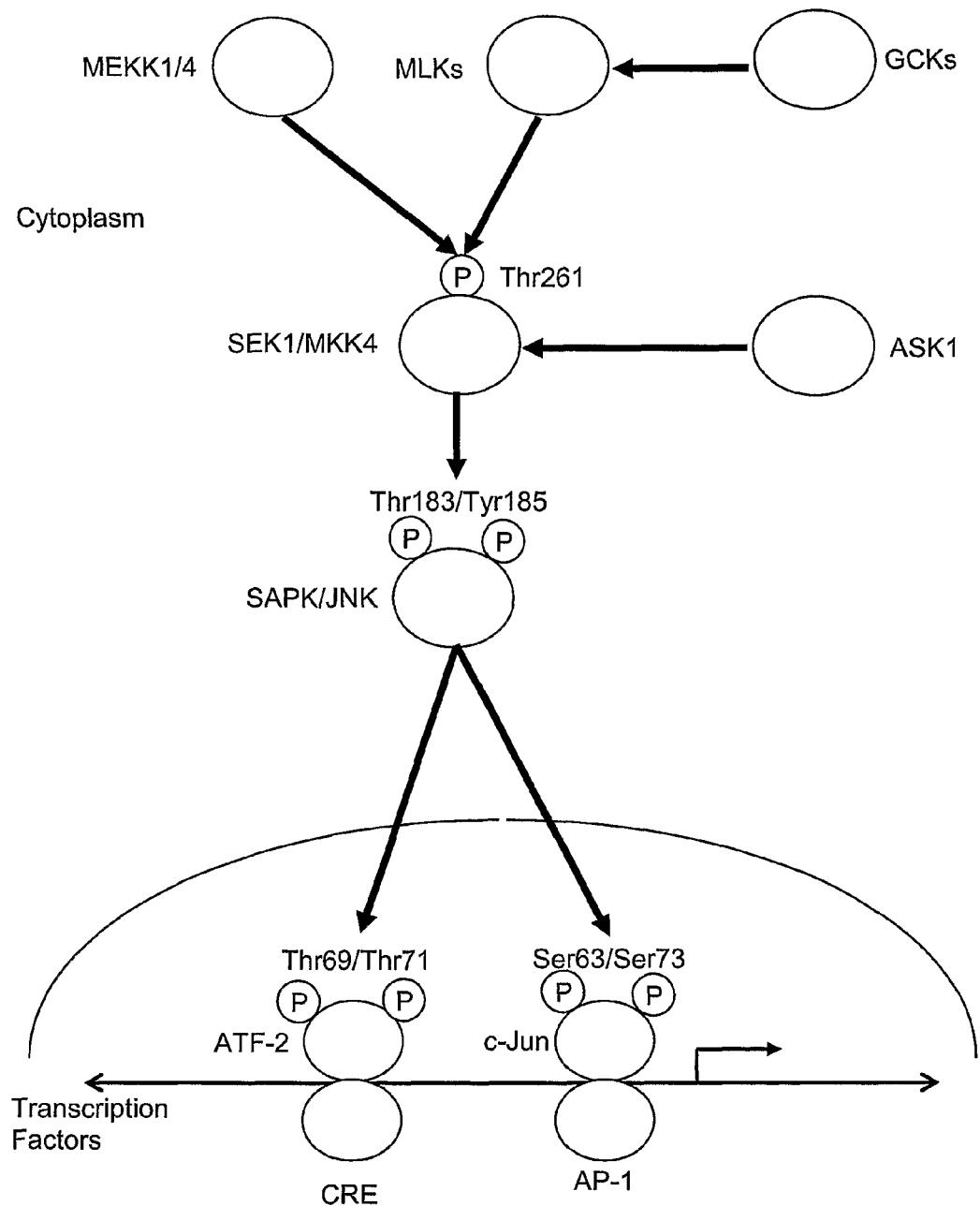
FIG. 1 is a schematic representation showing proteins involved in AP-1 signaling. In one example, the present invention encompasses a topical composition comprising an inhibitor of any protein involved in AP-1 signaling, including those proteins described in FIG. 1 and/or described herein and/or known in the art and a suitable carrier or excipient e.g., a topical carrier or excipient or other carrier or excipient for dermal application.

The topical compositions as described herein according to any embodiment may comprise any one or more AP-1 signaling inhibitors.

1. Nucleic Acid Inhibitors

In one example of the invention, a nucleic acid AP-1 signaling inhibitor reduces or prevents expression of a protein or nucleic acid required for AP-1 signaling.

In this respect, the term "expression" will be understood by the skilled artisan to include transcription and/or translation. Accordingly, an inhibitor that reduces expression inhibits transcription and/or inhibits translation.

For example, an AP-1 signaling inhibitor reduces or prevents expression of JNK. For example, the inhibitor comprises nucleic acid such as, for example, an antisense nucleic acid, peptide nucleic acid (PNA), ribozyme, or small interfering RNA (siRNA), short hairpin RNA (shRNA) which is complementary, in whole or in part, to a target molecule comprising a sense strand, and can hybridize with a target molecule, e.g., INK-encoding mRNA. When introduced into a cell using suitable methods, such a nucleic acid inhibits the expression of the JNK gene encoded by the sense strand. Antisense nucleic acid, ribozymes (e.g., Cech et al., U.S. Pat. No. 4,987,071; Cech et al., U.S. Pat. No. 5,116,742; Bartel and Szostak, *Science* 261, 1411-1418, 1993), nucleic acid capable of forming a triple helix (e.g., Helene, *Anticancer Drug Res.* 6, 569-584, 1991), PNAs (Hyrup et al., *Bioorganic & Med. Chem.* 4, 5-23, 1996; O'Keefe et al., *Proc. Natl Acad. Sci. USA* 93, 14670-14675, 1996), small interfering RNAs or short hairpin RNAs may be produced by standard techniques known to the skilled artisan, based upon the sequences disclosed herein. Examples of suitable siRNA include a siRNA comprising a sequence set forth in SEQ ID NO: 135 or 136.

In another example of the invention, an AP-1 signaling inhibitor reduces or prevents expression of a nucleic acid, peptide, polypeptide or protein that is phosphorylated and/or activated by INK. For example, the inhibitor reduces or prevents expression of a protein such as, for example, c-Jun, ATF2 or c-Fos. An example of a suitable nucleic acid inhibitor is a DNAzyme designated Dz13 comprises a nucleotide sequence set forth in SEQ ID NO:133. This DNAzyme has been previously shown to be capable of reducing expression of c-Jun in Khachigian et al., *J. Biol. Chem.*, 277: 22985-22991, 2002. Optionally, the DNAzyme includes a 3'-3' inverted thymidine linkage to thereby improve resistance against nuclease degradation (Santiago et al., *Nat. Med.*, 5: 1264-1269, 1999).

Another AP-1 signaling inhibitor that reduces or prevents expression of c-Jun is a siRNA comprising a nucleotide sequence set forth in SEQ ID NO: 134.

Alternatively, or in addition an inhibitor of AP-1 signaling reduces or inhibits transcriptional activity induced by AP-1 activity. For example, an AP-1 decoy oligonucleotide comprising a sequence set forth in SEQ ID NO: 132 binds to active members of the AP-1 protein complex. As discussed in Desmet et al., *Am. J. Crit. Care Med.*, 172: 671-678, 2005 an oligonucleotide comprising a sequence set forth in SEQ ID NO: 132 is capable of reducing or inhibiting AP-1 signaling.

To facilitate cellular uptake, a nucleic acid inhibitor may be linked or conjugated to a protein transduction domain, e.g., as described herein. Suitable methods for linking or conjugating a nucleic acid to a protein transduction domain will be apparent to the skilled artisan and/or described in, for example, International Application No. PCT/US93/07833.

Alternatively, a nucleic acid inhibitor is identified from a library of nucleic acids using a method known in the art and/or described herein.

2. Peptide Inhibitors and Analogues and Derivatives Thereof

In another example of the invention, an AP-1 signaling is a peptide or a peptide analogue or a peptide derivative. For example, the inhibitor binds to or interacts with JNK and inhibits JNK activity. For example, the peptide prevents or reduces the ability of JNK to phosphorylate a protein, such as, for example c-Jun, c-fos or ATF2. For example, a peptide inhibitor capable of binding to JNK and reducing or preventing MK activity is a TI-JIP peptide comprising an amino acid sequence set forth in SEQ ID NO: 129 (e.g., as described in Barr et al., *J. Biol. Chem.*, 277: 10987-10997, 2002). An example of an analog of TI-JIP is a retro-inverted analog of TI-JIP, e.g., comprising an amino acid sequence set forth in SEQ ID NO: 130. Examples of additional suitable peptides include a peptide described by Bonny et al., *Diabetes*, 50: 77-82, 2001, e.g., comprising an amino acid sequence selected from the group consisting of SEQ ID NO: 121, SEQ ID NO: 122, SEQ ID NO: 123 and SEQ ID NO: 124.

In another example, an AP-1 signaling inhibitor is a peptide capable of reducing or inhibiting the activity of a cellular component involved in activating or phosphorylating JNK, or, alternatively, capable of inhibiting a cellular component, e.g., a protein activated and/or phosphorylated by JNK. For example, a peptide inhibitor is capable of inhibiting activity of c-Jun and/or c-Fos and/or ATF2. For example, a peptide inhibitor is capable of inhibiting dimerization of c-Jun (e.g., homodimerization and/or heterodimerization of c-Jun) to thereby inhibit or reduce AP-1 signaling.

In one example, a suitable peptide comprises an amino acid sequence set forth in any one of SEQ ID NOs: 26-72, 164 or a peptide encoded by a nucleic acid comprising a sequence set forth in any one of SEQ ID NOs: 1-25.

Additional peptide inhibitors of AP-1 signaling are described in Bogoyevitch et al., *Biochimica et Biophysica Acta*, 1697: 89-101, 2004.

Protein Transduction Domains

To facilitate peptide entry into a cell, the peptide may be conjugated to (e.g., expressed as a fusion with) a protein transduction domain. As used herein, the term "protein transduction domain" shall be taken to mean a peptide or protein that is capable of enhancing, increasing or assisting penetration or uptake of a compound conjugated to the protein transduction domain into a cell either in vitro or in vivo. Those skilled in the art will be aware that synthetic or recombinant peptides can be delivered into cells through association with a protein transduction domain such as the TAT sequence from HIV or the Penetratin sequence from the Antenapaedia homeodomain protein (see, for example, Temsamani and Vidal, *Drug Discovery Today* 9: 1012-1019, 2004, for review).

A suitable protein transduction domain will be apparent to the skilled artisan and includes, for example, HIV-1 TAT fragment (e.g., comprising an amino acid sequence set forth in any one of SEQ ID NOs: 137-144), signal sequence based peptide 1 (e.g., comprising an amino acid sequence set forth in SEQ ID NO: 153), signal sequence based peptide 2 (e.g., comprising an amino acid sequence set forth in SEQ ID NO: 154), transportan (e.g., comprising an amino acid sequence set forth in SEQ ID NO: 155), amphiphilic model peptide (e.g., comprising an amino acid sequence set forth in SEQ ID NO: 156), polyarginine (e.g., comprising an amino acid sequence set forth in SEQ ID NO: 157) or a Kaposi fibroblast growth factor (FGF) hydrophobic peptide protein transduction domain (e.g., comprising an amino acid sequence set forth in SEQ ID NO: 159 or 160).

Additional suitable protein transduction domains are described, for example, in Zhao and Weisledder *Medicinal Research Reviews*, 24: 1-12, 2004 and Wagstaff and Jans, *Current Medicinal Chemistry*, 13: 1371-1387, 2006.

Linkers

Each of the components of a peptide inhibitor described herein may optionally be separated by a linker that facilitates the independent folding of each of said components. A suitable linker will be apparent to the skilled artisan. For example, it is often unfavorable to have a linker sequence with high propensity to adopt α-helix or β-strand structures, which could limit the flexibility of the protein and consequently its functional activity. Rather, a more desirable linker is a sequence with a preference to adopt extended conformation. In practice, most currently designed linker sequences have a high content of glycine residues that force the linker to adopt loop conformation. Glycine is generally used in designed linkers because the absence of a β-carbon permits the polypeptide backbone to access dihedral angles that are energetically forbidden for other amino acids.

Preferably, the linker is hydrophilic, i.e. the residues in the linker are hydrophilic.

Linkers comprising glycine and/or serine have a high freedom degree for linking of two proteins, i.e., they enable the fused proteins to fold and produce functional proteins. Robinson and Sauer *Proc. Natl. Acad. Sci.* 95: 5929-5934, 1998 found that it is the composition of a linker peptide that is important for stability and folding of a fusion protein rather than a specific sequence.

In one exemplified form of the invention a linker is a glycine residue. In some forms of the invention, the linker is included in, for example a protein transduction domain.

Peptide Derivatives

The present invention also encompasses a derivative of a peptide inhibitor of AP-1 signaling. As used herein the term "derivative" shall be taken to mean a peptide that is derived from an inhibitory peptide as described herein e.g., a fragment or processed form of the peptide. The term "derivative" also encompasses fusion proteins comprising a peptide of the invention. For example, the fusion protein comprises a label, such as, for example, an epitope, e.g., a FLAG epitope or a V5 epitope or an HA epitope. For example, the epitope is a FLAG epitope. Such a tag is useful for, for example, purifying the fusion protein.

The term "derivative" also encompasses a derivatized peptide, such as, for example, a peptide modified to contain one or more-chemical moieties other than an amino acid. The chemical moiety may be linked covalently to the peptide e.g., via an amino terminal amino acid residue, a carboxy terminal amino acid residue, or at an internal amino acid residue. Such modifications include the addition of a protective or capping group on a reactive moiety in the peptide, addition of a detectable label, and other changes that do not adversely destroy the activity of the peptide compound.

Peptide Analogues

In another example of the invention, an AP-1 inhibitor is a peptide analogue. As used herein, the term "analogue" shall be taken to mean a peptide that is modified to comprise one or more naturally-occurring and/or non-naturally-occurring amino acids, provided that the peptide analogue is capable of inhibiting or reducing AP-1 signaling. For example, the term "analogue" encompasses an inhibitory peptide comprising one or more conservative amino acid changes. The term "analogue" also encompasses a peptide comprising, for example, one or more D-amino acids. Such an analogue has the characteristic of, for example, protease resistance.

Suitable peptide analogues include, for example, a peptide comprising one or more conservative amino acid substitutions. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine).

It also is contemplated that other sterically similar compounds may be formulated to mimic the key portions of the peptide structure. Such compounds, which may be termed peptidomimetics, may be used in the same manner as an AP-1 signaling peptide inhibitor. The generation of such an analogue may be achieved by the techniques of modeling and chemical design known to those of skill in the art. It will be understood that all such sterically similar peptide analogues fall within the scope of the present invention.

An example of an analogue of a peptide of the invention comprises one or more non-naturally occurring amino acids or amino acid analogues. For example, a peptide inhibitor as described herein comprises one or more naturally occurring non-genetically encoded L-amino acids, synthetic L-amino acids or D-enantiomers of an amino acid. For example, the peptide comprises only D-amino acids. For example, the analogue comprises one or more residues selected from the group consisting of: hydroxyproline, β-alanine, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylananine 3-benzothienyl alanine 4-chlorophenylalanine, 2-fluorophenylalanine, 3-fluorophenylalanine, 4-fluorophenylalanine, penicillamine, 1,2, 3,4-tetrahydro-tic isoquinoline-3-carboxylic acid β-2-thienylalanine, methionine sulfoxide, homoarginine, N-acetyl lysine, 2,4-diamino butyric acid, ρ-aminophenylalanine, N-methylvaline, homocysteine, homoserine, ε-amino hexanoic acid, δ-amino valeric acid, 2,3-diaminobutyric acid and mixtures thereof.

Other amino acid residues that are useful for making the peptides and peptide analogues described herein can be found, e.g., in Fasman, 1989, CRC Practical Handbook of Biochemistry and Molecular Biology, CRC Press, Inc., and the references cited therein.

The present invention additionally encompasses an isostere of a peptide described herein. The term "isostere" as used herein is intended to include a chemical structure that can be substituted for a second chemical structure because the steric conformation of the first structure fits a binding site specific for the second structure. The term specifically includes peptide back-bone modifications (i.e., amide bond mimetics) known to those skilled in the art. Such modifications include modifications of the amide nitrogen, the α-carbon, amide carbonyl, complete replacement of the amide bond, extensions, deletions or backbone crosslinks. Several peptide backbone modifications are known, including ψ[$CH_2S$], ψ[$CH_2NH$], ψ[$CSNH_2$], ψ[NHCO], ψ[$COCH_2$], and ψ[(E) or (Z) CH=CH]. In the nomenclature used above, ψ indicates the absence of an amide bond. The structure that replaces the amide group is specified within the brackets.

Other modifications include, for example, an N-alkyl (or aryl) substitution (ψ[CONR]), or backbone crosslinking to construct lactams and other cyclic structures. Other derivatives of the modulator compounds of the invention include C-terminal hydroxymethyl derivatives, O-modified derivatives (e.g., C-terminal hydroxymethyl benzyl ether), N-terminally modified derivatives including substituted amides such as alkylamides and hydrazides.

In another example, a peptide analogue is a retro-peptide analogue (see, for example, Goodman et al., *Accounts of Chemical Research*, 12:1-7, 1979). A retro-peptide analogue comprises a reversed amino acid sequence of a peptide inhibitor described herein. For example, a retro-peptide analogue of a peptide inhibitor comprises a reversed amino acid sequence of a sequence set forth in any one of SEQ ID NOs: 26-72, 121-124, 129, 131 or 163. For example, a retro-peptide analogue of a peptide inhibitor comprises a reversed amino acid sequence of a sequence set forth in any one of SEQ ID NOs: 26-72 or 163. Optionally, the peptide analog comprises an additional feature, such as, for example, a protein transduction domain, which may also be a retro-peptide.

In a further example, an analogue of a peptide described herein is a retro-inverso peptide (as described, for example, in Sela and Zisman, *FASEB J.* 11:449, 1997). Evolution has ensured the almost exclusive occurrence of L-amino acids in naturally occurring proteins. As a consequence, virtually all proteases cleave peptide bonds between adjacent L-amino acids. Accordingly, artificial proteins or peptides composed of D-amino acids are preferably resistant to proteolytic breakdown. Retro-inverso peptide analogues are isomers of linear peptides in which the direction of the amino acid sequence is reversed (retro) and the chirality, D- or L-, of one or more amino acids therein is inverted (inverso) e.g., using D-amino acids rather than L-amino acids, e.g., Jameson et al., *Nature*, 368, 744-746 (1994); Brady et al., *Nature*, 368, 692-693 (1994). The net result of combining D-enantiomers and reverse synthesis is that the positions of carbonyl and amino groups in each amide bond are exchanged, while the position of the side-chain groups at each alpha carbon is preserved. An advantage of retro-inverso peptides is their enhanced activity in vivo due to improved resistance to proteolytic degradation, i.e., the peptide has enhanced stability. (e.g., Chorev et al., *Trends Biotech.* 13, 438-445, 1995).

Retro-inverso peptide analogues may be complete or partial. Complete retro-inverso peptides are those in which a complete sequence of a peptide described herein is reversed and the chirality of each amino acid in a sequence is inverted, other than glycine, because glycine does not have a chiral analogue. Partial retro-inverso peptide analogues are those in which only some of the peptide bonds are reversed and the chirality of only those amino acid residues in the reversed portion is inverted. For example, one or two or three or four or five or six or seven or eight or nine or ten or eleven or twelve or thirteen or fourteen or fifteen or sixteen or seventeen or eighteen or nineteen or twenty or twenty one or twenty two or twenty three or twenty four or twenty five or twenty six or twenty seven or twenty eight or twenty nine or thirty or thirty one or thirty two or thirty three or thirty four or thirty five or thirty six or thirty seven or thirty eight amino acid residues are D-amino acids. The present invention clearly encompasses both partial and complete retro-inverso peptide analogues. For example, the present invention provides a retro-inverso peptide analogue comprising an amino acid sequence set forth in any one of SEQ ID NOs: 73-120, 125-128, 130, 164 or 165. For example, a retro-inverso peptide analogue comprises an amino acid sequence set forth in any one of SEQ ID NOs: 73-120, 164 or 165. In this respect, such a retroinverso peptide analogue may optionally include an additional component, such as, for example, a protein transduction domain, which may also be retroinverted. For example, a retro-inverso peptide analog comprises an amino acid sequence set forth in any one of SEQ ID NOs: 74, 76, 78, 80, 82, 84, 86, 88, 90, 92, 94, 96, 98, 100, 101, 104, 106, 108, 110, 112, 114, 116, 118 or 120.

As will be apparent to the skilled artisan based on the foregoing description, the present invention contemplates a peptide AP-1 signaling inhibitor selected individually or collectively from the group consisting of:
(i) a peptide comprising an amino acid sequence set forth in any on of SEQ ID NOs: 26-72, 121-124, 129, 131 or 163;
(ii) a peptide encoded by a nucleic acid comprising a sequence set forth in any one of SEQ ID NOs: 1-25;
(iii) the peptide of (i) or (ii) additionally comprising a protein transduction domain, e.g., a HIV tat basic region (e.g., comprising a sequence set forth in any one of SEQ ID NOs: 137-144) or a retroinverted analogue thereof (e.g., comprising a sequence set forth in any one of SEQ ID NOs: 145-152);
(iii) an analogue of any one of (i) to (iii) selected from the group consisting of (a) the sequence of any one of (i) to (iii) comprising one or more non-naturally-occurring amino acids; (b) the sequence of any one of (i) to (iii) comprising one or more non-naturally-occurring amino acid analogues; (c) an isostere of any one of (i) to (iii); (d) a retro peptide analogue of any one of (i) to (iii); and (e) a retro-inverted peptide analogue of any one of (i) to (iii).
(iv) a retroinverted peptide analogue comprising an amino acid sequence set forth in any one of SEQ ID NOs: 73-119, 125-127, 130, 164 or 165.

In one example, an analog peptide inhibitor of AP-1 signaling comprises an amino acid sequence set forth in SEQ ID NO: 104.

The present invention also provides a topical composition comprising an AP-1 signaling peptide inhibitor or an analog thereof selected individually or collectively from the group consisting of:
(i) a functional fragment of a peptide comprising an amino acid sequence set forth in any on of SEQ ID NOs: 26-72, 121-124, 129, 131 or 163;
(ii) a functional fragment of a peptide encoded by a nucleic acid comprising a sequence set forth in any one of SEQ ID NOs: 1-25;
(iii) the peptide of (i) or (ii) additionally comprising a protein transduction domain, e.g., a HIV tat basic region (e.g., comprising a sequence set forth in any one of SEQ ID NOs: 137-144) or a retroinverted analogue thereof (e.g., comprising a sequence set forth in any one of SEQ ID NOs: 145-152); (iii) an analogue of any one of (i) to (iii) selected from the group consisting of (a) the sequence of any one of (i) to (iii) comprising one or more non-naturally-occurring amino acids; (b) the sequence of any one of (i) to (iii) comprising one or more non-naturally-occurring amino acid analogues; (c) an isostere of any one of (i) to (iii); (d) a retro-peptide analogue of any one of (i) to (iii); and (e) a retro-inverted peptide analogue of any one of (i) to (iii).
(iv) a functional fragment of a retroinverted peptide analogue comprising an amino acid sequence set forth in any one of SEQ ID NOs: 73-119, 125-127, 130, 164 or 165.

As used herein the term "functional fragment" shall be taken to mean a fragment of a peptide or analog thereof that is capable of reducing or preventing apoptosis and/or necrosis induced by dermal wounding and/or to induce and/or enhance proliferation of a cell. In this respect, the activity of a functional fragment need not be the same as that of the peptide or analog from which the fragment is derived. For example, the fragment may have enhanced or reduced activity compared to the peptide or analog from which it is derived.

Peptide Synthesis

A peptide or an analog or derivative thereof is preferably synthesized using a chemical method known to the skilled artisan. For example, synthetic peptides are prepared using known techniques of solid phase, liquid phase, or peptide condensation, or any combination thereof, and can include natural and/or unnatural amino acids Amino acids used for peptide synthesis may be standard Boc (Nα-amino protected Nα-t-butyloxycarbonyl) amino acid resin with the deprotecting, neutralization, coupling and wash protocols of the original solid phase procedure of Merrifield, J. Am. Chem. Soc., 85:2149-2154, 1963, or the base-labile Na-amino protected 9-fluorenylmethoxycarbonyl (Fmoc) amino acids described by Carpino and Han, J. Org. Chem., 37:3403-3409, 1972. Both Fmoc and Boc Nα-amino protected amino acids can be obtained from various commercial sources, such as, for example, Fluka, Bachem, Advanced Chemtech, Sigma, Cambridge Research Biochemical, Bachem, or Peninsula Labs.

Generally, chemical synthesis methods comprise the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. See, e.g., J. M. Stewart and J. D. Young, Solid Phase Peptide Synthesis (Pierce Chemical Co., Rockford, Ill. 1984) and G. Barany and R. B. Merrifield, The Peptides: Analysis, Synthesis, Biology, editors E. Gross and J. Meienhofer, Vol. 2, (Academic Press, New York, 1980), pp. 3-254, for solid phase peptide synthesis techniques; and M. Bodansky, Principles of Peptide Synthesis, (Springer-Verlag, Berlin 1984) and E. Gross and J. Meienhofer, Eds., The Peptides: Analysis. Synthesis. Biology, Vol. 1, for classical solution synthesis. These methods are suitable for synthesis of a peptide of the present invention or an analog or derivative thereof.

Typical protecting groups include t-butyloxycarbonyl (Boc), 9-fluorenylmethoxycarbonyl (Fmoc) benzyloxycarbonyl (Cbz); p-toluenesulfonyl (Tx); 2,4-dinitrophenyl; benzyl (Bzl); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like.

Typical solid supports are cross-linked polymeric supports. These can include divinylbenzene cross-linked-styrene-based polymers, for example, divinylbenzene-hydroxymethylstyrene copolymers, divinylbenzene-chloromethylstyrene copolymers and divinylbenzene-benzhydrylaminopolystyrene copolymers.

A peptide, analogue or derivative as described herein can also be chemically prepared by other methods such as by the method of simultaneous multiple peptide synthesis. See, e.g., Houghten Proc. Natl. Acad. Sci. USA 82: 5131-5135, 1985 or U.S. Pat. No. 4,631,211.

As will be apparent to the skilled artisan based on the description herein, an analogue or derivative of a peptide of the invention may comprise D-amino acids, a combination of D- and L-amino acids, and various unnatural amino acids (e.g., α-methyl amino acids, Cα-methyl amino acids, and Nα-methyl amino acids, etc) to convey special properties. Synthetic amino acids include ornithine for lysine, fluorophenylalanine for phenylalanine, and norleucine for leucine or isoleucine. Methods for the synthesis of such peptides will be apparent to the skilled artisan based on the foregoing description.

Recombinant Peptide Production

Alternatively, or in addition, a peptide or analogue or derivative thereof or fusion protein comprising same is produced as a recombinant protein. To facilitate the production of a recombinant peptide or fusion protein nucleic acid encoding same is preferably isolated or synthesized. Typically the nucleic acid encoding the recombinant protein is/are isolated using a known method, such as, for example, amplification (e.g., using PCR or splice overlap extension) or isolated from nucleic acid from an organism using one or more restriction enzymes or isolated from a library of nucleic acids. Methods for such isolation will be apparent to the ordinary skilled artisan and/or described in Ausubel et al (In: Current Protocols in Molecular Biology. Wiley Interscience, ISBN 047 150338, 1987), Sambrook et al (In: Molecular Cloning: Molecular Cloning: A Laboratory Manual, Cold Spring Harbor Laboratories, New York, Third Edition 2001).

For expressing protein by recombinant means, a protein-encoding nucleic acid is placed in operable connection with a promoter or other regulatory sequence capable of regulating expression in a cell-free system or cellular system. For example, nucleic acid comprising a sequence that encodes a peptide is placed in operable connection with a suitable promoter and maintained in a suitable cell for a time and under conditions sufficient for expression to occur. Nucleic acid encoding a peptide inhibitor of AP-1 signaling is described herein or is derived from the publicly available amino acid sequence.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid (e.g., a transgene), e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid (e.g., a transgene and/or a selectable marker gene and/or a detectable marker gene) to which it is operably linked. Preferred promoters can contain additional copies of one or more specific regulatory elements to further enhance expression and/or alter the spatial expression and/or temporal expression of said nucleic acid.

As used herein, the term "in operable connection with", "in connection with" or "operably linked to" means positioning a promoter relative to a nucleic acid (e.g., a transgene) such that expression of the nucleic acid is controlled by the promoter. For example, a promoter is generally positioned 5' (upstream) to the nucleic acid, the expression of which it controls. To construct heterologous promoter/nucleic acid combinations (e.g., promoter/nucleic acid encoding a peptide), it is generally preferred to position the promoter at a distance from the gene transcription start site that is approximately the same as the distance between that promoter and the nucleic acid it controls in its natural setting, i.e., the gene from which the promoter is derived. As is known in the art, some variation in this distance can be accommodated without loss of promoter function.

Should it be preferred that a peptide or fusion protein of the invention is expressed in vitro a suitable promoter includes, but is not limited to a T3 or a T7 bacteriophage promoter (Hanes and Plückthun *Proc. Natl. Acad. Sci. USA*, 94 4937-4942 1997).

Typical expression vectors for in vitro expression or cell-free expression have been described and include, but are not limited to the TNT T7 and TNT T3 systems (Promega), the pEXP1-DEST and pEXP2-DEST vectors (Invitrogen).

Typical promoters suitable for expression in bacterial cells include, but are not limited to, the lacz promoter, the Ipp promoter, temperature-sensitive λL or λR promoters, T7 promoter, T3 promoter, SP6 promoter or semi-artificial promoters such as the IPTG-inducible tac promoter or lacUV5 promoter. A number of other gene construct systems for expressing the nucleic acid fragment of the invention in bacterial cells are well-known in the art and are described for example, in Ausubel et al (In: Current Protocols in Molecular Biology. Wiley Interscience, ISBN 047 150338, 1987), U.S. Pat. No. 5,763,239 (Diversa Corporation) and Sambrook et al (In: Molecular Cloning: Molecular Cloning: A Laboratory Manual, Cold Spring Harbor Laboratories, New York, Third Edition 2001).

Numerous expression vectors for expression of recombinant polypeptides in bacterial cells and efficient ribosome binding sites have been described, and include, for example, PKC30 (Shimatake and Rosenberg, *Nature* 292, 128, 1981); pKK173-3 (Amann and Brosius, *Gene* 40, 183, 1985), pET-3 (Studier and Moffat, *J. Mol. Biol.* 189, 113, 1986); the pCR vector suite (Invitrogen), pGEM-T Easy vectors (Promega), the pL expression vector suite (Invitrogen) the pBAD/TOPO or pBAD/thio—TOPO series of vectors containing an arabinose-inducible promoter (Invitrogen, Carlsbad, Calif.), the latter of which is designed to also produce fusion proteins with a Trx loop for conformational constraint of the expressed protein; the pFLEX series of expression vectors (Pfizer Inc., CT, USA); the pQE series of expression vectors (QIAGEN, CA, USA), or the pL series of expression vectors (Invitrogen), amongst others.

Typical promoters suitable for expression in viruses of eukaryotic cells and eukaryotic cells include the SV40 late promoter, SV40 early promoter and cytomegalovirus (CMV) promoter, CMV IE (cytomegalovirus immediate early) promoter amongst others. Preferred vectors for expression in mammalian cells (e.g., 293, COS, CHO, 10T cells, 293T cells) include, but are not limited to, the pcDNA vector suite supplied by Invitrogen, in particular pcDNA 3.1 myc-His-tag comprising the CMV promoter and encoding a C-terminal 6×His and MYC tag; and the retrovirus vector pSRatkneo (Muller et al., *Mol. Cell. Biol.*, 11, 1785, 1991).

A wide range of additional host/vector systems suitable for expressing a peptide or fusion protein of the present invention are available publicly, and described, for example, in Sambrook et al (In: Molecular cloning, A laboratory manual, second edition, Cold Spring Harbor Laboratory, Cold Spring Harbor, N.Y., 1989).

Means for introducing the isolated nucleic acid molecule or a gene construct comprising same into a cell for expression are well-known to those skilled in the art. The technique used for a given organism depends on the known successful techniques. Means for introducing recombinant DNA into cells include microinjection, transfection mediated by DEAE-dextran, transfection mediated by liposomes such as by using lipofectamine (Gibco, Md., USA) and/or cellfectin (Gibco, Md., USA), PEG-mediated DNA uptake, electroporation and microparticle bombardment such as by using DNA-coated tungsten or gold particles (Agracetus Inc., WI, USA) amongst others.

3. Antibody Inhibitors

The present invention also contemplates an antibody AP-1 signaling inhibitor. For example, Estus et al., *J. Cell. Biol.*, 127: 1717-1727, 1994 describe antibodies against c-Jun or Fos that are capable of inhibiting AP-1 signaling.

Methods for producing additional antibodies will be apparent to the skilled artisan. For example, a monoclonal antibody against a protein involved in or necessary for AP-1 signaling (e.g., JNK or c-Jun, or c-Fos or Cdc42 or Pak1 or Rac1) is produced by immunizing an animal, e.g., a mouse, with said protein or an immunogenic fragment thereof. Optionally, the protein or fragment is injected in the presence of an adjuvant, such as, for example Freund's complete or incomplete adjuvant, lysolecithin and/or dinitrophenol to enhance the immune response to the immunogen. Spleen cells are then obtained from the immunized animal. The spleen cells are then immortalized by, for example, fusion with a myeloma cell fusion partner, preferably one that is syngenic with the immunized animal. A variety of fusion techniques may be employed, for example, the spleen cells and myeloma cells may be combined with a nonionic detergent or electrofused and then grown in a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and growth media in which the cells have been grown is tested for the presence of binding activity against the polypeptide (immunogen). Hybridomas having high reactivity and specificity are preferred.

Monoclonal antibodies are isolated from the supernatants of growing hybridoma colonies using methods such as, for example, affinity purification using the immunogen to isolate an antibody capable of binding thereto. In addition, various techniques may be employed to enhance the yield, such as injection of the hybridoma cell line into the peritoneal cavity of a suitable vertebrate host, such as a mouse. Monoclonal antibodies are then harvested from the ascites fluid or the blood of such an animal subject. Contaminants are removed from the antibodies by conventional techniques, such as chromatography, gel filtration, precipitation, and/or extraction.

To ensure that the antibody is capable of entering a cell and inhibiting or reducing AP-1 signaling an antibody fragment or recombinant antibody may be produced and conjugated to a protein transduction domain, for example, a protein transduction domain described herein.

4. Small Molecule Inhibitors

In a still further example of the invention, an AP-1 signaling inhibitor is a small molecule. For example, CEP-1347 (or 3,9bis[(ethylthio)methyl]-K252a) is capable of inhibiting AP-1 signaling (Kaneko et al., *J. Med. Chem.*, 40: 1863-1869, 1997).

Alternatively, the compound SP600125 is an anthrapyrazolone ATP-competitive inhibitor (anthra[1,9-cd]pyrazole-6-(2H)-one) capable directly interacting with JNK and inhibiting AP-1 signaling (Bennet et al., *Proc. Natl. Acad. Sci. USA*, 98: 13681-13686, 2001.

Alternatively, a natural product such as, for example, curcumin, dihydroguaiaretic acid or an anthraquinone derivative are capable of inhibiting AP-1 signaling by inhibiting the binding of AP-1 to an AP-1 binding site (Hahm et al., *Cancer Lett.*, 184: 89-96, 2002; Park et al., *Cancer Lett*, 127: 23-28, 2998; and Goto et al., *J. Antibiot.*, 51: 539-544, 1998).

Tsuchida et al., *J. Medicinal Chem.*, 49:80-91, 2006, describes a number of small molecule inhibitors of AP-1 signaling based on the structure of a peptide inhibitor. These compounds include (R)-4-(4-methylpentanoyl)-8-(4-methylpentylidene)-1-thia-4-azaspiro[4.5]decane-3-carboxylic acid; (R)-8-(3-methylbutylidene)-4-(5-methylhexanoyl)-1-thia-4-azaspiro[4.5]decane-3-carboxylic acid; and 3-[2-isobutoxy-5-(4-isobutoxybenzoyl)phenyl]propionic acid. Tsuchida et al., additionally describes methods for identifying additional AP-1 signaling inhibitors.

Alternatively, a suitable small molecule inhibitor is identified from a library of small molecules. Techniques for synthesizing small organic compounds will vary considerably depending upon the compound, however such methods will be well known to those skilled in the art. In one embodiment, informatics is used to select suitable chemical building blocks from known compounds, for producing a combinatorial library. For example, QSAR (Quantitative Structure Activity Relationship) modeling approach uses linear regressions or regression trees of compound structures to determine suitability. The software of the Chemical Computing Group, Inc. (Montreal, Canada) uses high-throughput screening experimental data on active as well as inactive compounds, to create a probabilistic QSAR model, which is subsequently used to select lead compounds. The Binary QSAR method is based upon three characteristic properties of compounds that form a "descriptor" of the likelihood that a particular compound will or will not perform a required function: partial charge, molar refractivity (bonding interactions), and logP (lipophilicity of molecule). Each atom has a surface area in the molecule and it has these three properties associated with it. All atoms of a compound having a partial charge in a certain range are determined and the surface areas (Van der Walls Surface Area descriptor) are summed. The binary QSAR models are then used to make activity models or ADMET models, which are used to build a combinatorial library. Accordingly, lead compounds identified in initial screens, can be used to expand the list of compounds being screened to thereby identify highly active compounds.

Assays to Identify Inhibitors

In addition to providing a variety of AP-1 signaling inhibitors, the present invention contemplates identification of new inhibitory compounds. Suitable compounds for testing will be apparent to the skilled artisan based on the foregoing description.

The ability of a compound to inhibit AP-1 signaling is then determined by any of a variety of assays.

For example, Tsuchida et al., supra, describe an enzyme linked immunoassay (ELISA) that uses a double stranded oligonucleotide comprising an AP-1 binding site and an AP-1 bZIP peptide, The AP-1 bZIP peptide is coated onto a microtitre plate and blocked. Labeled oligonucleotide (e.g., digoxigenin labeled oligonucleotide) is added to the microtitre plate in the presence or absence of a test compound. Following washing to remove unbound oligonucleotide, the amount of label bound to the AP-1 peptide is determined. A compound that reduces the level of oligonucleotide bound to the peptide is considered to inhibit AP-1 signaling by virtue of inhibiting AP-1 transcriptional regulation.

An additional assay to determine an AP-1 signaling inhibitor comprises producing or obtaining a cell comprising a reporter gene operably connected to a promoter comprising an AP-1 binding site. The cell is then contacted with a test compound for a time and under conditions sufficient to inhibit or reduce AP-1 signaling and the level of reporter gene expression determined. A compound that reduces reporter gene expression is considered to inhibit or reduce AP-1 signaling.

Alternatively, a reverse hybrid assay is performed to identify an AP-1 signaling inhibitor. For example, a reverse two-hybrid assay is performed to identify a compound that inhibits interaction of two proteins, the interaction of which is required for AP-1 signaling. For example, a compound is identified that inhibits or reduces the interaction between JNK and c-Jun, a MAP kinase kinase kinase and JNK, JNK and HP, or any of the proteins that interact to form AP-1. For example, an assay is performed to identify a compound that inhibits c-Jun dimerization. Reverse hybrid methods will be apparent to the skilled artisan and/or described in Watt et al. (U.S. Ser. No. 09/227,652) or Erickson et al. (WO95/26400).

In one example of the invention, an AP-1 signaling inhibitor is also capable of inhibiting apoptosis and/or necrosis. Methods for determining a compound that inhibits apoptosis will be apparent to the skilled artisan. For example, APOPTEST (available from Immunotech) stains cells early in apoptosis, and does not require fixation of the cell sample (Martin et al., 1994). This method utilizes an annexin V antibody to detect cell membrane re-configuration that is characteristic of cells undergoing apoptosis. Apoptotic cells stained in this manner can then sorted either by fluorescence activated cell sorting (FACS), ELISA or by adhesion and panning using immobilized annexin V antibodies.

Alternatively, a terminal deoxynucleotidyl transferase-mediated biotinylated UTP nick end-labeling (TUNEL) assay is used to determine the level of cell death. The TUNEL assay uses the enzyme terminal deoxynucleotidyl transferase to label 3'-OH DNA ends, generated during apoptosis, with biotinylated nucleotides. The biotinylated nucleotides are then detected by using streptavidin conjugated to a detectable marker. Kits for TUNEL staining are available from, for example, Intergen Company, Purchase, N.Y.

Alternatively, or in addition, an activated caspase, such as, for example, Caspase 3 is detected. Several caspases are effectors of apoptosis and, as a consequence, are only activated to significant levels in a cell undergoing programmed cell death. Kits for detection of an activated caspase are available from, for example, Promega Corporation, Madison Wis., USA. Such assays are useful for both immunocytochemical or flow cytometric analysis of cell death.

Methods for detecting necrosis or determining the level of necrosis, e.g., in a sample comprising cells are known in the art and/or described, for example, in Lemaire et al., *Cell Death and Differentiation*, 6: 813-820, 1999, In a further example of the invention, an AP-1 signaling inhibitor is also capable of inducing and/or enhancing proliferation of a cell. Methods for determining a compound that induces or enhances proliferation will be apparent to the skilled artisan. For example, incorporation of $^3$H-thymidine or $^{14}$C-thymidine into DNA as it is synthesized is an assay for DNA synthesis associated with cell division. In such an assay, a cell is incubated in the presence of labeled thymidine for a time and under condition sufficient for cell division to occur. Following washing to remove any unincorporated thymidine, the amount of label (e.g. the radioactive label) in the sample is detected, e.g., using a scintilation counter. The amount of label detected is indicative of the level of proliferation of one or more cells in the sample. Assays for the detection of thymidine incorporation into a live cell are available from, for example, Amersham Pharmacia Biotech.

In another embodiment, cellular proliferation is measured using a 3-(4,5-dimethylthiazolyl-2)-2,5-diphenyltetrazolium bromide (MTT) assay. In such an assay, MTT is contacted to live cells for a time and under conditions sufficient for cellular proliferation to occur. The yellow tetrazolium MTT is reduced by metabolically active cells, in part by the action of dehydrogenase enzymes, to generate reducing equivalents such as NADH and NADPH. The resulting intracellular purple formazan is then solubilized and quantified by spectrophotometric means. Assay kits for MTT assays are available from, for example, American Type Culture Collection.

Alternative assays for determining cellular proliferation, include, for example, measurement of DNA synthesis by BrdU incorporation (by ELISA or immunohistochemistry, kits available from Amersham Pharmacia Biotech), expression of proliferating cell nuclear antigen (PCNA) (by ELISA, FACS or immunohistochemistry, kits available from Oncogene Research Products) or a Hoechst cell proliferation assay that detects DNA synthesis (available from Trevigen Inc.).

Alternatively, the growth rate of the cell is determined, for example, manually, by, for example observing or measuring the size of a colony of cells over a period of time or, alternatively or in addition counting the number of cells over a period of time.

In an additional or alternative embodiment of the invention, a compound is screened to identify a compound suitable for the treatment of a dermal wound (e.g., a burn). For example, a wound is induced in a subject and a compound is applied topically to the wound. The level of apoptosis and/or necrosis in the wound is then determined, e.g., using a method described herein, and a compound that reduces the level of apoptosis and/or necrosis in a wound to which it is applied compared to a wound to which it is not applied is selected.

Alternatively, or in addition, the level of wound healing is determined. For example, the rate of re-epithelialization of a wound is determined by measuring the distance between edges of a wound. A compound that enhances the rate at which a wound heals is then selected. Alternatively, cells (e.g., a tissue section), is analyzed (e.g., by immunohistochemical staining, e.g., with an anti-proliferating cell nuclear antigen antibody) to determine the number of cells proliferating in the wound. A compound that enhances or increases the number of cells proliferating, e.g., the number of epithelial cells proliferating, e.g., the number of keratinocyte cells proliferating in the wound and/or adjacent to the wound is then selected.

Additional methods for determining a compound that enhances wound healing when topically applied will be apparent to the skilled artisan.

Carriers or Excipients for Dermal Application

A topical composition of the invention as described herein according to any embodiment comprises an AP-1 signaling inhibitor and a carrier or excipient suitable for dermal application.

The term "carrier or excipient" as used herein, refers to a carrier or excipient that is conventionally used in the art to facilitate the storage, administration, and/or the biological activity of an active compound. A carrier may also reduce any undesirable side effects of the active compound. A suitable carrier is, for example, stable, e.g., incapable of reacting with other ingredients in the formulation. In one example, the carrier does not produce significant local or systemic adverse effect in recipients at the dosages and concentrations employed for treatment. Such carriers and excipients are generally known in the art. Suitable carriers for this invention include those conventionally used, e.g., water, saline, aqueous dextrose, and glycols are preferred liquid carriers, particularly (when isotonic) for solutions. Suitable pharmaceutical carriers and excipients include starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like.

The skilled artisan will be aware of a suitable carrier or excipient. For example, a carrier or excipient does not inhibit the anti-apoptotic activity and/or anti-necrotic activity and/or mitogenic activity of an AP-1 signaling inhibitor. In one example, the carrier or excipient permits the inhibitor to inhibit or reduce apoptosis and/or necrosis in a wound and/or induce proliferation of a cell in a wound. For example, the carrier or excipient provides a buffering activity to maintain the compound at a suitable pH to thereby exert its biological activity, e.g., the carrier or excipient is phosphate buffered saline (PBS). PBS represents an attractive carrier or excipient because it interacts with compounds minimally and permits rapid release of the compound into a wound. In such a case, the topical composition of the invention may be produced as a liquid or direct application to a wound, e.g., as a spray or a wash. Alternatively, or in addition, the topical composition may be instilled or introduced into a suitable wound dressing.

Suitable carriers for topical application of a compound are known in the art and include, for example, methyl cellulose (e.g., 3% methylcellulose; Beck et al., *Growth Factors*, 3: 267, 1990), silver sulfadiazene cream (Schultz et al., *Science*, 235: 350, 1985), multilamellar lecithin liposomes (Brown et al., *Ann Surg.*, 208: 788, 1988) or hyaluronic acid (Curtsinger et al., *Surg. Gynecol. Obstet.*, 168: 517, 1989).

In one example, the carrier is a co-polymer. For example, Puolakkainen et al., *J. urg. Res.*, 58: 321-329 describes a variety of carriers suitable for delivering a compound to the site of a wound. For example, Puolakkainen et al., describe a poly(ethylene oxide)-poly(propylene oxide) block copolymer designated Pluronic F-127. Pluronic F-127 has been used as a carrier for a variety of peptides and proteins in addition to nucleic acid based compounds. This carrier exhibits thermoreversability, relative inertness toward protein and nucleic acid and low toxicity.

In another example, the carrier is a paste. For example, DuoDERM is a hydroactive paste, which creates a moist wound-healing environment that has been suggested to enhance the repair process in full-thickness wounds. DuoDERM comprises sodium carboxymethylcellulose, gelatin, pectin and polyisobutylene. This carrier protects the wound bed, facilitates cell migration into the wound and prevents a wound dressing from adhering to new granulation tissue upon removal (Alvarez et al., *J. Surg. Res.*, 35: 142, 1983).

In a further example, the carrier is a hydrogel. For example, biopol hydrogel is a poly(ethylene oxide) cross-linked hydrogel that interacts with aqueous solutions and swells to an equilibrium value, retaining a significant portion of the aqueous solution within its structure. Hydrogels have been shown to be suitable for delivery of a number of compounds, including proteins or peptides (Pitt et al., *Int. J. Pharm.*, 59: 173, 1990.

Additional carriers or excipients for dermal delivery of a compound are described in, for example, Kikwai et al., *AAPS PharmSciTech.*, 6: E565-72, 2005. For example, a suitable carrier is a hydroxypropyl methylcellulose (HPMC) or a hydroxypropyl cellulose (HPC). Such carriers may be formulated as a liquid, a gel or a cream. Optionally, the carrier additionally comprises n-methyl-2-pyrrolidine (NMP) to enhance uptake of a topical composition therein. Methods for producing topical compositions comprising such carriers or excipients will be apparent to the skilled artisan and/or described in, for example, Kikwai et al., supra.

Alternatively, or in addition, an AP-1 signaling inhibitor is conjugated to or mixed with a peptide capable of transdermal delivery of a compound. For example, Prausnitz *Nature Biotech.*, 4: 416-417, 2006 described a peptide comprising a sequence set forth in SEQ ID NO: 158 capable of delivering a compound across the skin of a subject. In this case, the peptide appeared to make use of a transfollicular route to deliver a compound across the skin of a subject.

A topical composition according to any embodiment described herein can be subjected to conventional pharmaceutical expedients, such as sterilization, and can contain a conventional pharmaceutical additive, such as a preservative and/or a stabilizing agent and/or a wetting agent and/or an emulsifying agent and/or a salt for adjusting osmotic pressure and/or a buffer and/or other additives known in the art. Other acceptable components in the topical composition of the invention include, but are not limited to, isotonicity-modifying agents such as water and/or saline and/or a buffer including phosphate, citrate, succinate, acetic acid, or other organic acids or their salts.

In an example, a topical composition of the invention also includes one or more stabilizers, reducing agents, anti-oxidants and/or anti-oxidant chelating agents. The use of buffers, stabilizers, reducing agents, anti-oxidants and chelating agents in the preparation of compositions, is known in the art and described, for example, in Wang et al. *J. Parent. Drug Assn.* 34:452-462, 1980; Wang et al. *J. Parent. Sci. Tech.* 42:S4-S26 (Supplement), 1988. Suitable buffers include acetate, adipate, benzoate, Citrate, lactate, maleate, phosphate, tartarate, borate, tri(hydroxymethyl aminomethane), succinate, glycine, histidine, the salts of various amino acids, or the like, or combinations thereof. Suitable salts and isotonicifiers include sodium chloride, dextrose, mannitol, sucrose, trehalose, or the like. Where the carrier is a liquid, it is preferred that the carrier is hypotonic or isotonic with oral, conjunctival, or dermal fluids and has a pH within the range of 4.5-8.5. Where the carrier is in powdered form, it is preferred that the carrier is also within an acceptable non-toxic pH range.

In another example, a topical composition as described herein according to any embodiment additionally comprises a compound that enhances or facilitates uptake of a compound into and/or through skin of a subject. Suitable dermal permeation enhancers are, for example, a lipid disrupting agent (LDA), a solubility enhancer, or a surfactant.

LDAs are typically fatty acid-like molecules proposed to fluidize lipids in the human skin membrane. Suitable LDAs are described, for example, in Francoeur et al., *Pharm. Res.*, 7: 621-627, 1990 and U.S. Pat. No. 5,503,843. For example, a suitable LDA is a long hydrocarbon chain with a cis-unsaturated carbon-carbon double bond. These molecules have been shown to increase the fluidity of the lipids, thereby increasing drug transport. For example, oleic acid, oleyl alcohol, decanoic acid, and butene diol are useful LDAs.

Solubility enhancers act by increasing the maximum concentration of drug in a composition, thus creating a larger concentration gradient for diffusion. For example, a lipophilic vehicle isopropyl myristate (IPM) or an organic solvent ethanol or N-methyl pyrrolidone (NMP) are suitable solubility enhancers (Liu et al., *Pharm. Res.* 8: 938-944, 1991; and Yoneto et al., *J. Pharm. Sci.* 84: 853-860, 1995).

Surfactants are amphiphilic molecules capable of interacting with the polar and lipid groups in the skin. These molecules have affinity to both hydrophilic and hydrophobic groups, which facilitate in traversing complex regions of the dermis. Suitable surfactants include, for example, an anionic surfactant lauryl sulfate (SDS) or a nonionic surfactant polysorbate 80 (Tween 80). Suitable surfactants are described, for example, in Sarpotdar et al., *J. Pharm. Sci.* 75: 176-181, 1986)

In another example, the topical composition described herein according to any embodiment is a microemulsion. Microemulsion systems are useful for enhancing transdermal delivery of a compound. Characteristics of such microemulsion systems are sub-micron droplet size, thermodynamic stability, optical transparency, and solubility of both hydrophilic and hydrophobic components. Microemulsion systems have been shown to be useful for transdermal delivery of compounds and to exhibit improved solubility of hydrophobic drugs as well as sustained release profiles (Lawrence, et. al. *Int. Journal of Pharmaceutics* 111: 63-72, 1998).

In another example, a topical composition as described herein according to any embodiment additionally comprises a liposome carrier or excipient to facilitate uptake of an inhibitor into a cell. Liposomes are considered to interact with a cell by stable absorption, endocytosis, lipid transfer, and/or fusion (Egerdie et al., *J. Urol.* 142:390, 1989). For example, liposomes comprise molecular films, which fuse with cells and provide optimal conditions for wound healing (K. Reimer et al., *Dermatology* 195(suppl. 2):93, 1999). Generally, liposomes have low antigenicity and can be used to encapsulate and deliver components that cause undesirable immune responses in patients (Natsume et al., *Jpn. J. Cancer Res.* 91:363-367, 2000)

For example, anionic or neutral liposomes often possess excellent colloidal stability, since substantially no aggregation occurs between the carrier and the environment. Consequently their biodistribution is excellent, and their potential for irritation and cytotoxicity is low.

Alternatively, cationic liposomal systems, e.g. as described in Mauer et al., *Molecular Membrane Biology*, 16: 129-140, 1999 or Maeidan et al., *BBA* 1464: 251-261, 2000 are useful for delivering compounds into a cell. Such cationic systems provide high loading efficiencies. Moreover, PEGylated cationic liposomes show enhanced circulation times in vivo (Semple *BBA* 1510, 152-166, 2001).

Amphoteric liposomes are a recently described class of liposomes having an anionic or neutral charge at pH 7.4 and a cationic charge at pH 4. Examples of these liposomes are described, for example, in WO 02/066490, WO 02/066012 and WO 03/070735. Amphoteric liposomes have been found to have a good biodistribution and to be well tolerated in animals and they can encapsulate nucleic acid molecules with high efficiency.

U.S. Ser. No. 09/738,046 and U.S. Ser. No. 10/218,797 describe liposomes suitable for the delivery of peptides or proteins into a cell.

Additional Components

In another example of the invention, a topical composition as described herein according to any embodiment comprises an additional component or compound. For example, the topical composition comprises a compound associated with increased dermal wound healing. For example, the topical composition comprises a growth factor, such as, for example, transforming growth factor β and/or platelet derived growth factor and/or nerve growth factor and/or heparin binding epidermal growth factor and/or epidermal growth factor and/or keratinocyte growth factor and/or platelet derived activating factor and/or platelet derived epithelial growth factor and/or a fibroblast growth factor an/or a keratinocyte growth factor.

For example, Puolakkainen et al., *J. Surg. Res.*, 58: 321-329, 1995 describe topical formulations comprising transforming growth factor β; compositions comprising platelet derived growth factor have been described by Lepisto et al., *J. Surg. Res.*, 53: 596-601, 1992; compositions comprising fibroblast growth factor are described, for example, in Brown et al., *Surg.*, 121: 372-380, 1997; compositions comprising nerve growth factor are described in, for example, Matsuda et al., *J. Exp. Med.*, 187: 297-306, 1998.

Wound Dressings

The present invention also provides a wound dressing comprising a topical composition as described herein according to any embodiment. For example, a topical composition as described herein according to any embodiment is stably adsorbed or otherwise applied to a wound dressing material. For example, the present invention provides a wound dressing such as for example, a bandage, a vapour-permeable adhesive film (e.g., a polyurethane film), a hydrocolloid dressing (e.g., hydrophilic colloidal particles bound to polyurethane foam), an alginate dressing, a silicone mesh dressing, a tissue adhesive, a barrier film, calcium alginates dressing (e.g., nonwoven composites of fibers from calcium alginate) or a cellophane dressing (e.g., cellulose with a plasticizer). Suitable dressings are described, for example, in Kannon and Garrett, *Dermatol. Surg.* 21:583-590, 1995; or Davies, *Burns Incl Therm Inj.* 10: 94-103, 1983).

Alternatively, or in addition, the dressing is a scaffold, e.g., based on a biodegradable polymer. Such scaffolds are broken down either by hydrolysis or by enzymatic reaction into nontoxic molecules. The rate of degradation is controlled by manipulating the composition of the biodegradable polymer matrix. These types of systems can therefore be employed in certain settings for long-term release of biologically active agents. Examples of suitable biodegradable polymers include, for example, poly(glycolic acid) (PGA), poly-(lactic acid) (PLA), and poly(D,L-lactic-co-glycolic acid) (PLGA).

For example, a suitable scaffold is a collagen scaffold or a PLA scaffold or a fibrin scaffold. For example, a fibrin scaffold is capable of filling a void in a wound. Furthermore, a topical composition of the present invention as described herein according to any embodiment is incorporated into the fibrin scaffold at the time of polymerization, thereby providing for ease of production. Moreover, because release of the topical composition of the present invention from a scaffold, e.g., a fibrin scaffold is caused by cellular infiltrate into a wound (e.g., re-epethialization), such a scaffold establishes a biofeedback system, whereby release of the topical composition is based on an individual subject's healing rate (Feldman and Sierra Tissue Adhesives in Wound Healing, In: Handbook of Biomaterials and Maaplications, Marcel Dekker, 1994).

Examples of suitable fibrin scaffolds include, for example a scaffold comprising a mixture of porous fibrin matrix and a non-porous fibrin matrix (e.g., 12% porosity and 100-200 mm pores) (Pandit and Feldman, *Trans. Soc. Biomat.* 20: 34, 1994).

Alternatively, or in addition, a wound dressing comprises nanofibers. For example, polymer nanofibers are useful for applications such as tissue engineering, controlled drug release, wound dressings and medical implants. Suitable nanofibers are described, for example, in Zhang et al., *J Mater Sci Mater Med.* 16: 933-46, 2005.

In another example of the present invention, a wound dressing is an artificial skin or cultured dermal substitute. In such a wound dressing, the topical composition as described herein according to any embodiment may be applied to the dressing prior to application to a wound. For example, Ito et al., *Foot Ankle Int.* 27: 56-9, 2006 describe the treatment of ulcers using artificial dermis and recombinant basic fibroblast growth factor. Suitable skin substitutes or dermal substitutes will be apparent to the skilled artisan, and/or described in Barr-Meir et al., *Isr Med Assoc J.* 8:188-91, 2006; or Attiyeh et al., *Burns.* 31: 944-56, 2005.

Modes of Administration

The present invention contemplates any topical mode of administration of a topical composition as described herein according to any embodiment in a method of treatment. For example, a liquid topical composition is sprayed onto a wound and/or used to wash a wound and/or applied directly to the wound. Similarly a gel or cream is applied directly to a wound.

Alternatively, or in addition a topical composition is applied to a wound dressing, e.g., as described herein, and the wound dressing is applied to the wound.

Alternatively, a peptide AP-1 signaling inhibitor is expressed in a cell and the cell administered in a topical composition of the invention.

In another example, a topical composition of the invention comprises an AP-1 signaling inhibitor in a vesicle, e.g., a liposome (see Langer, *Science* 249:1527-1533 (1990); Treat et al., in Liposomes in the Therapy of infectious Disease and Cancer). Such a liposome is useful for the delivery of an AP-1 signaling inhibitor into a cell.

In the case of a topical composition comprising a nucleic acid inhibitor of AP-1 signaling, such a topical composition may be administered by particle bombardment. For example, gene gun has been used to deliver nucleic acids to wounds to thereby enhance wound healing, e.g., as described in (Andree et al., *Proc. Natl. Acad. Sci* 91: 188-112; or Lu et al., *Proc. Assoc. Am. Phys.*, 108: 165-172, 1996). Alternative methods for the delivery of nucleic acid inhibitors include, for example, microseeding (Erikkson et al., *J. Surg. Res.*, 78: 85-91, 1998), microfabricated needles (Henry et al., *J. Pharm. Sci.*, 87: 922-925, 1998), puncture mediated DNA transfer (Ciernik et al., *Hum. Gene Ther.*, 7: 893-899, 1996), lipid or liposome mediated delivery (Li et al., *In Vitro Cell Devel., Biol.*, 29A: 258-260, 1993; or Alexander et al., *Hum. Mol. Genet.*, 4: 2279-2285, 1995).

Screening Method

The present invention also provides a method for identifying a compound suitable for topical administration for the treatment of a dermal wound, said method comprising:
(i) topically administering to a dermal wound an amount of a compound capable of inhibiting or reducing AP-1 signaling;
(ii) comparing the level of apoptosis and/or necrosis and/or the amount of wound healing in the wound to the level of apoptosis and/or necrosis and/or the amount of wound healing in the wound in a dermal wound to which the compound has not been administered; and
(iii) selecting a compound that reduces the level of apoptosis and/or necrosis and/or enhances the level of wound healing in a dermal wound to which it is administered compared to the level of apoptosis and/or necrosis and/or wound healing in a dermal wound to which the compound has not been administered, thereby identifying a compound suitable for topical administration for the treatment of a dermal wound.

Alternatively, or in addition, the method comprises:
(i) topically administering to a dermal wound of a compound capable of inhibiting or reducing AP-1 signaling;
(ii) comparing the level of cellular proliferation in the wound to the cellular proliferation in a dermal wound to which the compound has not been administered; and (iii) selecting a compound that enhances the level of cellular proliferation in a dermal wound to which it is administered compared to the level of cellular proliferation in a dermal wound to which the compound has not been administered, thereby identifying a compound suitable for topical administration for the treatment of a dermal wound.

Preferably, the method additionally comprises identifying a compound capable of inhibiting or reducing AP-1 signaling, e.g., using a method described herein.

Alternatively, or in addition, the method additionally comprises determining the level of apoptosis and/or necrosis in a wound to which the compound has been topically administered and/or determining the level of cellular proliferation in a wound to which the compound has been topically administered. The method may also comprise determining the level of apoptosis and/or necrosis and/or cellular proliferation in a dermal wound to which the compound has not been administered.

Methods for determining the level of apoptosis and/or necrosis and/or cellular proliferation will be apparent to the skilled artisan and/or described herein.

In another example, the method additionally comprises determining the level of wound healing in a wound to which the compound has been topically administered. The method may also comprise determining the level of wound healing in a dermal wound to which the compound has not been administered Methods for determining the level of wound healing will be apparent to the skilled artisan and/or described herein.

For example, the dermal wound is a thermal burn. For instance, the dermal wound is a thermal burn induced by applying a hot solid surface to the skin of a subject, e.g., a surface having a temperature of at least about 90° C. or at least about 95° C., e.g., as exemplified herein.

Alternatively, Williams et al., *Ann Emerg Med.* 23: 464-9, 1994 describe a murine model of an acid burn. In that model animals are anesthetized and a standardized chemical burn is created by topical application of 52% hydrofluoric acid. Such a model is useful for identifying a compound useful for the treatment of a chemical burn. For example a test compound is applied to the burn for a time and under conditions sufficient to inhibit apoptosis and/or necrosis and the level of apoptosis and/or necrosis and/or wound healing is determined and compared to the level of apoptosis and/or necrosis and/or wound healing in a burn to which the compound has not been administered.

Svedman et al., *Burns.* 17:41-6, 1991 describe a human model of radiation burn in which forearm blisters are induced in subjects by suction (e.g., at 200 mmHg below atmospheric for 2 h 15 min, blister roof cut at base), and the wounds are irradiated (u.v. irradiation given selectively for 30 min from a distance of 10 cm). This model is useful for the identification of a compound for the treatment of a radiation burn.

In another example, the dermal wound is an ulcer. For example, Mustoe et al., *J. Invest.,* 87: 694-703, 1991 describe a rabbit model of a dermal ulcer using surgical techniques to induce ulcer formation. Such a model is useful for the identification of a compound for the treatment of a dermal ulcer.

The present invention encompasses the use of any in silico analytical method and/or industrial process for carrying the screening methods described herein into a pilot scale production or industrial scale production of a compound identified in such screens. This invention also provides for the provision of information for any such production. Accordingly, the present invention also provides a process for identifying or determining a compound supra, said method comprising:

(i) performing a method as described herein according to any embodiment to thereby identify a compound;
(ii) optionally, determining the amount of the compound;
(iii) optionally, determining the structure of the compound; and
(iv) providing the compound or the name or structure of the compound such as, for example, in a paper form, machine-readable form, or computer-readable form.

As used herein, the term "providing the compound" shall be taken to include any chemical or recombinant synthetic means for producing said compound (with or without derivitisation) or alternatively, the provision of a compound that has been previously synthesized by any person or means.

In one example, the compound or the name or structure of the compound is provided with an indication as to its use e.g., as determined by a screen described herein.

The present invention additionally provides a process for producing a compound supra, said method comprising:
a process for identifying or determining a compound or modulator supra, said method comprising:
(i) performing a method as described herein according to any embodiment to thereby identify or determine a compound;
(ii) optionally, determining the amount of the compound;
(iii) optionally, determining the structure of the compound;
(iv) optionally, providing the name or structure of the compound such as, for example, in a paper form, machine-readable form, or computer-readable form; and
(v) providing the compound.

In the case of a peptide, the method optionally further comprises providing a chemical derivative of the peptide by protection of the amino- or carboxy-terminus, cyclisation of the peptide or construction of the peptide as a retroinverso peptide.

In one example, the compound or the name or structure of the compound is provided with an indication as to its use e.g., as determined by a screen described herein.

The present invention also provides a method of manufacturing a compound identified by a screening method described herein according to any embodiment for use in medicine comprising:
(i) performing a method as described herein according to any embodiment to thereby identify or determine a compound; and
(ii) using the compound in the manufacture of a therapeutic for use in medicine.

For example, the compound is used to manufacture a therapeutic for topical administration to a subject, e.g., for the treatment of a dermal wound.

In one example, the method comprises the additional step of isolating the compound. Alternatively, a compound is identified and is produced for use in the manufacture of a compound for use in medicine.

The present invention is described further in the following non-limiting examples:

EXAMPLE 1

Isolation of an Inhibitor of AP-1 Signaling

Nucleic acid was isolated from the following bacterial species:

| 1 | *Archaeoglobus fulgidis* |
| 2 | *Aquifex aeliticus* |
| 3 | *Aeropyrum pernix* |

|  |  |
|---|---|
| 4 | *Bacillus subtilis* |
| 5 | *Bordetella pertussis* TOX6 |
| 6 | *Borrelia burgdorferi* |
| 7 | *Chlamydia trachomatis* |
| 8 | *Escherichia coli* K12 |
| 9 | *Haemophilus influenzae* (rd) |
| 10 | *Helicobacter pylori* |
| 11 | *Methanobacterium thermoautotrophicum* |
| 12 | *Methanococcus jannaschii* |
| 13 | *Mycoplasma pneumoniae* |
| 14 | *Neisseria meningitidis* |
| 15 | *Pseudomonas aeruginosa* |
| 16 | *Pyrococcus horikoshii* |
| 17 | *S nechosistis* PCC 6803 |
| 18 | *Thermoplasma volcanium* |
| 19 | *Thermotoga maritima* |

Nucleic acid fragments were generated from the genomic DNA of each genome using 2 consecutive rounds of primer extension amplification using tagged random oligonucleotides with the sequence:

5'-GACTACAAGGACGACGACGACAAGGCTTATCAATCAATCAN$_6$-3'.

The PCR amplification was performed using the Klenow fragment of *E. coli* DNA polymerase I in the following primer extension reaction:

| Reagent | Volume |
|---|---|
| DNA (100-200 ng) Oligonucleotide comprising SEQ ID NO: 33 (25 µM) | 4 µl |
| H$_2$O | to 17.4 µl. |

Samples were then boiled for 3-5 minutes to denature the nucleic acid isolated from the bacteria, before being snap cooled, to allow the tagged random oligonucleotides to anneal to said nucleic acid. These samples were then added to the following reagents:

| | |
|---|---|
| Klenow buffer | 3 µl |
| dNTP (2 mM) | 3 µl |
| Klenow | 0.6 µl |
| Polyethylene Glycol (8,500) | 6 µl |

Primer extension reactions were then incubated at 15° C. for 30 minutes, then at room temperature for 2 hours, before being heated to 37° C. for 15 minutes.

Samples were boiled for 5 minutes to again denature the nucleic acid, before being snap cooled to allow renaturation of said nucleic acid. Another 0.5 µl of the Klenow fragment of *E. coli* DNA polymerase I was added to each reaction and the samples incubated at 15° C. for 30 minutes, then at room temperature for 2 hours, before being heated to 37° C. for 15 minutes.

Following boiling the samples, following snap cooling another 2 rounds of primer extension were completed using the tagged random oligonucleotide:

5'-GACTACAAGGACGACGACGACAAGGCTTATCAATCAATCAN$_9$-3'

To complete this the following reagents were added to the samples of the previous step:

| | |
|---|---|
| Oligonucleotide (25 µM) | 4 µl |
| Klenow Buffer | 1 µl |
| dNTP(2 mM) | 3 µl |
| Klenow | 0.5 µl |
| H$_2$O | to 40 µl |

Samples were then incubated at 15° C. for 30 minutes, then at room temperature for 2 hours, before being heated to 37° C. for 15 minutes.

Samples were boiled for 5 minutes to again denature the nucleic acid, before being snap cooled to allow renaturation of said nucleic acid. Another 0.411 of the Klenow fragment of *E. coli* DNA polymerase I was added to each reaction and the samples incubated at 15° C. for 30 minutes, then at room temperature for 2 hours, before being heated to 37° C. for 15 minutes.

Following completion of the primer extension amplification all sample volumes were increased to 500 µl with TE buffer and added to an Amicon spin column. These columns were then centrifuged for 15 minutes at 3,800 rpm in a microcentrifuge. Columns were then inverted and 30 µl of TE buffer was added before the columns were centrifuged for 2 minutes at 3,800 rpm, with this fraction collected for later use. The Klenow amplified DNA was then used in subsequent DNA manipulations.

The now purified primer extension products were then used in a PCR reaction with an oligonucleotide comprising the following sequence:

5'-GAGAGAATTCAGGTCAG<u>ACTA</u>CAAGGACGACGACGACAAG-3', wherein an EcoRI restriction endonuclease site is shown in bold text, and three stop codons are underlined. Note that each of the stop codons is in a different reading frame.

Thus, the following PCR reaction was used:

| | |
|---|---|
| Oligonucleotide comprising SEQ ID NO: 35 (10 µM) | 12 µl |
| PCR buffer | 5 µl |
| dNTP (2 mM) | 5 µl |
| Taq polymerase (Boehringer) 5.5 U/µl | 0.4 µl |
| H$_2$O | 26.6 µl |
| Klenow amplified DNA | 2 µl |

Reactions were then cycled in a thermocycler using the following program:

95° C. for 2 min; 60° C. for 30 sec; 72° C. for 1 min;
95° C. for 20 sec; 60° C. for 30 sec; 72° C. for 1 min (repeated 29 times); and
72° C. for 5 min.

PCR products were then purified using Amicon spins columns which fractionate on the basis of size.

The PCR products were then analyzed by electrophoresis on standard TAE-agarose gels to determine the approximate size of the nucleic acid fragments generated as shown in FIG. 2. The nucleic acid concentration of the samples was also determined.

PCR products from each of the 19 bacterial species were then pooled to generate a biodiverse nucleic acid library. To do so, DNA from each organism was added in an equimolar amount when compared to the amount of nucleic acid added to the pool from the organism with the smallest genome.

Between 1 µg and 10 µg of DNA from each organism was used, depending on the genome size of the organism from which the DNA was obtained.

Amplified fragments were digested with EcoRI and Acc651. The resulting fragments were then purified using a QIAQuick PCR purification column (Qiagen) essentially according to manufacturer's instructions. The expression vector pMF4-5 (Phylogical Limited, Perth, Australia) was also digested with EcoRI and Acc651, treated with shrimp alkaline phosphatase and then purified using a QIAQuick PCR purification column (Qiagen) essentially according to manufacturer's instructions. Ligations were then performed at a molar ratio of 10:1 insert:vector, and transformed into TOP10 electrocompetent cells (Invitrogen).

These vectors were then isolated from bacteria using standard methods and transformed into the PRT51 yeast strain (with the genotype MATα, his3, trp1, ura3, 6 LexA-LEU2, lys2::3 cIop-LYS2, CYH2R, ade2::G418-pZero-ade2, met15::Zeo-pBLUE-met15, his5::hygroR). Transformants were then aliquoted and snap frozen in 15% glycerol.

The bait and prey used in the present screen were JUN1 and JUNZ fragments of c-Jun. Briefly, nucleic acid encoding the JUN1 protein was cloned into the prey vector pJFK in operable connection with a nuclear localisation signal, and a B42 activation domain. The nucleic acid encoding the JUNZ protein was cloned into the bait vector pDD in operable connection with the LexA DNA binding domain. The pDD vector also contains a nucleic acid encoding the HIS3 gene. These vectors were then transformed into the yeast strain PRT480 (with the genotype MATα, his3, trp1, ura3, 4 LexA-LEU2, lys2::3 cIop-LYS2, CANR, CYH2R, ade2::2 LexA-CYH2-ZEO, his5::1 LexA-URA3-G418).

The yeast that carry the bait and prey proteins and the potential blocking peptides were then mass mated, and from approximately 300,000 clones, 95 positives were identified (ie, approximately 1/3000).

Two methods of analysis were used to identify interaction-blocking activity:

The first of these comprised plating approximately 500 cells per half plate onto HTU media containing plates and counting the number of colonies growing after 3 days. In these conditions, an interaction of JUN1 and JUNZ enables the cells to grow. Accordingly, a reduction in the number of colonies indicates that the library being screened comprises peptide inhibitors of the JUN1/JUNZ interaction.

The second screening method involved isolation and streaking of 10 individual colonies to new HTU media containing plates and analysing for growth of new single colonies. After 3 days, those that express a peptide inhibitor generally have very little or no new growth, while those that do not express a peptide inhibitor have re-grown a streak of single colonies. As a positive control a known inhibitor of JUN1/JUNZ interaction, FosZ was used. As a negative control empty pYTB3 vector with no peptide insert was used. A score of 1-10 given depending on growth of 10 individual clones of each peptide copared to the two control samples.

The score from method 1 and method 2 was then combined to determine if a specific colony expressed a peptide inhibotor of JUN1/JUNZ interaction. In the present case a cell expressing a peptide inhibitor was one that showed >50% reduction of growth compared to negative control in both tests.

All scoring was performed by two independent individuals and scores of both individuals were combined.

Following screening peptides comprising a sequence set forth in any one of SEQ ID NOs: 26, 28, 30, 32, 34, 36, 38, 40, 42, 44, 46, 48, 50, 52, 54, 56, 58, 60, 62, 64, 66, 68, 70 or 72 were identified.

The ability of the peptides to interact with JUN1 was then confirmed with a forward two-hybrid assay. Each of the identified peptides capable of inhibiting the interaction of JUN1 and JUNZ was cloned into the bait vector pDD. Additionally, nucleic acid encoding a peptide known not to inhibit the interaction between JUN1 and JUNZ was also cloned into pDD. The pDD vector and the JUN1 prey vector was transformed into the yeast strain PRT480 and the interaction of the encoded peptide and JUN1 assessed by determining the amount of growth in the absence of uracil.

EXAMPLE 2

Treatment of Burns Using an Inhibitor of c-Jun Dimerization 1.1 Materials and Methods Animals 8 week old C57/B16 mice were purchased from the Animal Resource Center, Murdoch University, Western Australia and used for all experiments. All experiments were approved by the necessary institutional animal ethics committees and were performed in accordance with the National Health and Medical Research Council (NHMRC) Australian Code of Practice for the Care and Use of Animals for Scientific Purposes.

Peptide

A peptide used was synthesised by Mimotopes Pty Ltd (Melbourne, Australia) and supplied as a lyophilised powder (purity>90%). The peptide (H-rerrsssqiGGsrisqyaGrrrqr-rkkrG-NH2) (SEQ ID NO: 104) is a D-form retro-inverted mimic of a peptide originally identified in a screen for inhibitors of AP-1 signaling e.g., by virtue of inhibiting c-Jun dimerization (as described in Example 1, i.e., a peptide comprising an amino acid sequence set forth in SEQ ID NO: 57), and is fused to the TAT 10-mer for penetration across cell membranes, with a linking glycine between the peptide and TAT sequence to facilitate the independent folding of each of said components.

Procedure

A full-thickness burn wound was generated in a murine subject using a modified protocol based on a model previously described (Bruen et al., *J Surg Res*, 120: 12-20, 2004). Briefly, mice (n=34) were anesthetised (xylazine (10 mg/kg) and ketamine (100 mg/kg)) and subsequently given a full-thickness 10 mm diameter burn by contact with a brass rod (65 g) heated to 95° C. and applied for 9 seconds. 10 control animals were sacrificed post-burn, and histology confirmed all burns were full-thickness. The remaining animals (n=24) were re-hydrated and given analgesics subcutaneously immediately post-burn. The wounds were then dressed using a Tegapore™ membrane dressing (3M Healthcare Ltd) and either phosphate buffered saline (PBS) or PBS containing 20 µM peptide were instilled into the Tegapore™ and administered topically. The mice were then wrapped with a secondary absorbent dressing with minimal pressure so as not to constrict breathing and to allow free movement of the animal after recovery. Ten minutes post-injury, dressings were removed and animals allowed to recover from anesthesia in their cages with feed and water provided ad libitum.

Pathological Processing

Wounds were harvested on post-injury days 1, 3, 7 and 11 (n=3 for each time-point for both treated and control groups). Each wound was bisected along the cranial-caudal axis and one half of the tissue fixed in 4% paraformaldehyde solution and the other half stored as frozen tissue. Haematoxylin and Eosin stained sections were used to determine the quality of wound healing.

TUNEL Assay

Tissue sections were labelled using TUNEL (Tdt-mediated dUTP Nick End Labelling) assay as previously described 13. Skin tissue sections were dewaxed by two subsequent 5 minute washes in toluene and then hydrated by immersion in decreasing concentrations of ethanol and finally PBS (pH 7.4). The tissue sections were pre-treated with proteinase K (20 μg/ml in PBS) for 30 min at 37° C., hydrogen peroxide solution (3% in PBS) for 10 minutes at room temperature and then washed in PBS twice for 5 minutes each wash. Following pre-treatment, an Apoptag Plus peroxidase in situ Apoptosis Detection Kit (Chemicon International, Temecula, Calif.) was used for nick-end labelling, following the manufacturer's instructions. The sections were then counterstained using methyl green for 10 minutes, destained using N-butanol and dehydrated by two 5 minute washes in toluene. Intensity of TUNEL staining was quantitated using Image J software (available from The National Institutes of Health, USA). Intensity of staining of individual nuclei were measured and normalised against the background. The mean intensity of 5 adjacent nuclei was taken as the level of intensity for that area. Each 5 nuclei equates to 1 distance unit from the burn injury on the graph presented in FIG. 4B.

Statistical Analysis

Progress of re-epithelialisation was quantitated by measuring distance between leading epithelial edges using an eyepiece graticule on histological slides. Difference between treated and control wounds was analysed using standard two-tail t-TEST for two-samples assuming unequal variance. $p<0.05$ is defined as the level of statistical significance.

1.2 Results

Gross Morphology

Figure 2A:
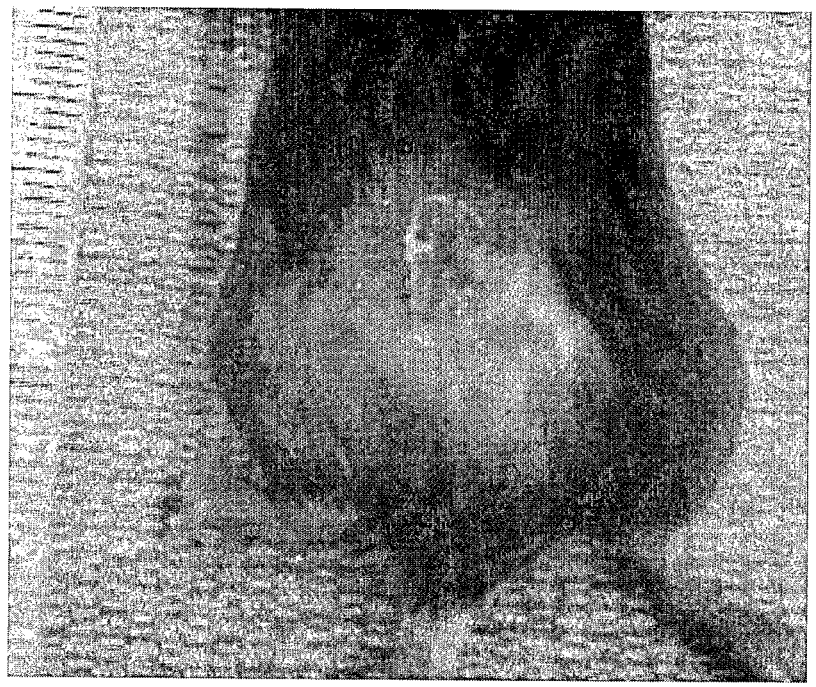
FIG. 2a is a copy of a photograph showing a burn in a control (untreated) subject 7 days after burning.
Figure 2B:
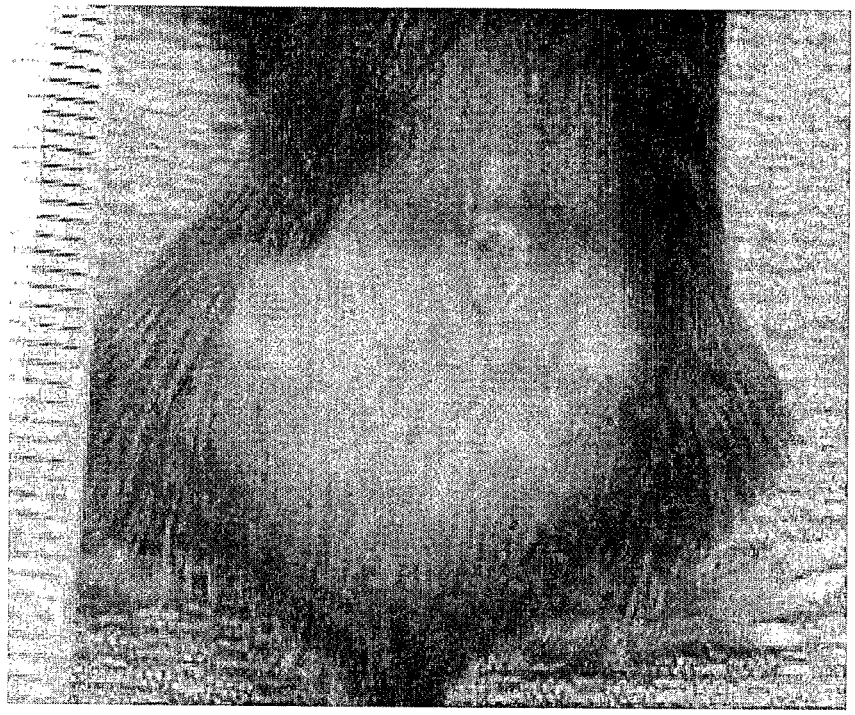
FIG. 2b is a copy of a photograph showing a burn in a treated subject 7 days after burning. The wound appears to be more advanced in healing compared to the wound in the control subject shown in FIG. 1A.
Figure 2C:
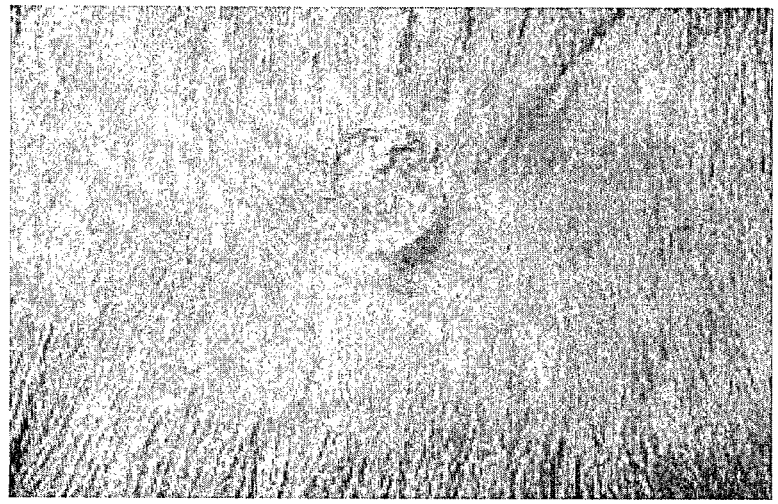
FIG. 2c is a copy of a photograph showing a burn in a control (untreated) subject 11 days after burning.
Figure 2D:
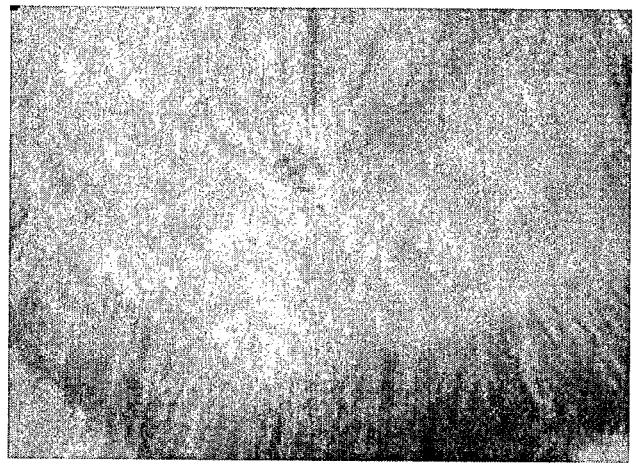
FIG. 2d is a copy of a photograph showing a burn in a treated subject 11 days after burning. The wound appears to be more advanced in healing compared to the wound in the control subject shown in FIG. 1C.
Figure 3A:
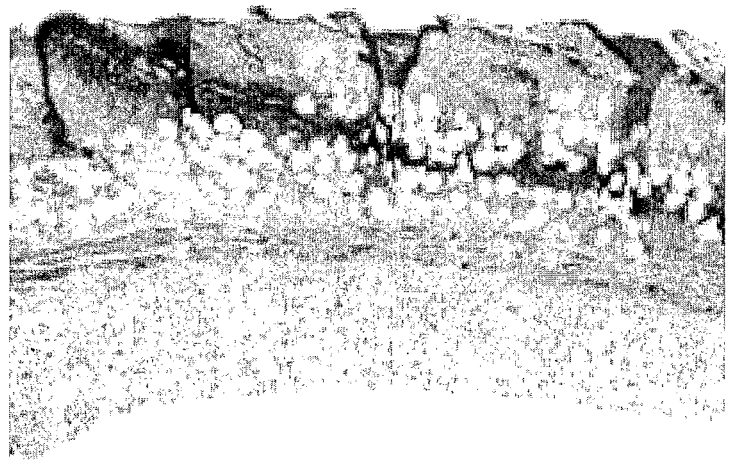
FIG. 3a is a copy of a photomicrograph showing the morphology of a burn in a control subject 24 hours after burning.
Figure 3B:
FIG. 3b is a copy of a photomicrograph showing the morphology of a burn in a treated subject 24 hours after burning.
Figure 3C:
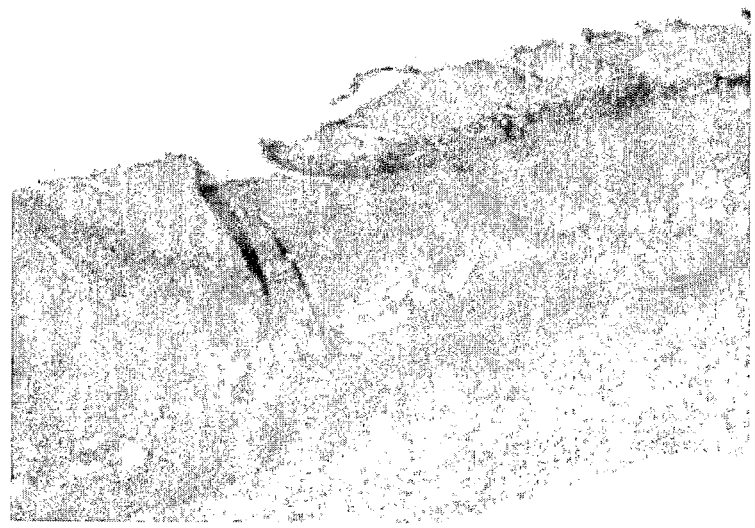
FIG. 3c is a copy of a photomicrograph showing the morphology of a burn in a control subject 3 days after burning.
Figure 3D:
FIG. 3d is a copy of a photomicrograph showing the morphology of a burn in a treated subject 3 days after burning.
Figure 3E:
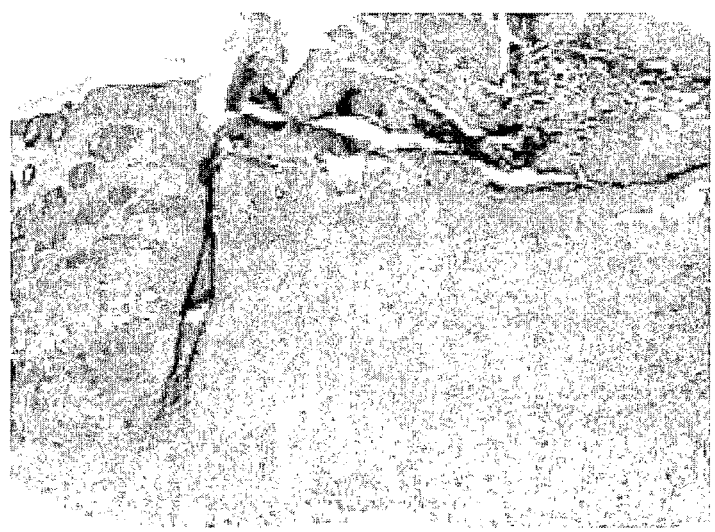
FIG. 3e is a copy of a photomicrograph showing the morphology of a burn in a control subject 7 days after burning.
Figure 3F:
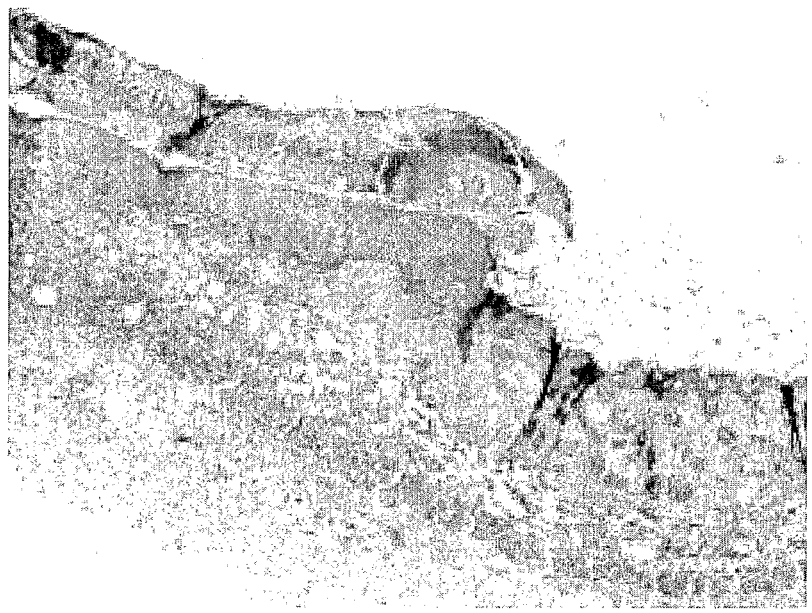
FIG. 3f is a copy of a photomicrograph showing the morphology of a burn in a treated subject 7 days after burning. Re-epithelialization of the wound is more advanced than in the control wound shown in FIG. 3e.
Figure 3G:
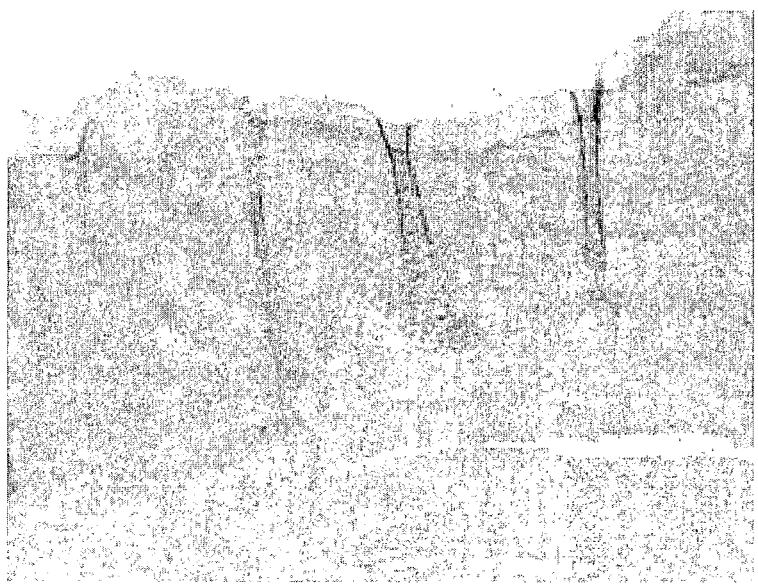
FIG. 3g is a copy of a photomicrograph showing the morphology of a burn in a control subject 11 days after burning.
Figure 3H:
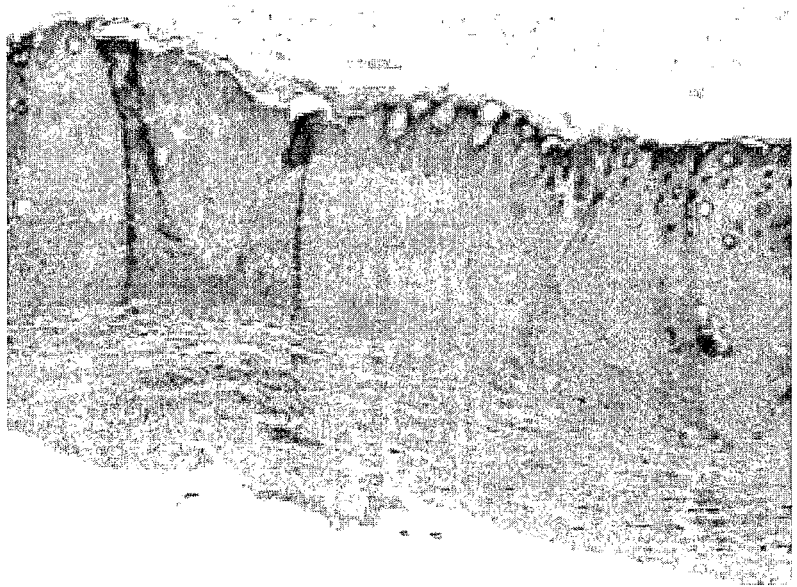
FIG. 3h is a copy of a photomicrograph showing the morphology of a burn in a treated subject 11 days after burning. The wound is re-epithelialized. In contrast, the wound in the control shown in FIG. 3g has not re-epithelialized.

All wounds appear equivalent in size and depth at time of surgery and in the early study period (Days 0 and 3). By Day 7, significant differences are observed between those wounds treated with peptide and the control groups (FIGS. 2a and 2b). Early reepithelialization is present and separation of the eschar evident in the treated group (FIG. 2b). In the control wounds the eschar is more firmly adherent and epithelialization slower (FIG. 2a). By day 11 healing in both groups is at an advanced stage. The treated wounds are smaller and the epithelium less fragile (FIG. 2d) than in control wounds (FIG. 2c). By day 11, the eschar is <2 mm in diameter in the treated group, whilst the eschar is at least 3 mm in diameter in the control wounds. Contracture is evident adjacent to the wound edges and similar in both treated and control groups.

Wound Histology Observations

Peptide Treated Wounds Show Faster Re-epithelialisation

The wounds treated with peptide appear to re-epithelialize faster than control wounds. For example, by day 7, the treated wounds have a gap of 2 mm without epidermis, whilst the control wounds have a gap of 4.5 mm that is not re-epithelialized (FIG. 3). By day 11, all the treated wounds are covered, whilst the control wounds are still not completely epithelialized, with a remaining gap of 2 mm (FIG. 3).

Figure 4A:
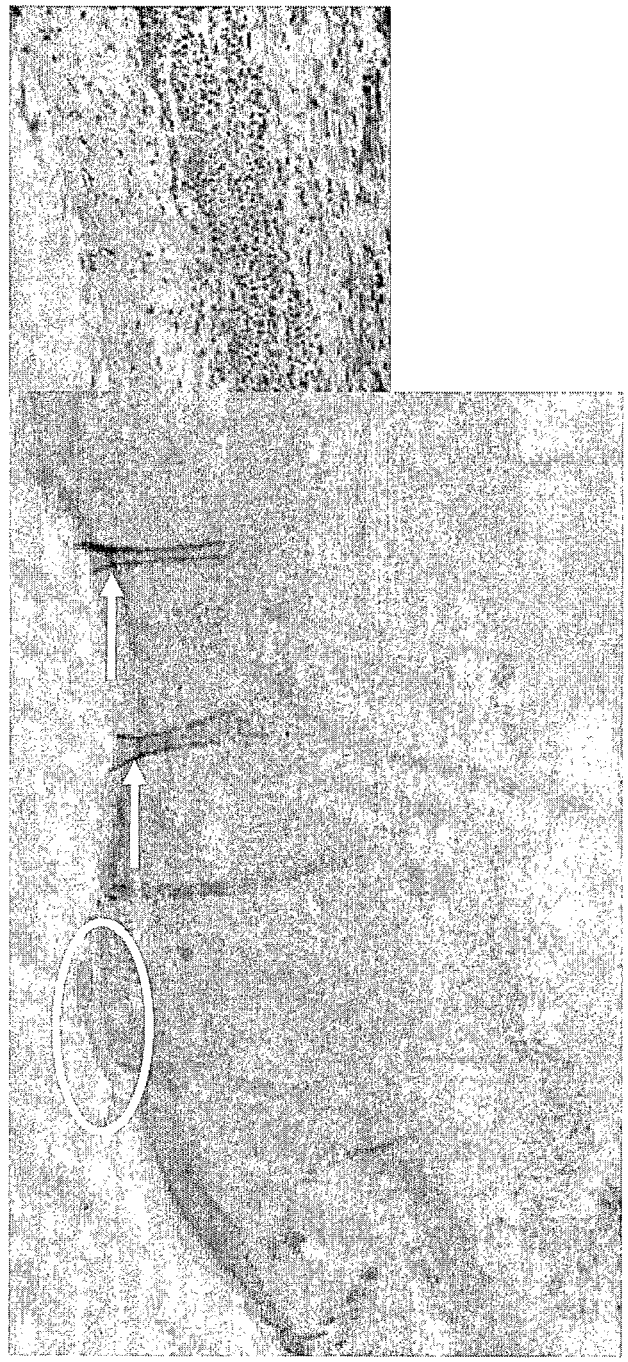
FIG. 4a is a copy of two photomicrographs showing morphology of an untreated burn eleven days following burning. The left-hand photomicrograph shows 2× magnification, and the right-hand photomicrograph shows 20× magnification. The circled area indicates hyperproliferating wound edge. The arrows indicate areas of incomplete epithelialization.
Figure 4B:
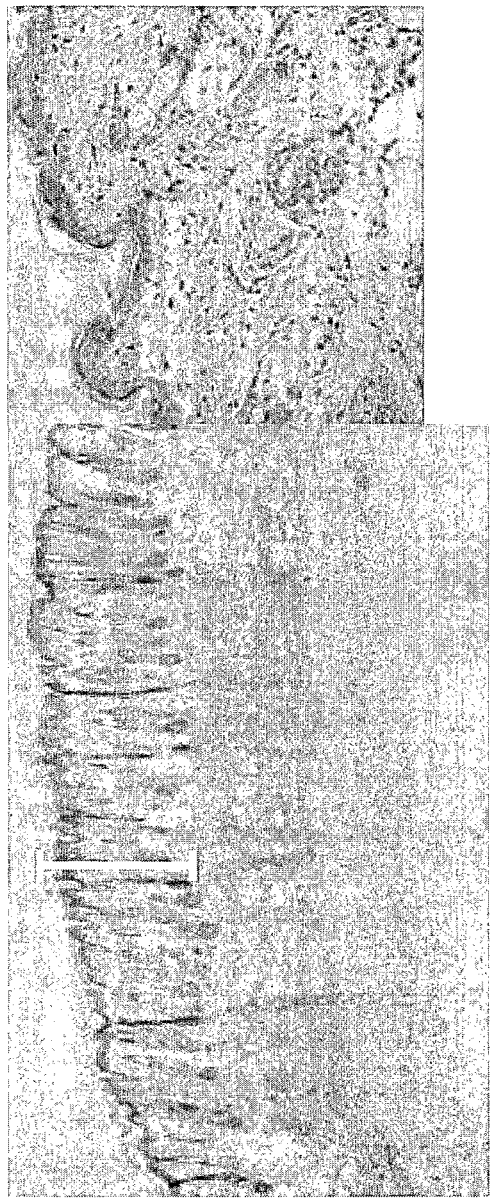
FIG. 4b is a copy of two photomicrographs showing morphology of a burn eleven days following burning. The burn was treated with a peptide analog comprising the amino acid sequence set forth in SEQ ID NO: 104. The left-hand photomicrograph shows 2× magnification, and the right-hand photomicrograph shows 20× magnification. The circled area indicates hyperproliferating wound edge. The bar indicates an area in which de novo hair follicle morphogenesis is occurring, indicating that scarring has not occurred.

Moreover, as shown in FIG. 4a, at day 11 a treated wound is completely re-epithelialized and de novo hair follicle morphogenesis is occurring. Such de novo hair follicle morphogenesis indicates that scarring has not occurred in the treated wound.

In contrast, as shown in FIG. 4, at day 11 a non-treated wound is incompletely epithelialized and is still underoing healing, as indicated by the hyperproliferating wound edge.

Figure 5:
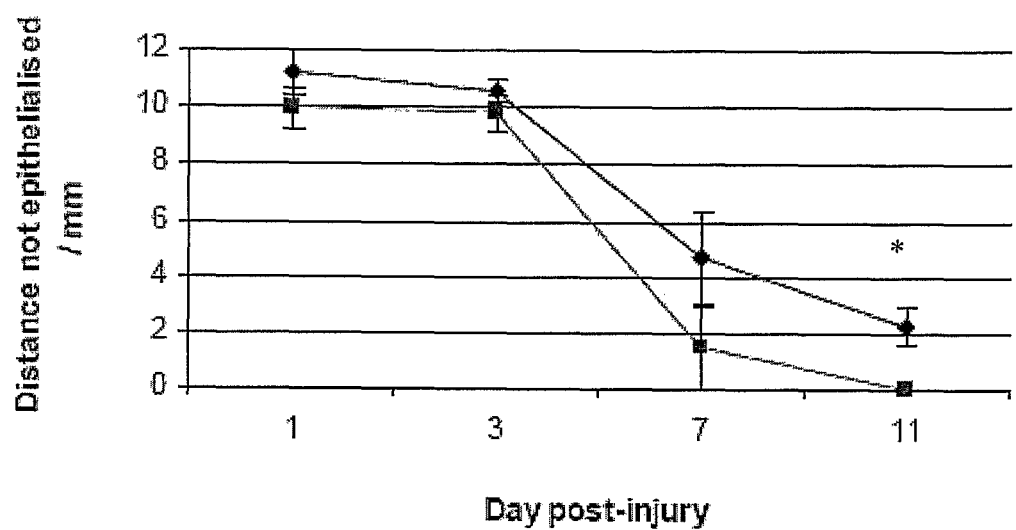
FIG. 5 is a graphical representation showing the level of re-epithelialization of burns. Measurements between the two leading edges of the wound to determine the gap remaining to be re-epithelialized. Treated wounds (squares) are re-epithelialized by day 11, whereas control wounds (diamonds) are on average 2 mm wide (*, p<0.05).

The difference in the rate of re-epithelialization is statistically significant ($p<0.05$). The time course of re-epithelialisation clearly indicates the significant difference in the rate of re-epithelialisation (FIG. 5). In addition, it appears that treated wounds do not increase in size within 24 hours post-injury, remaining at 10 mm in size between leading epidermal edges, whilst the control wounds increase in size to an average of 11 mm between leading edges (FIG. 5).

Peptide Protects Cells in the Zone of Stasis

Figure 6A:
FIG. 6a is a copy of a photomicrograph showing TUNEL staining to detect apoptotic cells in a control (untreated) wound adjacent the wound edge one day after burning. Arrow indicates the edge of the wound.
Figure 6B:
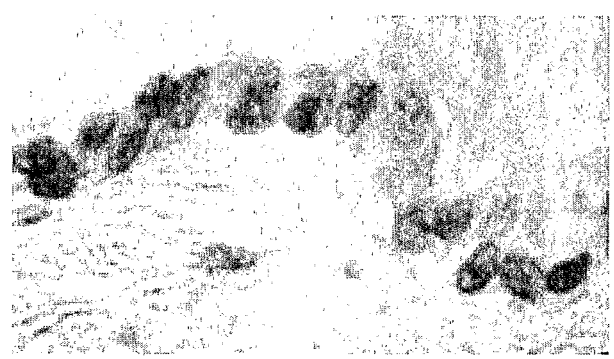
FIG. 6b is a copy of a photomicrograph showing TUNEL staining to detect apoptotic cells in a control (untreated) wound 500 μm from the wound edge one day after burning.
Figure 6C:
FIG. 6c is a copy of a photomicrograph showing TUNEL staining to detect apoptotic cells in a control (untreated) wound 1500 μm from the wound edge one day after burning.
Figure 6D:
FIG. 6d is a copy of a photomicrograph showing TUNEL staining to detect apoptotic cells in a treated wound adjacent the wound edge one day after burning. Arrow indicates the edge of the wound.
Figure 6E:
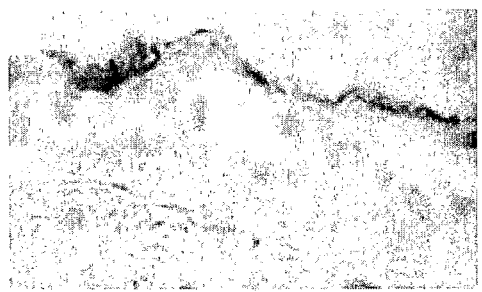
FIG. 6e is a copy of a photomicrograph showing TUNEL staining to detect apoptotic cells in a treated wound 500 μm from the wound edge one day after burning.
Figure 6F:
FIG. 6f is a copy of a photomicrograph showing TUNEL staining to detect apoptotic cells in a treated wound 1500 μm from the wound edge one day after burning.
Figure 7:
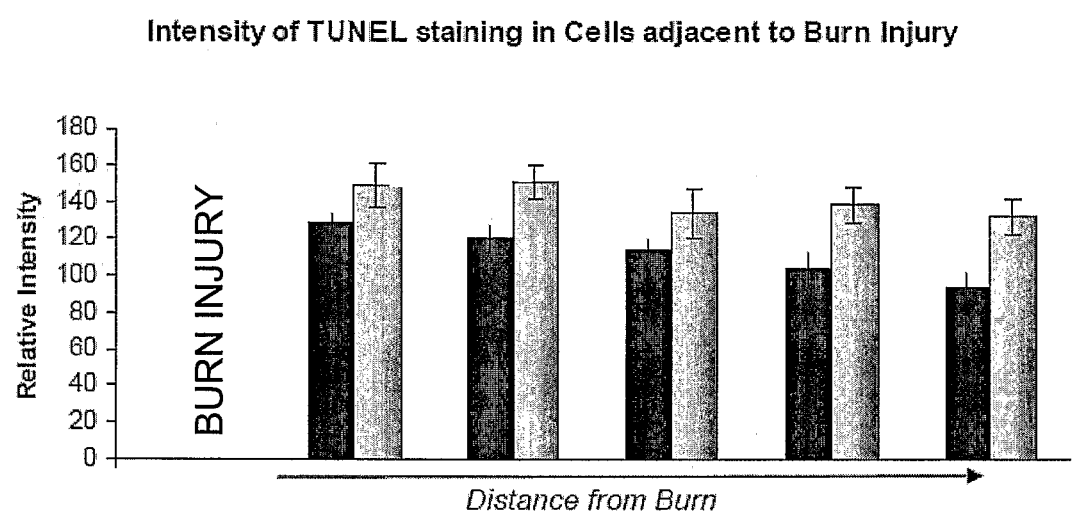
FIG. 7 is a graphical representation showing the intensity of TUNEL staining in individual cells as determined using Image J software. Comparative intensity shows staining in control epidermal cells (light bars) is more intense and is intense further from the wound edge than in treated samples (dark bars). Treated samples show rapid decrease in staining intensity with increasing distance from the injury.

Using TUNEL staining to identify apoptosing cells and to indicate the level of cell death surrounding the injury, it appears that the level of apoptosis in cells immediately adjacent to the wound is similar (FIGS. 6a and 6d). However, as distance from the injury increases, the level of positively staining cells decreases rapidly in treated epidermis, whilst in control samples the level of intensity remains similar. There is a marked difference in intensity at 500 μm from the wound edge (FIGS. 6b and 6e), and complete lack of positive staining in treated epidermis at 1500 μm from the wound edge. This is in contrast to the controls that show marked positive staining up to 1500 μm from the wound edge. Apoptosis of infiltrating cells appears similar in both treated and control wounds (data not shown). Quantitation of the intensity of TUNEL staining to indicate likelihood of cells undergoing apoptosis indicates that cells close to the wound in treated samples stain with less intensity than those of controls. In addition, the intensity of staining reduces more rapidly as distance from the wound increases in the treated samples versus controls (FIG. 6).

EXAMPLE 3

An Inhibitor of AP-1 Signaling Enhances and/or Induces Cellular Proliferation

Cultures of keratinocytes (HaCaT cells) or fibroblasts were cultured in a microwell plate the presence of a peptide analog comprising the amino acid sequence set forth in SEQ ID NO: 104 at a concentration of 100 nm, 1 μM or 10 μM. Following an incubation period 24 hours, 48 hours, or 72 hours, cells were incubated in the presence of MTT for a sufficient time for a mitochondrial dehydrogenase enzyme from viable cells to cleave the tetrazolium rings of the pale yellow MTT and form dark blue formazan crystals. Cells were then solubilized and the level of formalin crystals determined using a microtitre plate reader at 492 nm.

Figure 8A:
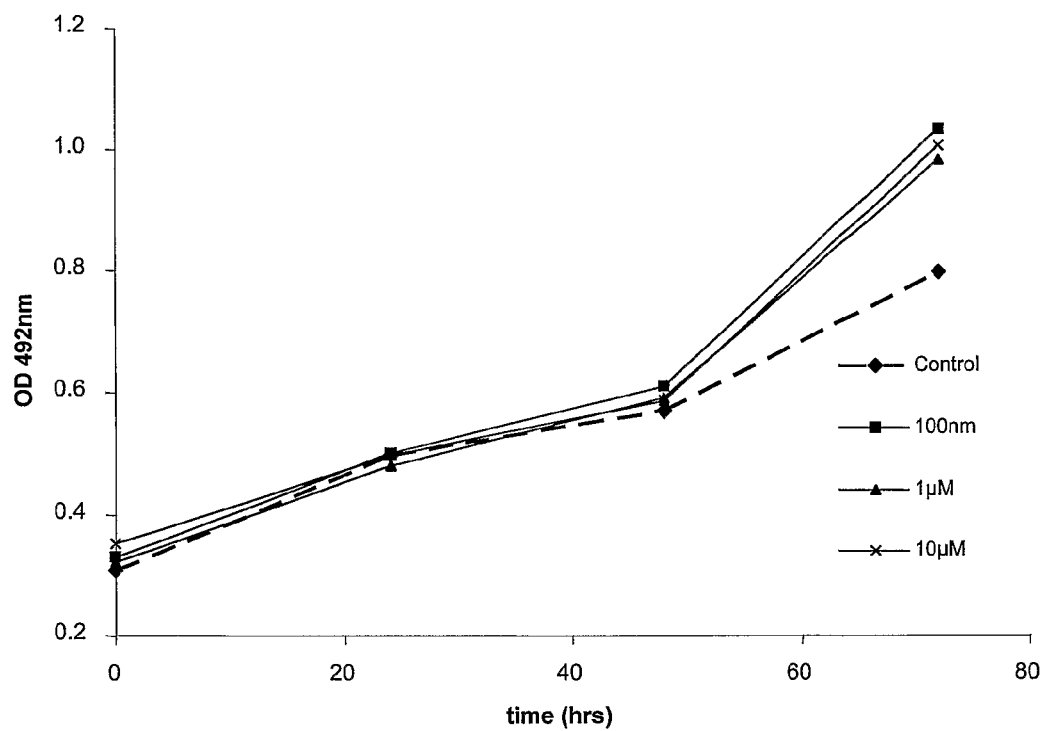
FIG. 8a is a graphical representation showing the level of cellular proliferation in HaCat keratinocyte cells treated with a peptide analog comprising the amino acid sequence set forth in SEQ ID NO: 104 as measured using a 3-(4,5-Dimethylthiazol-2-yl)-2,5-diphenyltetrazolium bromide (MTT) colorimetric assay. Treatment groups are indicated at the right-hand side of the figure. Cell treatment with all concentrations of the peptide analog increased cellular proliferation rates compared to control (untreated) cells.
Figure 8B:
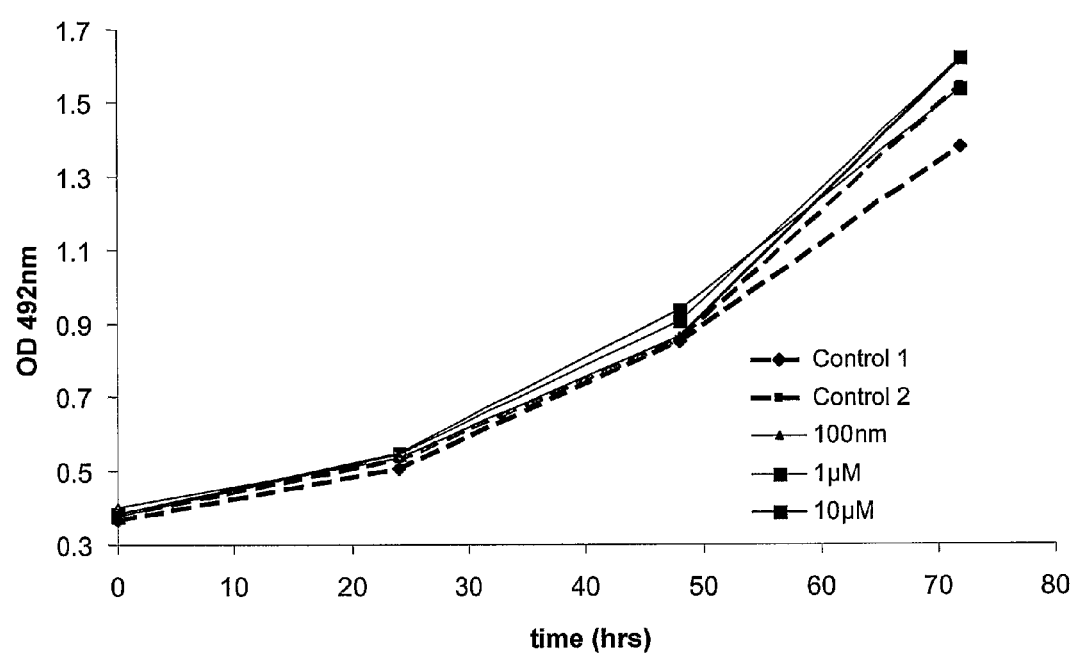
FIG. 8b is a graphical representation showing the level of cellular proliferation in fibroblast cells treated with a peptide analog comprising the amino acid sequence set forth in SEQ ID NO: 104 as measured using a MTT colorimetric assay. Treatment groups are indicated at the right-hand side of the figure.

As shown in FIG. 8a, the peptide analog enhanced and/or induced proliferation of HaCat keratinocytes, which are associated with wound healing. The peptide analog did not stimulate proliferation of fibroblast cells, which are associated with scar formation.

EXAMPLE 4

Treatment of an Ulcer with an Inhibitor of AP-1 Signaling

Dermal wounds are induced in ears of rabbits essentially as described in Mustoe et al., *J. Clin. Invest.*, 87: 694-703, 1991. Briefly, young adult New Zealand white rabbits are anaesthetized with ketamine and xylazine. Ears of the rabbits are immobilized in a plexiglass fabricated immobilizer and four 6 mm ulcers are made to the depth of bare cartilage under sterile conditions using microsurgical instruments and a 6 mm trephine. A peptide comprising an amino acid sequence set forth in any one of SEQ ID NOs: 74, 76, 78, 80, 82, 84, 86, 88, 90, 92, 94, 96, 98, 100, 102, 104, 106, 108, 110, 112, 114, 116, 118, 120, 125-128, 130 and 165 in PBS or PBS alone are applied and the wounds covered with an occlusive polyurethane film. Rabbits are sacrificed at various time points and ulcers are photographed, bisected and fixed in 10% formalin.

Sections of fixed tissue are stained with haemotoxylin and eosin and the epithelial gap (EG), granulation tissue gap (GTG) and maximum height (MH) of granulation tissue at the advancing edges of the wound are measured using a calibrated lens micrometer.

Approximate area and volume measurements for new granulation tissue are calculated, based on the assumption that wounds healed concentrically and did not contract.

The level of apoptosis in each wound is also determined essentially as described in Example 1.

Using this method inhibitors of AP-1 signaling capable of enhancing dermal ulcer healing are identified.

The ability of each of the peptide analogs to enhance or induce proliferation of keratinocytes and/or fibroblasts is also determined by performing the MTT assay described in Example 2.

We claim:

1. A topical composition comprising (i) an amount of a peptide analog consisting of an amino acid sequence set forth by SEQ ID NO: 104 wherein all amino acids other than glycine are D-amino acids; and (ii) a suitable carrier or excipient.

2. The topical composition according to claim 1 wherein the carrier or excipient is a topical carrier or excipient or other carrier or excipient for dermal application.

3. The topical composition according to claim 2 wherein the carrier or excipient provides a buffering activity to maintain the peptide analog at a suitable pH to thereby exert its biological activity.

4. The topical composition according to claim 1 wherein the carrier or excipient comprises a compound that enhances cellular uptake of the peptide analog or enhances transdermal delivery of the peptide analog.

5. The topical composition according to claim 1 additionally comprising a growth factor, an antibiotic or an anaesthetic.

6. The topical composition according to claim 1 wherein the composition is a liquid or a cream or a gel or a lotion.

7. The topical composition according to claim 1 wherein the composition is a liquid.

8. A wound dressing comprising the topical composition according to claim 1.

9. The wound dressing according to claim 8, wherein the dressing is a fabric bandage or a plastic bandage or a gauze bandage or a gauze dressing or a trauma dressing impregnated with the topical composition.

10. The wound dressing according to claim 8, wherein the dressing is a bio-degradable scaffold.

11. A method for producing the topical composition according to claim 1, said method comprising mixing or otherwise combining (i) an amount of a peptide analog consisting of an amino acid sequence set forth by SEQ ID NO: 104 wherein all amino acids other than glycine are D-amino acids; and (ii) a suitable carrier or excipient.

12. The method according to claim 11 additionally comprising producing or obtaining the peptide analog.

13. A method of treating a dermal wound, the method comprising topically administering to a subject in need thereof the topical composition according to claim 1, for a time and under conditions sufficient for the peptide analog to reduce apoptosis or necrosis induced by dermal wounding or enhance proliferation of a cell, thereby treating the dermal wound.

14. The method according to claim 13 comprising topically administering the topical composition to a region of a dermal layer surrounding a dermal wound.

15. The method according to claim 13 wherein the peptide analog is administered by topically administering a recombinant cell expressing said peptide analog to the subject.

16. The method according to claim 13 for treating an ulcer.

17. The method according to claim 13 for treating a burn.

18. The topical composition according to claim 1 for treating a dermal wound.

19. The topical composition according to claim 1, wherein the amount of the peptide analog in said composition is sufficient to reduce or delay apoptosis and necrosis induced by dermal wounding and to induce or enhance proliferation of a cell.

20. The method according to claim 11, wherein the amount of the peptide analog is sufficient to reduce apoptosis and necrosis induced by dermal wounding and enhance proliferation of a cell.

21. The method according to claim 13, wherein the administering of the topical composition to the subject in need thereof is for a time and under conditions sufficient for the peptide analog to reduce apoptosis and necrosis induced by dermal wounding and enhance proliferation of a cell, thereby treating the dermal wound.

* * * * *

SEQUENCE LISTING

```
<160> NUMBER OF SEQ ID NOS: 165

<210> SEQ ID NO 1
<211> LENGTH: 419
<212> TYPE: DNA
<213> ORGANISM: artificial
<220> FEATURE:
<223> OTHER INFORMATION: DNA encoding FLAG-PYC4 peptide
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (241)..(241)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (354)..(354)
<223> OTHER INFORMATION: n is a, c, g, or t
<220> FEATURE:
<221> NAME/KEY: misc_feature
<222> LOCATION: (356)..(356)
<223> OTHER INFORMATION: n is a, c, g, or t
<220> FEATURE:
<221> NAME/KEY: misc_feature
<222> LOCATION: (365)..(365)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (383)..(383)
<223> OTHER INFORMATION: n is a, c, g, or t
<220> FEATURE:
<221> NAME/KEY: misc_feature
<222> LOCATION: (386)..(386)
```

```
<223> OTHER INFORMATION: n is a, c, g, or t
<220> FEATURE:
<221> NAME/KEY: misc_feature
<222> LOCATION: (388)..(388)
<223> OTHER INFORMATION: n is a, c, g, or t
<220> FEATURE:
<221> NAME/KEY: misc_feature
<222> LOCATION: (392)..(392)
<223> OTHER INFORMATION: n is a, c, g, or t
<220> FEATURE:
<221> NAME/KEY: misc_feature
<222> LOCATION: (394)..(394)
<223> OTHER INFORMATION: n is a, c, g, or t
<220> FEATURE:
<221> NAME/KEY: misc_feature
<222> LOCATION: (397)..(397)
<223> OTHER INFORMATION: n is a, c, g, or t
<220> FEATURE:
<221> NAME/KEY: misc_feature
<222> LOCATION: (400)..(400)
<223> OTHER INFORMATION: n is a, c, g, or t
<220> FEATURE:
<221> NAME/KEY: misc_feature
<222> LOCATION: (403)..(404)
<223> OTHER INFORMATION: n is a, c, g, or t
<220> FEATURE:
<221> NAME/KEY: misc_feature
<222> LOCATION: (407)..(407)
<223> OTHER INFORMATION: n is a, c, g, or t
<220> FEATURE:
<221> NAME/KEY: misc_feature
<222> LOCATION: (415)..(415)
<223> OTHER INFORMATION: n is a, c, g, or t

<400> SEQUENCE: 1
gggagacccn ngcttggtac cnngctcgga tccngtatgg gtaagcctat ccctaacccT      60
ctcctcggtc tcgattctac acaagctatg ggtgctcctc caaaaaagaa gagaaaggta    120
gctgaattca ggtcagacta caaggacgac gacgacaagg cttatcaatc catgtgatgt    180
gaaagccgct tcctggacaa tgcatctgcc cctgccatga ggaatgcaaa gaggcgttcc    240
naagagcggg tcctgtgtaa cctgacagtt catagaaaac acattttgca caagatcacn    300
agtgatgacc tcttccggac ngcnttctgc atnaatccnt ttatcttttA tggncncaag    360
atgangcgca tgattgantt ganaangntt gncntcntcn tcnntgnagt ctganctgg    419

<210> SEQ ID NO 2
<211> LENGTH: 243
<212> TYPE: DNA
<213> ORGANISM: artificial
<220> FEATURE:
<223> OTHER INFORMATION: DNA encoding FLAG-PYC6 peptide
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 2
gggagacccn ngcttggtac cnngctcgga tccagtatgg gtaagcctat ccctaacccT      60
ctcctcggtc tcgattctac acaagctatg ggtgctcctc caaaaaagaa gagaaaggta    120
gctgaattca ggtcagacta caaggacgac gacgacaagg cttatcaatc taagagactt    180
tgaagatagt gtccaattgg catgtgccac agttaaccaa cttactgcaa tcattacccg    240
tga                                                                    243
```

```
<210> SEQ ID NO 3
<211> LENGTH: 387
<212> TYPE: DNA
<213> ORGANISM: artificial
<220> FEATURE:
<223> OTHER INFORMATION: DNA encoding FLAG-PYC8 peptide

<400> SEQUENCE: 3
aggtcagact acaaggacga cgacgacaag gcttatcaat caatcatagc taatgaagag      60
gagagggaga aaattttgc atccagcaaa aaggacggat cctataccga tctcttgtga     120
aacgaatgaa aaatagctct taaatccaga tatgtgtaag aatgcctcca tgattcgtgg     180
atcagaggat tgatagacca gagcttgtcg tcgtcgtcct tgtagtctga cctggtacca     240
attgatgcat cgataccggt actagtcgga ccgcatatgc ccgggcgtac cgcggccgct     300
cgaggcatgc atctagaggg ccgcatcatg taattagtta tgtcacgctt acattcacgc     360
cctcccccca catccgctct aaccgaa                                         387

<210> SEQ ID NO 4
<211> LENGTH: 193
<212> TYPE: DNA
<213> ORGANISM: artificial
<220> FEATURE:
<223> OTHER INFORMATION: DNA encoding FLAG-PYC12 peptide

<400> SEQUENCE: 4
aggtcagact acaaggacga cgacgacaag gcttatcaag agtccaccaa agcgctggtg      60
gaaggtggcg cggatctgat cctgattgaa accgttcttg tcgtcgtcgt ccttgtagtc     120
tgacctggta ccaattgatg catcgatacc ggtactagtc ggaccgcata tgcccgggcg     180
taccgcggcc gct                                                        193

<210> SEQ ID NO 5
<211> LENGTH: 709
<212> TYPE: DNA
<213> ORGANISM: artificial
<220> FEATURE:
<223> OTHER INFORMATION: DNA encoding FLAG-PYC15 peptide
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 5
gggagacccn ngcttggtac cnngctcgga tccagtatgg gtaagcctat ccctaaccct      60
ctcctcggtc tcgattctac acaagctatg ggtgctcctc aaaaaagaa gagaaaggta     120 gctgaattca ggtcagacta caaggacgac gacgacaaga cttatcaatc aatcaaaggc     180
ccagaaaata aagtgaaaat gtatttttg aatgatttaa atttctctag acgcgatgct     240
ggatttaaag caagaaaaga tgcactggac attgcttcag attatgaaaa catttctgtt     300
gttaacattc ctctatgggg tggagtagtc cagagaatta ttagttctgt taagcttagt     360
acatttctct gcggtcttga aaataaagat gttttaattt tcaatttccc gatggccaaa     420
ccattttggc atatattgtc attctttcac cgccttctaa aatttagaat agtacttctg     480
attgatgata agccttgtcg tcgtcgtcct tgcagtctga cctggtacca attgatgcat     540
cgataccggt actagtcgga ccgcatatgc ggccgctcga gcatgcatct agagggccct     600
```

| attctatagt gtcacctaaa tgctagagct cgctgatcag cctcgactgt gccttctagt | 660 |
| tgccagccat ctgttgtttg cccctccccc gtgccttcct tgaccctgg | 709 |

<210> SEQ ID NO 6
<211> LENGTH: 255
<212> TYPE: DNA
<213> ORGANISM: artificial
<220> FEATURE:
<223> OTHER INFORMATION: DNA encoding FLAG-PYC18 peptide

<400> SEQUENCE: 6

| agagctcgga tcagtatggg tagctatccc taaccctctc ctcggtctcg attctacaca | 60 |
| agctatgggt gctcctccaa aaagaagag aaaggtagc gaattcaggt cagactacaa | 120 |
| ggacgacgac gacaaggctt atcaatcaat catacattga ctacaaggac gacgacgaca | 180 |
| aggcttatca atcaatcaat ggggccctgc tgaagattca acgttcttcg cctctccttg | 240 |
| cttttgaata tcttc | 255 |

<210> SEQ ID NO 7
<211> LENGTH: 244
<212> TYPE: DNA
<213> ORGANISM: artificial
<220> FEATURE:
<223> OTHER INFORMATION: DNA encoding FLAG-PYC19 peptide
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (23)..(25)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t

<400> SEQUENCE: 7

| tngggagacc caagcttggt acnnngctcg gatccagtat gggtaagcct atncctaacc | 60 |
| ctctcctcgg tctcgattct acacaagcta tgggtgctcc tccaaaaaag aagagaaagg | 120 |
| tagctgaatt caggtcagac tacaaggacg acgacgacaa gcttatcaat caatcatacg | 180 |
| cataccctta catttactaa tattggactt attttagatg tacgtttgtt attacgttgt | 240 |
| ctct | 244 |

<210> SEQ ID NO 8
<211> LENGTH: 211
<212> TYPE: DNA
<213> ORGANISM: artificial
<220> FEATURE:
<223> OTHER INFORMATION: DNA encoding FLAG-PYC20 peptide

<400> SEQUENCE: 8

| aggtcagact acaaggacga cgacgacaag atttattcat caattctatg ggggacaaaa | 60 |
| tggtgcgttt tattggtaat aacaccctaa tctatagaga tggtgattga ttgataagcc | 120 |
| ttctcgtcgt cgtccttgta gtctgacctg gtaccaattg atgcatcgat accggtacta | 180 |
| gtcggaccgc atatgcccgg gcgtaccgcg g | 211 |

<210> SEQ ID NO 9
<211> LENGTH: 120
<212> TYPE: DNA
<213> ORGANISM: artificial

<220> FEATURE:
<223> OTHER INFORMATION: DNA encoding FLAG-PYC21 peptide
<220> FEATURE:
<221> NAME/KEY: misc_feature
<222> LOCATION: (53)..(53)
<223> OTHER INFORMATION: n is a, c, g, or t

<400> SEQUENCE: 9
aggtcagact acaaggacga cgacgacaag atcattattt atattttcct tancatctct    60
aatagcatca aaacatctt cgacaatatg ggtaaaatca gataactcca tcatatcaag    120

<210> SEQ ID NO 10
<211> LENGTH: 253
<212> TYPE: DNA
<213> ORGANISM: artificial
<220> FEATURE:
<223> OTHER INFORMATION: DNA encoding FLAG-PYC22 peptide
<220> FEATURE:
<221> NAME/KEY: misc_feature
<222> LOCATION: (64)..(65)
<223> OTHER INFORMATION: n is a, c, g, or t

<400> SEQUENCE: 10
ggtcgagctg gatcagtatg ggtaagccta tccctaaccc tctcctcggt ctcgattcta    60
cacnnttcta tgggtgctcc tccaaaaaag aagagaaagg tagctgaatt caggtcagac    120
tacaaggacg acgacgacaa gaaggactcc atacggcggc gcggcgagaa tatttcctcg    180
caggaagtcg aggccgtcct catgtcgcat cccgaagtcg tcaatgccgc ggtctacccc    240
gtacgcggcg atc                                                      253

<210> SEQ ID NO 11
<211> LENGTH: 255
<212> TYPE: DNA
<213> ORGANISM: artificial
<220> FEATURE:
<223> OTHER INFORMATION: DNA encoding FLAG-PYC24 peptide

<400> SEQUENCE: 11
tcgagctcgg atcagtatgg gtagcctatc cctaaccctc tcctcggtct cgattctaca    60
caagctatgg gtgctcctcc aaaaaagaag agaaaggtag ctgaattcag gtcagactac    120
aaggacgacg acgacaagct atatcaatca ctactcactg ctaccaaaga attgcttttt    180
gtcgcgcctg tagcaaaagc attcacatcg tgtgattgat tgataagcct tctcgtcgtc    240
gtccttgtag tctga                                                    255

<210> SEQ ID NO 12
<211> LENGTH: 247
<212> TYPE: DNA
<213> ORGANISM: artificial
<220> FEATURE:
<223> OTHER INFORMATION: DNA encoding FLAG-PYC29 peptide
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (20)..(23)
<223> OTHER INFORMATION: n is a, c, g, or t
<220> FEATURE:
<221> NAME/KEY: misc_feature
<222> LOCATION: (32)..(33)

<223> OTHER INFORMATION: n is a, c, g, or t

<400> SEQUENCE: 12

```
ggnagaccnn ncttggtacn nnnctcggat cnngtatggg taagcctatc cctaaccctc    60
tcctcggtct cgattctaca caagctatgg gtgctcctcc aaaaaagaag agaaaggtag   120
ctgaattcag gtcagactac aaggacgacg acgacaaggc ttatcaatca atcagtgtcg   180
tcgtcgtcct tgtagtctga cctggtacca attgatgcat cgataccggt actagtcgga   240
ccgcata                                                             247
```

<210> SEQ ID NO 13
<211> LENGTH: 247
<212> TYPE: DNA
<213> ORGANISM: artificial
<220> FEATURE:
<223> OTHER INFORMATION: DNA encoding FLAG-PYC30 peptide
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (21)..(23)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t

<400> SEQUENCE: 13

```
gggagacccn ngcttggtac nnngctcgga tccngtatgg gtaagcctat ccctaaccct    60
ctcctcggtc tcgattctac acaagctatg ggtgctcctc caaaaaagaa gagaaaggta   120
gctgaattca ggtcagacta caaggacgac gacgacaaga aggactccat acggcggcgc   180
ggcgagaata tttcctcgca ggaagtcgag gccgtcctca tgtcgcatcc cgaagtcgtc   240
aatgccg                                                             247
```

<210> SEQ ID NO 14
<211> LENGTH: 544
<212> TYPE: DNA
<213> ORGANISM: artificial
<220> FEATURE:
<223> OTHER INFORMATION: DNA encoding FLAG-PYC32 peptide
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (379)..(379)
<223> OTHER INFORMATION: n is a, c, g, or t
<220> FEATURE:
<221> NAME/KEY: misc_feature
<222> LOCATION: (445)..(445)
<223> OTHER INFORMATION: n is a, c, g, or t
<220> FEATURE:
<221> NAME/KEY: misc_feature
<222> LOCATION: (451)..(451)
<223> OTHER INFORMATION: n is a, c, g, or t
<220> FEATURE:
<221> NAME/KEY: misc_feature
<222> LOCATION: (465)..(465)
<223> OTHER INFORMATION: n is a, c, g, or t
<220> FEATURE:
<221> NAME/KEY: misc_feature
<222> LOCATION: (473)..(473)
<223> OTHER INFORMATION: n is a, c, g, or t
<220> FEATURE:
<221> NAME/KEY: misc_feature
<222> LOCATION: (480)..(481)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (502)..(502)
<223> OTHER INFORMATION: n is a, c, g, or t
<220> FEATURE:
<221> NAME/KEY: misc_feature
<222> LOCATION: (508)..(508)
<223> OTHER INFORMATION: n is a, c, g, or t
<220> FEATURE:
<221> NAME/KEY: misc_feature
<222> LOCATION: (512)..(512)
<223> OTHER INFORMATION: n is a, c, g, or t
<220> FEATURE:
<221> NAME/KEY: misc_feature
<222> LOCATION: (515)..(517)
<223> OTHER INFORMATION: n is a, c, g, or t
<220> FEATURE:
<221> NAME/KEY: misc_feature
<222> LOCATION: (520)..(520)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (529)..(529)
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t
<220> FEATURE:
<221> NAME/KEY: misc_feature
<222> LOCATION: (535)..(535)
<223> OTHER INFORMATION: n is a, c, g, or t
<220> FEATURE:
<221> NAME/KEY: misc_feature
<222> LOCATION: (539)..(539)
<223> OTHER INFORMATION: n is a, c, g, or t

<400> SEQUENCE: 14
gggagaccca ngcttggtac cnngctcgga tccagtatgg gtaagcctat ccctaaccct    60
ctcctcggtc tcgattctac acaagctatg ggtgctcctc caaaaaagaa gagaaaggta   120
gctgaattca ggtcagacta caaggacgac gacgacaata ccccccactc ctccgatggc   180
cacaataatc cctaaaatct cagtgttttc tccagttttt gctagaatca taggctggta   240
aattacttca gtgattcctt ctacaaagct aaacaatgat aactgattga ttgataagcc   300
ttgtcgtcgt cgtccttgta gtctgacctg gtaccaattg gtgcatcgat accggtacta   360
gtcggaccgc atatgcggnc gctcgagcat gcatctagag ggcccattc tatagtgtca   420 cctaaatgct agagctcgct gatcngcctc nactgtgcct tctanttgcc agncatctgn   480
ngtttgccct ccccgtgnct tncttgancc tngannngcn ctccnctgnc ntttnctana   540
aatg                                                                544

<210> SEQ ID NO 15
<211> LENGTH: 205
<212> TYPE: DNA
<213> ORGANISM: artificial
<220> FEATURE:

<223> OTHER INFORMATION: DNA encoding FLAG-PYC33 peptide
<220> FEATURE:
<221> NAME/KEY: misc_feature
<222> LOCATION: (192)..(192)
<223> OTHER INFORMATION: n is a, c, g, or t

<400> SEQUENCE: 15
aggtcagact acaaggacga cgacgacaag gcttatcaat caatcaaatg gccaatgtaa    60
attgtcggtg cgccaggaaa gagcgtcggt ttgtgtttgt cgatgatttt aagtgtttcg   120
agcggatcaa acttaggaag aagaatcatt taacacctgt tacagaaggg cttgtcgtcg   180
tcgtccttgt antctgacct gaatt                                         205

<210> SEQ ID NO 16
<211> LENGTH: 243
<212> TYPE: DNA
<213> ORGANISM: artificial
<220> FEATURE:
<223> OTHER INFORMATION: DNA encoding FLAG-PYC34 peptide
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 16 gggagaccen ngcttggtac cnagctcgat ccctaaccct ctcctcggtc tcgattctac    60
acaagctatg ggtgctcctc caaaaaagaa gagaaaggta gctgaattca ggtcagacta   120
caaggacgac gacgacaagg cttatcaatc aataaattcg tcaccagtat tgccagaaaa   180
tagtcaagaa ttatcacttc acttaaagca acacgtaaca aaatcatgaa agaatatatc   240
aaa                                                                  243

<210> SEQ ID NO 17
<211> LENGTH: 243
<212> TYPE: DNA
<213> ORGANISM: artificial
<220> FEATURE:
<223> OTHER INFORMATION: DNA encoding FLAG-PYC35 peptide
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (21)..(23)
<223> OTHER INFORMATION: n is a, c, g, or t

<400> SEQUENCE: 17 gggagaccen agcttggtac nnngctcgga tccagtatgg gtaagcctat ccctaaccct    60
ctcctcggtc tcgattctac acaagctatg ggtgctcctc caaaaaagaa gagaaaggta   120
gctgaattca ggtcagacta caaggacgac gacgacaagg cttatcaatc aatcaggtct   180
ggagggatag agtcgagttc gaaaagggaa aggtaggggt gggaatgacc ctaaggactt   240
aca                                                                  243

<210> SEQ ID NO 18
<211> LENGTH: 255
<212> TYPE: DNA
<213> ORGANISM: artificial
<220> FEATURE:
<223> OTHER INFORMATION: DNA encoding FLAG-PYC36 peptide

```
<400> SEQUENCE: 18
tgtcgagctc ggaccagtat gggtaagcct atccctaacc ctctcctcgg tctcgattct    60
acacaagcta tgaggtgctc ttccaaaaaa gaagagaaag gtagctgaat tcaggtcaga   120
ctacaaggac gacgacgaca agggactaca aggacgacga cgacaaggtt atcaatcaat   180
caagccatga ttgatctccg atatatgaat tcaggtcaga ctacaaggac gactttccct   240
tggaatagac tatag                                                    255

<210> SEQ ID NO 19
<211> LENGTH: 192
<212> TYPE: DNA
<213> ORGANISM: artificial
<220> FEATURE:
<223> OTHER INFORMATION: DNA encoding FLAG-PYC38 peptide

<400> SEQUENCE: 19
ctaaccctct cctcggtctc gattctacac aagctatggg tgctcctcca aaaagaaga    60 gaaaggtagc tgaattcagg tcagactaca aggacgacga cgacaaggga ctacaaggcc   120
gccgacagcc tggccaacag cctcaaggcc gctggagtgg acgcgcgctt ccagcgcatc   180
gatagccagc cg                                                       192

<210> SEQ ID NO 20
<211> LENGTH: 243
<212> TYPE: DNA
<213> ORGANISM: artificial
<220> FEATURE:
<223> OTHER INFORMATION: DNA encoding FLAG-PYC39 peptide
<220> FEATURE:
<221> NAME/KEY: misc_feature
<222> LOCATION: (22)..(24)
<223> OTHER INFORMATION: n is a, c, g, or t

<400> SEQUENCE: 20
gggagaccca agcttggtac cnnnctcgga tccagtatgg gtaagcctat ccctaaccct    60
ctcctcggtc tcgattctac acaagctatg ggtgctcctc caaaaaagaa gagaaaggta   120
gctgaattca ggtcagacta caaggacgac gacgacaagg gactacaagg ccgccgacag   180
cctggccaac agcctcaagg ccgctggagt ggacgcgcgc ttccagcgca tcgatagcca   240
gcc                                                                 243

<210> SEQ ID NO 21
<211> LENGTH: 614
<212> TYPE: DNA
<213> ORGANISM: artificial
<220> FEATURE:
<223> OTHER INFORMATION: DNA encoding FLAG-PYC54 peptide
<220> FEATURE:
<221> NAME/KEY: misc_feature
<222> LOCATION: (22)..(24)
<223> OTHER INFORMATION: n is a, c, g, or t
<220> FEATURE:
<221> NAME/KEY: misc_feature
<222> LOCATION: (30)..(36)
<223> OTHER INFORMATION: n is a, c, g, or t
<220> FEATURE:
<221> NAME/KEY: misc_feature
<222> LOCATION: (50)..(53)
<223> OTHER INFORMATION: n is a, c, g, or t
<220> FEATURE:
<221> NAME/KEY: misc_feature
<222> LOCATION: (346)..(346)
<223> OTHER INFORMATION: n is a, c, g, or t
<220> FEATURE:
```

```
<221> NAME/KEY: misc_feature
<222> LOCATION: (363)..(363)
<223> OTHER INFORMATION: n is a, c, g, or t
<220> FEATURE:
<221> NAME/KEY: misc_feature
<222> LOCATION: (377)..(377)
<223> OTHER INFORMATION: n is a, c, g, or t
<220> FEATURE:
<221> NAME/KEY: misc_feature
<222> LOCATION: (410)..(410)
<223> OTHER INFORMATION: n is a, c, g, or t
<220> FEATURE:
<221> NAME/KEY: misc_feature
<222> LOCATION: (604)..(604)
<223> OTHER INFORMATION: n is a, c, g, or t

<400> SEQUENCE: 21
gggagaccca agcttggtac cnnnctcggn nnnnnnatgg gtaagcctan nnntaaccct      60
ctcctcggtc tcgattctac acaagctatg ggtgctcctc caaaaaagaa gagaaaggta    120
gctgaattca ggtcagacta caaggacgac gacgacaagg cttatcaatc aatcagcttg    180
gcaggctacc acggcgacac ttcgagaaca tttctagtgg gttcggtatc cgcaactgcc    240
cgaaaattag ttgaagcgac tcaagaaacg atgattgatt atacttgtcg tcgtcgtcct    300
tgtagtctga cctggtacca attgatgcat cgataccggt actagncgga ccgcatatgc    360
ggncgctcga gcatgcntct agagggccct attctatagt gtcacctaan tgctagagct    420
cgctgatcag cctcgactgt gccttctagt tgccagccat ctgttgtttg ccctcccccc    480
gtgccttcct tgaccctgga aggtgccact cccactgtcc tttcctaata aaatgaggaa    540
attgcatcgc attgtctgag taggtgtcat tctattctgg ggggtggggt ggggcaggac    600
agcnaggggg agga                                                      614

<210> SEQ ID NO 22
<211> LENGTH: 323
<212> TYPE: DNA
<213> ORGANISM: artificial
<220> FEATURE:
<223> OTHER INFORMATION: DNA encoding FLAG-PYC58 peptide

<400> SEQUENCE: 22
aggtcagact acaaggacga cgacgacaag gcttatcaat caatcatggc agtggctgcc     60
cagcagccgg tcgcgttcct ggtaggccgc cagcgtcgcc gcggtcaggt aggaatcgac    120
tccggcgatc agcaccttcg aacacccctg ttccatgagc tttgtcgtcg tcgtccttgt    180
agtctggcct ggtaccaatt gatgcatcga taccggtact agtcggaccg catatgcccg    240
ggcgtaccgc ggccgctcga ggcatgcatc tagagggccg catcatgtaa ttagttatgt    300
cacgcttaca ttcacgccct ccc                                            323

<210> SEQ ID NO 23
<211> LENGTH: 220
<212> TYPE: DNA
<213> ORGANISM: artificial
<220> FEATURE:
<223> OTHER INFORMATION: DNA encoding FLAG-PYC59 peptide
<220> FEATURE:
<221> NAME/KEY: misc_feature
<222> LOCATION: (189)..(189)
<223> OTHER INFORMATION: n is a, c, g, or t

<400> SEQUENCE: 23
gctcggatcc agtatgggta agcctatccc taaccctctc ctcggtctcg attctacaca     60
agctatgggt gctcctccaa aaagaagag aaaggtagct gaattcaggt cagactacaa    120
```

```
ggacgacgac gacaaggctt atcaatcaat cagtgtcgtc gtcgtccttg tagtctgacc    180
tggtaccant tgatgcatcg ataccggtac tagtcggacc                          220
```

<210> SEQ ID NO 24
<211> LENGTH: 253
<212> TYPE: DNA
<213> ORGANISM: artificial
<220> FEATURE:
<223> OTHER INFORMATION: DNA encoding FLAG-PYC60 peptide

<400> SEQUENCE: 24

```
aggtcagact acaaggacga cgacgacaag gctaatcaat tgcccaaaat acttgctgga    60
cggcttatat ttataaagtg ctaactgcgc ttgattgatt gataagcttc tcgtcgtcgt   120
ccttgtagtc tgacctggta ccaattgatg catcgatacc ggtactagtc ggaccgcata   180
tgcccgggcg taccgcggcc gctcgaggca tgcatctaga gggccgcatc atgtaattag   240
ttatgtcacg ctt                                                      253
```

<210> SEQ ID NO 25
<211> LENGTH: 255
<212> TYPE: DNA
<213> ORGANISM: artificial
<220> FEATURE:
<223> OTHER INFORMATION: DNA encoding FLAG-PYC66 peptide

<400> SEQUENCE: 25

```
gtcgagctcg gatcagtatg ggtagcctat ccctaaccct ctcctcggtc tcgattctac    60
acaagctatg ggtgctcctc caaaaaagaa gagaaaggta gctgaattca ggtcagacta   120
caaggacgac gacgacaagg cttatcaatc aatcataggg gcgggaaaat caacgctaat   180
caaagcatta actggcgtat accacgccga tcgcggcacc atctggctgg aaggccaggc   240
tatctcaccg aaaaa                                                    255
```

<210> SEQ ID NO 26
<211> LENGTH: 15
<212> TYPE: PRT
<213> ORGANISM: artificial
<220> FEATURE:
<223> OTHER INFORMATION: FLAG-PYC4 peptide

<400> SEQUENCE: 26

Arg Ser Asp Tyr Lys Asp Asp Asp Lys Ala Tyr Gln Ser Met
1               5                   10                  15

<210> SEQ ID NO 27
<211> LENGTH: 5
<212> TYPE: PRT
<213> ORGANISM: artificial
<220> FEATURE:
<223> OTHER INFORMATION: PYC4 peptide

<400> SEQUENCE: 27

Ala Tyr Gln Ser Met
1               5

<210> SEQ ID NO 28
<211> LENGTH: 17
<212> TYPE: PRT
<213> ORGANISM: artificial
<220> FEATURE:
<223> OTHER INFORMATION: FLAG-PYC6 peptide

```
<400> SEQUENCE: 28

Arg Ser Asp Tyr Lys Asp Asp Asp Lys Ala Tyr Gln Ser Lys Arg
1               5                   10                  15

Leu

<210> SEQ ID NO 29
<211> LENGTH: 7
<212> TYPE: PRT
<213> ORGANISM: artificial
<220> FEATURE:
<223> OTHER INFORMATION: PYC6 peptide

<400> SEQUENCE: 29

Ala Tyr Gln Ser Lys Arg Leu
1               5

<210> SEQ ID NO 30
<211> LENGTH: 39
<212> TYPE: PRT
<213> ORGANISM: artificial
<220> FEATURE:
<223> OTHER INFORMATION: FLAG-PYC8 peptide

<400> SEQUENCE: 30

Arg Ser Asp Tyr Lys Asp Asp Asp Lys Ala Tyr Gln Ser Ile Ile
1               5                   10                  15

Ala Asn Glu Glu Glu Arg Glu Lys Asn Phe Ala Ser Ser Lys Lys Asp
                20                  25                  30

Gly Ser Tyr Thr Asp Leu Leu
            35

<210> SEQ ID NO 31
<211> LENGTH: 29
<212> TYPE: PRT
<213> ORGANISM: artificial
<220> FEATURE:
<223> OTHER INFORMATION: PYC8 peptide

<400> SEQUENCE: 31

Ala Tyr Gln Ser Ile Ile Ala Asn Glu Glu Glu Arg Glu Lys Asn Phe
1               5                   10                  15

Ala Ser Ser Lys Lys Asp Gly Ser Tyr Thr Asp Leu Leu
                20                  25

<210> SEQ ID NO 32
<211> LENGTH: 40
<212> TYPE: PRT
<213> ORGANISM: artificial
<220> FEATURE:
<223> OTHER INFORMATION: FLAG-PYC12 peptide

<400> SEQUENCE: 32

Arg Ser Asp Tyr Lys Asp Asp Asp Lys Ala Tyr Gln Glu Ser Thr
1               5                   10                  15

Lys Ala Leu Val Glu Gly Gly Ala Asp Leu Ile Leu Ile Glu Thr Val
                20                  25                  30

Leu Val Val Val Leu Val Val
            35                  40

<210> SEQ ID NO 33
<211> LENGTH: 30
<212> TYPE: PRT
<213> ORGANISM: artificial
```

```
<220> FEATURE:
<223> OTHER INFORMATION: PYC12 peptide

<400> SEQUENCE: 33

Ala Tyr Gln Glu Ser Thr Lys Ala Leu Val Glu Gly Gly Ala Asp Leu
 1               5                  10                  15
Ile Leu Ile Glu Thr Val Leu Val Val Val Leu Val Val
            20                  25                  30

<210> SEQ ID NO 34
<211> LENGTH: 141
<212> TYPE: PRT
<213> ORGANISM: artificial
<220> FEATURE:
<223> OTHER INFORMATION: FLAG-PYC15 peptide

<400> SEQUENCE: 34

Arg Ser Asp Tyr Lys Asp Asp Asp Lys Thr Tyr Gln Ser Ile Lys
 1               5                  10                  15
Gly Pro Glu Asn Lys Val Lys Met Tyr Phe Leu Asn Asp Leu Asn Phe
            20                  25                  30
Ser Arg Arg Asp Ala Gly Phe Lys Ala Arg Lys Asp Ala Leu Asp Ile
        35                  40                  45
Ala Ser Asp Tyr Glu Asn Ile Ser Val Val Asn Ile Pro Leu Trp Gly
    50                  55                  60
Gly Val Val Gln Arg Ile Ser Ser Val Lys Leu Ser Thr Phe Leu
65                  70                  75                  80
Cys Gly Leu Glu Asn Lys Asp Val Leu Ile Phe Asn Phe Pro Met Ala
                85                  90                  95
Lys Pro Phe Trp His Ile Leu Ser Phe Phe His Arg Leu Leu Lys Phe
            100                 105                 110
Arg Ile Val Leu Leu Ile Asp Asp Lys Pro Cys Arg Arg Pro Cys
        115                 120                 125
Ser Leu Thr Trp Tyr Gln Leu Met His Arg Tyr Arg Tyr
    130                 135                 140

<210> SEQ ID NO 35
<211> LENGTH: 131
<212> TYPE: PRT
<213> ORGANISM: artificial
<220> FEATURE:
<223> OTHER INFORMATION: PYC15 peptide

<400> SEQUENCE: 35

Thr Tyr Gln Ser Ile Lys Gly Pro Glu Asn Lys Val Lys Met Tyr Phe
 1               5                  10                  15
Leu Asn Asp Leu Asn Phe Ser Arg Arg Asp Ala Gly Phe Lys Ala Arg
            20                  25                  30
Lys Asp Ala Leu Asp Ile Ala Ser Asp Tyr Glu Asn Ile Ser Val Val
        35                  40                  45
Asn Ile Pro Leu Trp Gly Gly Val Val Gln Arg Ile Ile Ser Ser Val
    50                  55                  60
Lys Leu Ser Thr Phe Leu Cys Gly Leu Glu Asn Lys Asp Val Leu Ile
65                  70                  75                  80
Phe Asn Phe Pro Met Ala Lys Pro Phe Trp His Ile Leu Ser Phe Phe
                85                  90                  95
His Arg Leu Leu Lys Phe Arg Ile Val Leu Leu Ile Asp Asp Lys Pro
            100                 105                 110
```

```
Cys Arg Arg Arg Pro Cys Ser Leu Thr Trp Tyr Gln Leu Met His Arg
        115                 120                 125

Tyr Arg Tyr
    130

<210> SEQ ID NO 36
<211> LENGTH: 17
<212> TYPE: PRT
<213> ORGANISM: artificial
<220> FEATURE:
<223> OTHER INFORMATION: FLAG-PYC18 peptide

<400> SEQUENCE: 36

Arg Ser Asp Tyr Lys Asp Asp Asp Lys Ala Tyr Gln Ser Ile Ile
1               5                   10                  15

His

<210> SEQ ID NO 37
<211> LENGTH: 7
<212> TYPE: PRT
<213> ORGANISM: artificial
<220> FEATURE:
<223> OTHER INFORMATION: PYC18 peptide

<400> SEQUENCE: 37

Ala Tyr Gln Ser Ile Ile His
1               5

<210> SEQ ID NO 38
<211> LENGTH: 22
<212> TYPE: PRT
<213> ORGANISM: artificial
<220> FEATURE:
<223> OTHER INFORMATION: FLAG-PYC19 peptide

<400> SEQUENCE: 38

Arg Ser Asp Tyr Lys Asp Asp Asp Lys Leu Ile Asn Gln Ser Tyr
1               5                   10                  15

Ala Tyr Pro Tyr Ile Tyr
            20

<210> SEQ ID NO 39
<211> LENGTH: 12
<212> TYPE: PRT
<213> ORGANISM: artificial
<220> FEATURE:
<223> OTHER INFORMATION: PYC19 peptide

<400> SEQUENCE: 39

Leu Ile Asn Gln Ser Tyr Ala Tyr Pro Tyr Ile Tyr
1               5                   10

<210> SEQ ID NO 40
<211> LENGTH: 29
<212> TYPE: PRT
<213> ORGANISM: artificial
<220> FEATURE:
<223> OTHER INFORMATION: FLAG-PYC20 peptide

<400> SEQUENCE: 40

Arg Ser Asp Tyr Lys Asp Asp Asp Lys Ile Tyr Ser Ser Ile Leu
1               5                   10                  15

Trp Gly Thr Lys Trp Cys Val Leu Leu Val Ile Thr Pro
            20                  25
```

<210> SEQ ID NO 41
<211> LENGTH: 19
<212> TYPE: PRT
<213> ORGANISM: artificial
<220> FEATURE:
<223> OTHER INFORMATION: PYC20 peptide

<400> SEQUENCE: 41

Ile Tyr Ser Ser Ile Leu Trp Gly Thr Lys Trp Cys Val Leu Leu Val
1               5                   10                  15

Ile Thr Pro

<210> SEQ ID NO 42
<211> LENGTH: 34
<212> TYPE: PRT
<213> ORGANISM: artificial
<220> FEATURE:
<223> OTHER INFORMATION: FLAG-PYC21 peptide

<400> SEQUENCE: 42

Arg Ser Asp Tyr Lys Asp Asp Asp Lys Ile Ile Ile Tyr Ile Phe
1               5                   10                  15

Leu Asn Ile Ser Asn Ser Ile Lys Asn Ile Phe Asp Asn Met Gly Lys
                20                  25                  30

Ile Arg

<210> SEQ ID NO 43
<211> LENGTH: 24
<212> TYPE: PRT
<213> ORGANISM: artificial
<220> FEATURE:
<223> OTHER INFORMATION: PYC21 peptide

<400> SEQUENCE: 43

Ile Ile Ile Tyr Ile Phe Leu Asn Ile Ser Asn Ser Ile Lys Asn Ile
1               5                   10                  15

Phe Asp Asn Met Gly Lys Ile Arg
                20

<210> SEQ ID NO 44
<211> LENGTH: 51
<212> TYPE: PRT
<213> ORGANISM: artificial
<220> FEATURE:
<223> OTHER INFORMATION: FLAG-PYC22 peptide

<400> SEQUENCE: 44

Arg Ser Asp Tyr Lys Asp Asp Asp Lys Lys Asp Ser Ile Arg Arg
1               5                   10                  15

Arg Gly Glu Asn Ile Ser Ser Gln Glu Val Gly Ala Val Leu Met Ser
                20                  25                  30

His Pro Glu Val Val Asn Ala Ala Val Tyr Pro Val Arg Gly Asp Leu
            35                  40                  45

Pro Gly Asp
    50

<210> SEQ ID NO 45
<211> LENGTH: 41
<212> TYPE: PRT
<213> ORGANISM: artificial
<220> FEATURE:
<223> OTHER INFORMATION: PYC22 peptide

```
<400> SEQUENCE: 45

Lys Asp Ser Ile Arg Arg Gly Glu Asn Ile Ser Ser Gln Glu Val
1               5                   10                  15

Glu Ala Val Leu Met Ser His Pro Glu Val Val Asn Ala Ala Val Tyr
            20                  25                  30

Pro Val Arg Gly Asp Leu Pro Gly Asp
        35                  40

<210> SEQ ID NO 46
<211> LENGTH: 36
<212> TYPE: PRT
<213> ORGANISM: artificial
<220> FEATURE:
<223> OTHER INFORMATION: FLAG-PYC24 peptide

<400> SEQUENCE: 46

Arg Ser Asp Tyr Lys Asp Asp Asp Lys Leu Tyr Gln Ser Leu Leu
1               5                   10                  15

Thr Ala Thr Lys Glu Leu Leu Phe Val Ala Pro Val Ala Lys Ala Phe
            20                  25                  30

Thr Ser Cys Asp
        35

<210> SEQ ID NO 47
<211> LENGTH: 26
<212> TYPE: PRT
<213> ORGANISM: artificial
<220> FEATURE:
<223> OTHER INFORMATION: PYC24 peptide

<400> SEQUENCE: 47

Leu Tyr Gln Ser Leu Leu Thr Ala Thr Lys Glu Leu Leu Phe Val Ala
1               5                   10                  15

Pro Val Ala Lys Ala Phe Thr Ser Cys Asp
            20                  25

<210> SEQ ID NO 48
<211> LENGTH: 20
<212> TYPE: PRT
<213> ORGANISM: artificial
<220> FEATURE:
<223> OTHER INFORMATION: FLAG-PYC29 peptide

<400> SEQUENCE: 48

Arg Ser Asp Tyr Lys Asp Asp Asp Lys Ala Tyr Gln Ser Ile Ser
1               5                   10                  15

Phe Leu Ser Gln
        20

<210> SEQ ID NO 49
<211> LENGTH: 10
<212> TYPE: PRT
<213> ORGANISM: artificial
<220> FEATURE:
<223> OTHER INFORMATION: PYC29 peptide

<400> SEQUENCE: 49

Ala Tyr Gln Ser Ile Ser Phe Leu Ser Gln
1               5                   10

<210> SEQ ID NO 50
<211> LENGTH: 51
<212> TYPE: PRT
```

<213> ORGANISM: artificial
<220> FEATURE:
<223> OTHER INFORMATION: FLAG-PYC30 peptide

<400> SEQUENCE: 50

Arg Ser Asp Tyr Lys Asp Asp Asp Lys Asp Ser Ile Arg Arg
1               5                   10                  15

Arg Gly Glu Asn Ile Ser Ser Gln Glu Val Glu Ala Val Leu Met Ser
            20                  25                  30

His Pro Glu Val Val Asn Ala Ala Val Tyr Pro Val Arg Gly Asp Leu
        35                  40                  45

Pro Gly Asp
    50

<210> SEQ ID NO 51
<211> LENGTH: 41
<212> TYPE: PRT
<213> ORGANISM: artificial
<220> FEATURE:
<223> OTHER INFORMATION: PYC30 peptide

<400> SEQUENCE: 51

Lys Asp Ser Ile Arg Arg Arg Gly Glu Asn Ile Ser Ser Gln Glu Val
1               5                   10                  15

Glu Ala Val Leu Met Ser His Pro Glu Val Val Asn Ala Ala Val Tyr
            20                  25                  30

Pro Val Arg Gly Asp Leu Pro Gly Asp
        35                  40

<210> SEQ ID NO 52
<211> LENGTH: 21
<212> TYPE: PRT
<213> ORGANISM: artificial
<220> FEATURE:
<223> OTHER INFORMATION: FLAG-PYC32 peptide

<400> SEQUENCE: 52

Arg Ser Asp Tyr Lys Asp Asp Asp Asn Thr Pro His Ser Ser Asp
1               5                   10                  15

Gly His Asn Asn Pro
            20

<210> SEQ ID NO 53
<211> LENGTH: 12
<212> TYPE: PRT
<213> ORGANISM: artificial
<220> FEATURE:
<223> OTHER INFORMATION: PYC32 peptide

<400> SEQUENCE: 53

Asn Thr Pro His Ser Ser Asp Gly His Asn Asn Pro
1               5                   10

<210> SEQ ID NO 54
<211> LENGTH: 39
<212> TYPE: PRT
<213> ORGANISM: artificial
<220> FEATURE:
<223> OTHER INFORMATION: FLAG-PYC34 peptide

<400> SEQUENCE: 54

Arg Ser Asp Tyr Lys Asp Asp Asp Lys Ala Tyr Gln Ser Ile Asn
1               5                   10                  15

Ser Ser Pro Val Leu Pro Glu Asn Ser Gln Glu Leu Ser Leu His Leu
            20                  25                  30

Lys Gln His Val Thr Lys Ser
        35

<210> SEQ ID NO 55
<211> LENGTH: 29
<212> TYPE: PRT
<213> ORGANISM: artificial
<220> FEATURE:
<223> OTHER INFORMATION: PYC34 peptide

<400> SEQUENCE: 55

Ala Tyr Gln Ser Ile Asn Ser Ser Pro Val Leu Pro Glu Asn Ser Gln
1               5                  10                  15

Glu Leu Ser Leu His Leu Lys Gln His Val Thr Lys Ser
            20                  25

<210> SEQ ID NO 56
<211> LENGTH: 28
<212> TYPE: PRT
<213> ORGANISM: artificial
<220> FEATURE:
<223> OTHER INFORMATION: FLAG-PYC35 peptide

<400> SEQUENCE: 56

Arg Ser Asp Tyr Lys Asp Asp Asp Lys Ala Tyr Gln Ser Ile Arg
1               5                  10                  15

Ser Gly Gly Ile Glu Ser Ser Ser Lys Arg Glu Arg
            20                  25

<210> SEQ ID NO 57
<211> LENGTH: 18
<212> TYPE: PRT
<213> ORGANISM: artificial
<220> FEATURE:
<223> OTHER INFORMATION: PYC35 peptide

<400> SEQUENCE: 57

Ala Tyr Gln Ser Ile Arg Ser Gly Gly Ile Glu Ser Ser Ser Lys Arg
1               5                  10                  15

Glu Arg

<210> SEQ ID NO 58
<211> LENGTH: 25
<212> TYPE: PRT
<213> ORGANISM: artificial
<220> FEATURE:
<223> OTHER INFORMATION: FLAG-PYC36 peptide

<400> SEQUENCE: 58

Arg Ser Asp Tyr Lys Asp Asp Asp Lys Gly Leu Gln Gly Arg Arg
1               5                  10                  15

Arg Gln Gly Tyr Gln Ser Ile Lys Pro
            20                  25

<210> SEQ ID NO 59
<211> LENGTH: 15
<212> TYPE: PRT
<213> ORGANISM: artificial
<220> FEATURE:
<223> OTHER INFORMATION: PYC36 peptide

<400> SEQUENCE: 59

Gly Leu Gln Gly Arg Arg Gln Gly Tyr Gln Ser Ile Lys Pro
1               5                   10                  15

<210> SEQ ID NO 60
<211> LENGTH: 35
<212> TYPE: PRT
<213> ORGANISM: artificial
<220> FEATURE:
<223> OTHER INFORMATION: FLAG-PYC38 peptide

<400> SEQUENCE: 60

Arg Ser Asp Tyr Lys Asp Asp Asp Lys Gly Leu Gln Gly Arg Arg
1               5                   10                  15

Gln Pro Gly Gln Gln Pro Gln Gly Arg Trp Ser Gly Arg Ala Leu Pro
                20                  25                  30

Ala His Arg
        35

<210> SEQ ID NO 61
<211> LENGTH: 25
<212> TYPE: PRT
<213> ORGANISM: artificial
<220> FEATURE:
<223> OTHER INFORMATION: FLAG-PYC38 peptide

<400> SEQUENCE: 61

Gly Leu Gln Gly Arg Arg Gln Pro Gly Gln Gln Pro Gln Gly Arg Trp
1               5                   10                  15

Ser Gly Arg Ala Leu Pro Ala His Arg
            20                  25

<210> SEQ ID NO 62
<211> LENGTH: 35
<212> TYPE: PRT
<213> ORGANISM: artificial
<220> FEATURE:
<223> OTHER INFORMATION: FLAG-PYC39 peptide

<400> SEQUENCE: 62

Arg Ser Asp Tyr Lys Asp Asp Asp Lys Gly Leu Gln Gly Arg Arg
1               5                   10                  15

Gln Pro Gly Gln Gln Pro Gln Gly Arg Trp Ser Gly Arg Ala Leu Pro
                20                  25                  30

Ala His Arg
        35

<210> SEQ ID NO 63
<211> LENGTH: 25
<212> TYPE: PRT
<213> ORGANISM: artificial
<220> FEATURE:
<223> OTHER INFORMATION: PYC39 peptide

<400> SEQUENCE: 63

Gly Leu Gln Gly Arg Arg Gln Pro Gly Gln Gln Pro Gln Gly Arg Trp
1               5                   10                  15

Ser Gly Arg Ala Leu Pro Ala His Arg
            20                  25

<210> SEQ ID NO 64
<211> LENGTH: 71
<212> TYPE: PRT
<213> ORGANISM: artificial
<220> FEATURE:

<223> OTHER INFORMATION: FLAG-PYC54 peptide

<400> SEQUENCE: 64

Arg Ser Asp Tyr Lys Asp Asp Asp Lys Ala Tyr Gln Ser Ile Ser
1               5                   10                  15

Leu Ala Gly Tyr His Gly Asp Thr Ser Arg Thr Phe Leu Val Gly Ser
            20                  25                  30

Val Ser Ala Thr Ala Arg Lys Leu Val Glu Ala Thr Gln Glu Thr Met
        35                  40                  45

Ile Asp Tyr Thr Cys Arg Arg Arg Pro Cys Ser Leu Thr Trp Tyr Gln
50                  55                  60

Leu Met His Arg Tyr Arg Tyr
65                  70

<210> SEQ ID NO 65
<211> LENGTH: 61
<212> TYPE: PRT
<213> ORGANISM: artificial
<220> FEATURE:
<223> OTHER INFORMATION: PYC54 peptide

<400> SEQUENCE: 65

Ala Tyr Gln Ser Ile Ser Leu Ala Gly Tyr His Gly Asp Thr Ser Arg
1               5                   10                  15

Thr Phe Leu Val Gly Ser Val Ser Ala Thr Ala Arg Lys Leu Val Glu
            20                  25                  30

Ala Thr Gln Glu Thr Met Ile Asp Tyr Thr Cys Arg Arg Arg Pro Cys
        35                  40                  45

Ser Leu Thr Trp Tyr Gln Leu Met His Arg Tyr Arg Tyr
50                  55                  60

<210> SEQ ID NO 66
<211> LENGTH: 73
<212> TYPE: PRT
<213> ORGANISM: artificial
<220> FEATURE:
<223> OTHER INFORMATION: FLAG-PYC58 peptide

<400> SEQUENCE: 66

Arg Ser Asp Tyr Lys Asp Asp Asp Lys Ala Tyr Gln Ser Ile Met
1               5                   10                  15

Ala Val Ala Ala Gln Gln Pro Val Ala Phe Leu Val Gly Arg Gln Arg
            20                  25                  30

Arg Arg Gly Gln Val Gly Ile Asp Ser Gly Asp Gln His Leu Arg Thr
        35                  40                  45

Pro Leu Phe His Glu Leu Cys Arg Arg Arg Pro Cys Ser Leu Ala Trp
50                  55                  60

Tyr Gln Leu Met His Arg Tyr Arg Tyr
65                  70

<210> SEQ ID NO 67
<211> LENGTH: 63
<212> TYPE: PRT
<213> ORGANISM: artificial
<220> FEATURE:
<223> OTHER INFORMATION: PYC58 peptide

<400> SEQUENCE: 67

Ala Tyr Gln Ser Ile Met Ala Val Ala Ala Gln Gln Pro Val Ala Phe
1               5                   10                  15

```
Leu Val Gly Arg Gln Arg Arg Gly Gln Val Gly Ile Asp Ser Gly
            20                  25                  30

Asp Gln His Leu Arg Thr Pro Leu Phe His Glu Leu Cys Arg Arg
        35                  40                  45

Pro Cys Ser Leu Ala Trp Tyr Gln Leu Met His Arg Tyr Arg Tyr
    50                  55                  60

<210> SEQ ID NO 68
<211> LENGTH: 23
<212> TYPE: PRT
<213> ORGANISM: artificial
<220> FEATURE:
<223> OTHER INFORMATION: FLAG-PYC59 peptide

<400> SEQUENCE: 68

Arg Ser Asp Tyr Lys Asp Asp Asp Lys Ala Tyr Gln Ser Ile Ser
1               5                   10                  15

Val Val Val Val Leu Val Val
            20

<210> SEQ ID NO 69
<211> LENGTH: 13
<212> TYPE: PRT
<213> ORGANISM: artificial
<220> FEATURE:
<223> OTHER INFORMATION: PYC59 peptide

<400> SEQUENCE: 69

Ala Tyr Gln Ser Ile Ser Val Val Val Val Leu Val Val
1               5                   10

<210> SEQ ID NO 70
<211> LENGTH: 27
<212> TYPE: PRT
<213> ORGANISM: artificial
<220> FEATURE:
<223> OTHER INFORMATION: FLAG-PYC60 peptide

<400> SEQUENCE: 70

Arg Ser Asp Tyr Lys Asp Asp Asp Lys Ala Asn Gln Leu Pro Lys
1               5                   10                  15

Ile Leu Ala Gly Arg Leu Ile Phe Ile Lys Cys
            20                  25

<210> SEQ ID NO 71
<211> LENGTH: 17
<212> TYPE: PRT
<213> ORGANISM: artificial
<220> FEATURE:
<223> OTHER INFORMATION: PYC60 peptide

<400> SEQUENCE: 71

Ala Asn Gln Leu Pro Lys Ile Leu Ala Gly Arg Leu Ile Phe Ile Lys
1               5                   10                  15

Cys

<210> SEQ ID NO 72
<211> LENGTH: 74
<212> TYPE: PRT
<213> ORGANISM: artificial
<220> FEATURE:
<223> OTHER INFORMATION: FLAG-PYC66 peptide

<400> SEQUENCE: 72
```

```
Arg Ser Asp Tyr Lys Asp Asp Asp Lys Ala Tyr Gln Ser Ile Ile
1               5                   10                  15

Gly Ala Gly Lys Ser Thr Leu Ile Lys Ala Leu Thr Val Tyr His
            20                  25                  30

Ala Asp Arg Gly Thr Ile Trp Leu Glu Gly Gln Ala Ile Ser Pro Lys
        35                  40                  45

Asn Thr Ala His Ala Gln Gln Cys Arg Arg Arg Pro Cys Ser Leu Thr
    50                  55                  60

Trp Tyr Gln Leu Met His Arg Tyr Arg Tyr
65                  70
```

<210> SEQ ID NO 73
<211> LENGTH: 5
<212> TYPE: PRT
<213> ORGANISM: artificial
<220> FEATURE:
<223> OTHER INFORMATION: PYC4D peptide (the retroinverted form of PYC4
      peptide all amino acids other than glycine are D-amino acids)

<400> SEQUENCE: 73

```
Met Ser Gln Tyr Ala
1               5
```

<210> SEQ ID NO 74
<211> LENGTH: 16
<212> TYPE: PRT
<213> ORGANISM: artificial
<220> FEATURE:
<223> OTHER INFORMATION: PYC4D-TAT peptide (the retroinverted form of
      PYC4 peptide comprising an N-terminal tat basic region protein
      transduction domain wherein all amino acids other than glycine are
      D-amino acids)

<400> SEQUENCE: 74

```
Met Ser Gln Tyr Ala Gly Arg Arg Gln Arg Arg Lys Lys Arg Gly
1               5                   10                  15
```

<210> SEQ ID NO 75
<211> LENGTH: 7
<212> TYPE: PRT
<213> ORGANISM: artificial
<220> FEATURE:
<223> OTHER INFORMATION: PYC6D peptide (the retroinverted form of PYC4
      peptide all amino acids other than glycine are D-amino acids)

<400> SEQUENCE: 75

```
Leu Arg Lys Ser Gln Tyr Ala
1               5
```

<210> SEQ ID NO 76
<211> LENGTH: 18
<212> TYPE: PRT
<213> ORGANISM: artificial
<220> FEATURE:
<223> OTHER INFORMATION: PYC6D-TAT peptide (the retroinverted form of
      PYC6 peptide comprising an N-terminal tat basic region protein
      transduction domain wherein all amino acids other than glycine are
      D-amino acids)

<400> SEQUENCE: 76

```
Leu Arg Lys Ser Gln Tyr Ala Gly Arg Arg Arg Gln Arg Arg Lys Lys
1               5                   10                  15

Arg Gly
```

<210> SEQ ID NO 77

```
<211> LENGTH: 29
<212> TYPE: PRT
<213> ORGANISM: artificial
<220> FEATURE:
<223> OTHER INFORMATION: PYC8D peptide (the retroinverted form of PYC8
      peptide all amino acids other than glycine are D-amino acids)

<400> SEQUENCE: 77

Leu Leu Asp Thr Tyr Ser Gly Asp Lys Lys Ser Ser Ala Phe Asn Lys
1               5                   10                  15

Glu Arg Glu Glu Glu Asn Ala Ile Ile Ser Gln Tyr Ala
            20                  25

<210> SEQ ID NO 78
<211> LENGTH: 40
<212> TYPE: PRT
<213> ORGANISM: artificial
<220> FEATURE:
<223> OTHER INFORMATION: PYC8D-TAT peptide (the retroinverted form of
      PYC8 peptide comprising an N-terminal tat basic region protein
      transduction domain wherein all amino acids other than glycine are
      D-amino acids)

<400> SEQUENCE: 78

Leu Leu Asp Thr Tyr Ser Gly Asp Lys Lys Ser Ser Ala Phe Asn Lys
1               5                   10                  15

Glu Arg Glu Glu Glu Asn Ala Ile Ile Ser Gln Tyr Ala Gly Arg Arg
            20                  25                  30

Arg Gln Arg Arg Lys Lys Arg Gly
        35                  40

<210> SEQ ID NO 79
<211> LENGTH: 30
<212> TYPE: PRT
<213> ORGANISM: artificial
<220> FEATURE:
<223> OTHER INFORMATION: PYC12D peptide (the retroinverted form of PYC12
      peptide all amino acids other than glycine are D-amino acids)

<400> SEQUENCE: 79

Val Val Leu Val Val Val Val Leu Val Thr Glu Ile Leu Ile Leu Asp
1               5                   10                  15

Ala Gly Gly Glu Val Leu Ala Lys Thr Ser Glu Gln Tyr Ala
            20                  25                  30

<210> SEQ ID NO 80
<211> LENGTH: 41
<212> TYPE: PRT
<213> ORGANISM: artificial
<220> FEATURE:
<223> OTHER INFORMATION: PYC12D-TAT peptide (the retroinverted form of
      PYC12 peptide comprising an N-terminal tat basic region protein
      transduction domain wherein all amino acids other than glycine are
      D-amino acids)

<400> SEQUENCE: 80

Val Val Leu Val Val Val Val Leu Val Thr Glu Ile Leu Ile Leu Asp
1               5                   10                  15

Ala Gly Gly Glu Val Leu Ala Lys Thr Ser Glu Gln Tyr Ala Gly Arg
            20                  25                  30

Arg Arg Gln Arg Arg Lys Lys Arg Gly
        35                  40

<210> SEQ ID NO 81
<211> LENGTH: 131
```

```
<212> TYPE: PRT
<213> ORGANISM: artificial
<220> FEATURE:
<223> OTHER INFORMATION: PYC15D peptide (the retroinverted form of PYC15
      peptide all amino acids other than glycine are D-amino acids)

<400> SEQUENCE: 81

Tyr Arg Tyr Arg His Met Leu Gln Tyr Trp Thr Leu Ser Cys Pro Arg
1               5                   10                  15

Arg Arg Cys Pro Lys Asp Asp Ile Leu Leu Val Ile Arg Phe Lys Leu
                20                  25                  30

Leu Arg His Phe Phe Ser Leu Ile His Trp Phe Pro Lys Ala Met Pro
            35                  40                  45

Phe Asn Phe Ile Leu Val Asp Lys Asn Glu Leu Gly Cys Leu Phe Thr
    50                  55                  60

Ser Leu Lys Val Ser Ser Ile Ile Arg Gln Val Val Gly Gly Trp Leu
65                  70                  75                  80

Pro Ile Asn Val Val Ser Ile Asn Glu Tyr Asp Ser Ala Ile Asp Leu
                85                  90                  95

Ala Asp Lys Arg Ala Lys Phe Gly Ala Asp Arg Arg Ser Phe Asn Leu
                100                 105                 110

Asp Asn Leu Phe Tyr Met Lys Val Lys Asn Glu Pro Gly Lys Ile Ser
            115                 120                 125

Gln Tyr Thr
        130

<210> SEQ ID NO 82
<211> LENGTH: 142
<212> TYPE: PRT
<213> ORGANISM: artificial
<220> FEATURE:
<223> OTHER INFORMATION: PYC15D-TAT peptide (the retroinverted form of
      PYC15 peptide comprising an N-terminal tat basic region protein
      transduction domain wherein all amino acids other than glycine are
      D-amino acids)

<400> SEQUENCE: 82

Tyr Arg Tyr Arg His Met Leu Gln Tyr Trp Thr Leu Ser Cys Pro Arg
1               5                   10                  15

Arg Arg Cys Pro Lys Asp Asp Ile Leu Leu Val Ile Arg Phe Lys Leu
                20                  25                  30

Leu Arg His Phe Phe Ser Leu Ile His Trp Phe Pro Lys Ala Met Pro
            35                  40                  45

Phe Asn Phe Ile Leu Val Asp Lys Asn Glu Leu Gly Cys Leu Phe Thr
    50                  55                  60

Ser Leu Lys Val Ser Ser Ile Ile Arg Gln Val Val Gly Gly Trp Leu
65                  70                  75                  80

Pro Ile Asn Val Val Ser Ile Asn Glu Tyr Asp Ser Ala Ile Asp Leu
                85                  90                  95

Ala Asp Lys Arg Ala Lys Phe Gly Ala Asp Arg Arg Ser Phe Asn Leu
                100                 105                 110

Asp Asn Leu Phe Tyr Met Lys Val Lys Asn Glu Pro Gly Lys Ile Ser
            115                 120                 125

Gln Tyr Thr Gly Arg Arg Gln Arg Arg Lys Lys Arg Gly
        130                 135                 140

<210> SEQ ID NO 83
<211> LENGTH: 7
<212> TYPE: PRT
```

```
<213> ORGANISM: artificial
<220> FEATURE:
<223> OTHER INFORMATION: PYC18D peptide (the retroinverted form of PYC18
      peptide all amino acids other than glycine are D-amino acids)

<400> SEQUENCE: 83

His Ile Ile Ser Gln Tyr Ala
1               5

<210> SEQ ID NO 84
<211> LENGTH: 18
<212> TYPE: PRT
<213> ORGANISM: artificial
<220> FEATURE:
<223> OTHER INFORMATION: PYC18D-TAT peptide (the retroinverted form of
      PYC18 peptide comprising an N-terminal tat basic region protein
      transduction domain wherein all amino acids other than glycine are
      D-amino acids)

<400> SEQUENCE: 84

His Ile Ile Ser Gln Tyr Ala Gly Arg Arg Arg Gln Arg Arg Lys Lys
1               5                   10                  15

Arg Gly

<210> SEQ ID NO 85
<211> LENGTH: 12
<212> TYPE: PRT
<213> ORGANISM: artificial
<220> FEATURE:
<223> OTHER INFORMATION: PYC19D peptide (the retroinverted form of PYC19
      peptide all amino acids other than glycine are D-amino acids)

<400> SEQUENCE: 85

Tyr Ile Tyr Pro Tyr Ala Tyr Ser Gln Asn Ile Leu
1               5                   10

<210> SEQ ID NO 86
<211> LENGTH: 23
<212> TYPE: PRT
<213> ORGANISM: artificial
<220> FEATURE:
<223> OTHER INFORMATION: PYC19D-TAT peptide (the retroinverted form of
      PYC19 peptide comprising an N-terminal tat basic region protein
      transduction domain wherein all amino acids other than glycine are
      D-amino acids)

<400> SEQUENCE: 86

Tyr Ile Tyr Pro Tyr Ala Tyr Ser Gln Asn Ile Leu Gly Arg Arg Arg
1               5                   10                  15

Gln Arg Arg Lys Lys Arg Gly
            20

<210> SEQ ID NO 87
<211> LENGTH: 19
<212> TYPE: PRT
<213> ORGANISM: artificial
<220> FEATURE:
<223> OTHER INFORMATION: PYC20D peptide (the retroinverted form of PYC20
      peptide all amino acids other than glycine are D-amino acids)

<400> SEQUENCE: 87

Pro Thr Ile Val Leu Leu Val Cys Trp Lys Thr Gly Trp Leu Ile Ser
1               5                   10                  15

Ser Tyr Ile

<210> SEQ ID NO 88
```

```
<211> LENGTH: 30
<212> TYPE: PRT
<213> ORGANISM: artificial
<220> FEATURE:
<223> OTHER INFORMATION: PYC20D-TAT peptide (the retroinverted form of
      PYC20 peptide comprising an N-terminal tat basic region protein
      transduction domain wherein all amino acids other than glycine are
      D-amino acids)

<400> SEQUENCE: 88

Pro Thr Ile Val Leu Leu Val Cys Trp Lys Thr Gly Trp Leu Ile Ser
1               5                   10                  15

Ser Tyr Ile Gly Arg Arg Arg Gln Arg Arg Lys Lys Arg Gly
            20                  25                  30

<210> SEQ ID NO 89
<211> LENGTH: 24
<212> TYPE: PRT
<213> ORGANISM: artificial
<220> FEATURE:
<223> OTHER INFORMATION: PYC21D peptide (the retroinverted form of PYC21
      peptide all amino acids other than glycine are D-amino acids)

<400> SEQUENCE: 89

Arg Ile Lys Gly Met Asn Asp Phe Ile Asn Lys Ile Ser Asn Ser Ile
1               5                   10                  15

Asn Leu Phe Ile Tyr Ile Ile Ile
            20

<210> SEQ ID NO 90
<211> LENGTH: 35
<212> TYPE: PRT
<213> ORGANISM: artificial
<220> FEATURE:
<223> OTHER INFORMATION: PYC21D-TAT peptide (the retroinverted form of
      PYC21 peptide comprising an N-terminal tat basic region protein
      transduction domain wherein all amino acids other than glycine are
      D-amino acids)

<400> SEQUENCE: 90

Arg Ile Lys Gly Met Asn Asp Phe Ile Asn Lys Ile Ser Asn Ser Ile
1               5                   10                  15

Asn Leu Phe Ile Tyr Ile Ile Ile Gly Arg Arg Arg Gln Arg Arg Lys
            20                  25                  30

Lys Arg Gly
        35

<210> SEQ ID NO 91
<211> LENGTH: 41
<212> TYPE: PRT
<213> ORGANISM: artificial
<220> FEATURE:
<223> OTHER INFORMATION: PYC22D peptide (the retroinverted form of PYC22
      peptide all amino acids other than glycine are D-amino acids)

<400> SEQUENCE: 91

Asp Gly Pro Leu Asp Gly Arg Val Pro Tyr Val Ala Ala Asn Val Val
1               5                   10                  15

Glu Pro His Ser Met Leu Val Ala Glu Val Glu Gln Ser Ser Ile Asn
            20                  25                  30

Glu Gly Arg Arg Arg Ile Ser Asp Lys
        35                  40

<210> SEQ ID NO 92
<211> LENGTH: 52
```

-continued

```
<212> TYPE: PRT
<213> ORGANISM: artificial
<220> FEATURE:
<223> OTHER INFORMATION: PYC22D-TAT peptide (the retroinverted form of
      PYC22 peptide comprising an N-terminal tat basic region protein
      transduction domain wherein all amino acids other than glycine are
      D-amino acids)

<400> SEQUENCE: 92

Asp Gly Pro Leu Asp Gly Arg Val Pro Tyr Val Ala Ala Asn Val Val
1               5                   10                  15

Glu Pro His Ser Met Leu Val Ala Glu Val Glu Gln Ser Ser Ile Asn
                20                  25                  30

Glu Gly Arg Arg Arg Ile Ser Asp Lys Gly Arg Arg Arg Gln Arg Arg
            35                  40                  45

Lys Lys Arg Gly
    50

<210> SEQ ID NO 93
<211> LENGTH: 26
<212> TYPE: PRT
<213> ORGANISM: artificial
<220> FEATURE:
<223> OTHER INFORMATION: PYC24D peptide (the retroinverted form of PYC24
      peptide all amino acids other than glycine are D-amino acids)

<400> SEQUENCE: 93

Asp Cys Ser Thr Phe Ala Lys Ala Val Pro Ala Val Phe Leu Leu Glu
1               5                   10                  15

Lys Thr Ala Thr Leu Leu Ser Gln Tyr Leu
                20                  25

<210> SEQ ID NO 94
<211> LENGTH: 37
<212> TYPE: PRT
<213> ORGANISM: artificial
<220> FEATURE:
<223> OTHER INFORMATION: PYC24D-TAT peptide (the retroinverted form of
      PYC24 peptide comprising an N-terminal tat basic region protein
      transduction domain wherein all amino acids other than glycine are
      D-amino acids)

<400> SEQUENCE: 94

Asp Cys Ser Thr Phe Ala Lys Ala Val Pro Ala Val Phe Leu Leu Glu
1               5                   10                  15

Lys Thr Ala Thr Leu Leu Ser Gln Tyr Leu Gly Arg Arg Arg Gln Arg
                20                  25                  30

Arg Lys Lys Arg Gly
            35

<210> SEQ ID NO 95
<211> LENGTH: 10
<212> TYPE: PRT
<213> ORGANISM: artificial
<220> FEATURE:
<223> OTHER INFORMATION: PYC29D peptide (the retroinverted form of PYC29
      peptide all amino acids other than glycine are D-amino acids)

<400> SEQUENCE: 95

Gln Ser Leu Phe Ser Ile Ser Gln Tyr Ala
1               5                   10

<210> SEQ ID NO 96
<211> LENGTH: 21
<212> TYPE: PRT
```

```
<213> ORGANISM: artificial
<220> FEATURE:
<223> OTHER INFORMATION: PYC29D-TAT peptide (the retroinverted form of
      PYC29 peptide comprising an N-terminal tat basic region protein
      transduction domain wherein all amino acids other than glycine are
      D-amino acids)

<400> SEQUENCE: 96

Gln Ser Leu Phe Ser Ile Ser Gln Tyr Ala Gly Arg Arg Gln Arg
1               5                   10                  15

Arg Lys Lys Arg Gly
            20

<210> SEQ ID NO 97
<211> LENGTH: 41
<212> TYPE: PRT
<213> ORGANISM: artificial
<220> FEATURE:
<223> OTHER INFORMATION: PYC30D peptide (the retroinverted form of PYC30
      peptide all amino acids other than glycine are D-amino acids)

<400> SEQUENCE: 97

Asp Gly Pro Leu Asp Gly Arg Val Pro Tyr Val Ala Ala Asn Val Val
1               5                   10                  15

Glu Pro His Ser Met Leu Val Ala Glu Val Glu Gln Ser Ser Ile Asn
            20                  25                  30

Glu Gly Arg Arg Arg Ile Ser Asp Lys
        35                  40

<210> SEQ ID NO 98
<211> LENGTH: 52
<212> TYPE: PRT
<213> ORGANISM: artificial
<220> FEATURE:
<223> OTHER INFORMATION: PYC30D-TAT peptide (the retroinverted form of
      PYC30 peptide comprising an N-terminal tat basic region protein
      transduction domain wherein all amino acids other than glycine are
      D-amino acids)

<400> SEQUENCE: 98

Asp Gly Pro Leu Asp Gly Arg Val Pro Tyr Val Ala Ala Asn Val Val
1               5                   10                  15

Glu Pro His Ser Met Leu Val Ala Glu Val Glu Gln Ser Ser Ile Asn
            20                  25                  30

Glu Gly Arg Arg Arg Ile Ser Asp Lys Gly Arg Arg Arg Gln Arg Arg
        35                  40                  45

Lys Lys Arg Gly
    50

<210> SEQ ID NO 99
<211> LENGTH: 12
<212> TYPE: PRT
<213> ORGANISM: artificial
<220> FEATURE:
<223> OTHER INFORMATION: PYC32D peptide (the retroinverted form of PYC32
      peptide all amino acids other than glycine are D-amino acids)

<400> SEQUENCE: 99

Pro Asn Asn His Gly Asp Ser Ser His Pro Thr Asn
1               5                   10

<210> SEQ ID NO 100
<211> LENGTH: 23
<212> TYPE: PRT
<213> ORGANISM: artificial
```

<220> FEATURE:
<223> OTHER INFORMATION: PYC32D-TAT peptide (the retroinverted form of
      PYC32 peptide comprising an N-terminal tat basic region protein
      transduction domain wherein all amino acids other than glycine are
      D-amino acids)

<400> SEQUENCE: 100

Pro Asn Asn His Gly Asp Ser Ser His Pro Thr Asn Gly Arg Arg Arg
1               5                   10                  15

Gln Arg Arg Lys Lys Arg Gly
            20

<210> SEQ ID NO 101
<211> LENGTH: 29
<212> TYPE: PRT
<213> ORGANISM: artificial
<220> FEATURE:
<223> OTHER INFORMATION: PYC34D peptide (the retroinverted form of PYC34
      peptide all amino acids other than glycine are D-amino acids)

<400> SEQUENCE: 101

Ser Lys Thr Val His Gln Lys Leu His Leu Ser Leu Glu Gln Ser Asn
1               5                   10                  15

Glu Pro Leu Val Pro Ser Ser Asn Ile Ser Gln Tyr Ala
            20                  25

<210> SEQ ID NO 102
<211> LENGTH: 40
<212> TYPE: PRT
<213> ORGANISM: artificial
<220> FEATURE:
<223> OTHER INFORMATION: PYC34D-TAT peptide (the retroinverted form of
      PYC34 peptide comprising an N-terminal tat basic region protein
      transduction domain wherein all amino acids other than glycine are
      D-amino acids)

<400> SEQUENCE: 102

Ser Lys Thr Val His Gln Lys Leu His Leu Ser Leu Glu Gln Ser Asn
1               5                   10                  15

Glu Pro Leu Val Pro Ser Ser Asn Ile Ser Gln Tyr Ala Gly Arg Arg
            20                  25                  30

Arg Gln Arg Arg Lys Lys Arg Gly
            35                  40

<210> SEQ ID NO 103
<211> LENGTH: 18
<212> TYPE: PRT
<213> ORGANISM: artificial
<220> FEATURE:
<223> OTHER INFORMATION: PYC35D peptide (the retroinverted form of PYC35
      peptide all amino acids other than glycine are D-amino acids)

<400> SEQUENCE: 103

Arg Glu Arg Lys Ser Ser Ser Glu Ile Gly Gly Ser Arg Ile Ser Gln
1               5                   10                  15

Tyr Ala

<210> SEQ ID NO 104
<211> LENGTH: 29
<212> TYPE: PRT
<213> ORGANISM: artificial
<220> FEATURE:
<223> OTHER INFORMATION: PYC35D-TAT peptide (the retroinverted form of
      PYC35 peptide comprising an N-terminal tat basic region protein
      transduction domain wherein all amino acids other than glycine are
      D-amino acids)

<400> SEQUENCE: 104

Arg Glu Arg Lys Ser Ser Ser Glu Ile Gly Gly Ser Arg Ile Ser Gln
1               5                   10                  15

Tyr Ala Gly Arg Arg Gln Arg Arg Lys Lys Arg Gly
            20                  25

<210> SEQ ID NO 105
<211> LENGTH: 15
<212> TYPE: PRT
<213> ORGANISM: artificial
<220> FEATURE:
<223> OTHER INFORMATION: PYC36D peptide (the retroinverted form of PYC36
      peptide all amino acids other than glycine are D-amino acids)

<400> SEQUENCE: 105

Pro Lys Ile Ser Gln Tyr Gly Gln Arg Arg Gly Gln Leu Gly
1               5                   10                  15

<210> SEQ ID NO 106
<211> LENGTH: 26
<212> TYPE: PRT
<213> ORGANISM: artificial
<220> FEATURE:
<223> OTHER INFORMATION: PYC36D-TAT peptide (the retroinverted form of
      PYC36 peptide comprising an N-terminal tat basic region protein
      transduction domain wherein all amino acids other than glycine are
      D-amino acids)

<400> SEQUENCE: 106

Pro Lys Ile Ser Gln Tyr Gly Gln Arg Arg Gly Gln Leu Gly Gly
1               5                   10                  15

Arg Arg Arg Gln Arg Arg Lys Lys Arg Gly
            20                  25

<210> SEQ ID NO 107
<211> LENGTH: 25
<212> TYPE: PRT
<213> ORGANISM: artificial
<220> FEATURE:
<223> OTHER INFORMATION: PYC38D peptide (the retroinverted form of PYC38
      peptide all amino acids other than glycine are D-amino acids)

<400> SEQUENCE: 107

Arg His Ala Pro Leu Ala Arg Gly Ser Trp Arg Gly Gln Pro Gln Gln
1               5                   10                  15

Gly Pro Gln Arg Arg Gly Gln Leu Gly
            20                  25

<210> SEQ ID NO 108
<211> LENGTH: 36
<212> TYPE: PRT
<213> ORGANISM: artificial
<220> FEATURE:
<223> OTHER INFORMATION: PYC38D-TAT peptide (the retroinverted form of
      PYC38 peptide comprising an N-terminal tat basic region protein
      transduction domain wherein all amino acids other than glycine are
      D-amino acids)

<400> SEQUENCE: 108

Arg His Ala Pro Leu Ala Arg Gly Ser Trp Arg Gly Gln Pro Gln Gln
1               5                   10                  15

Gly Pro Gln Arg Arg Gly Gln Leu Gly Gly Arg Arg Arg Gln Arg Arg
            20                  25                  30

Lys Lys Arg Gly

```
<210> SEQ ID NO 109
<211> LENGTH: 25
<212> TYPE: PRT
<213> ORGANISM: artificial
<220> FEATURE:
<223> OTHER INFORMATION: PYC39D peptide (the retroinverted form of PYC39
      peptide all amino acids other than glycine are D-amino acids)

<400> SEQUENCE: 109

Arg His Ala Pro Leu Ala Arg Gly Ser Trp Arg Gly Gln Pro Gln Gln
1               5                   10                  15

Gly Pro Gln Arg Arg Gly Gln Leu Gly
            20                  25

<210> SEQ ID NO 110
<211> LENGTH: 36
<212> TYPE: PRT
<213> ORGANISM: artificial
<220> FEATURE:
<223> OTHER INFORMATION: PYC39D-TAT peptide (the retroinverted form of
      PYC39 peptide comprising an N-terminal tat basic region protein
      transduction domain wherein all amino acids other than glycine are
      D-amino acids)

<400> SEQUENCE: 110

Arg His Ala Pro Leu Ala Arg Gly Ser Trp Arg Gly Gln Pro Gln Gln
1               5                   10                  15

Gly Pro Gln Arg Arg Gly Gln Leu Gly Gly Arg Arg Gln Arg Arg
            20                  25                  30

Lys Lys Arg Gly
        35

<210> SEQ ID NO 111
<211> LENGTH: 61
<212> TYPE: PRT
<213> ORGANISM: artificial
<220> FEATURE:
<223> OTHER INFORMATION: PYC54D peptide (the retroinverted form of PYC54
      peptide all amino acids other than glycine are D-amino acids)

<400> SEQUENCE: 111

Tyr Arg Tyr Arg His Met Leu Gln Tyr Trp Thr Leu Ser Cys Pro Arg
1               5                   10                  15

Arg Arg Cys Thr Tyr Asp Ile Met Thr Glu Gln Thr Ala Glu Val Leu
            20                  25                  30

Lys Arg Ala Thr Ala Ser Val Ser Gly Val Leu Phe Thr Arg Ser Thr
        35                  40                  45

Asp Gly His Tyr Gly Ala Leu Ser Ile Ser Gln Tyr Ala
    50                  55                  60

<210> SEQ ID NO 112
<211> LENGTH: 72
<212> TYPE: PRT
<213> ORGANISM: artificial
<220> FEATURE:
<223> OTHER INFORMATION: PYC54D-TAT peptide (the retroinverted form of
      PYC54 peptide comprising an N-terminal tat basic region protein
      transduction domain wherein all amino acids other than glycine are
      D-amino acids)

<400> SEQUENCE: 112

Tyr Arg Tyr Arg His Met Leu Gln Tyr Trp Thr Leu Ser Cys Pro Arg
1               5                   10                  15
```

```
Arg Arg Cys Thr Tyr Asp Ile Met Thr Glu Gln Thr Ala Glu Val Leu
            20                  25                  30

Lys Arg Ala Thr Ala Ser Val Ser Gly Val Leu Phe Thr Arg Ser Thr
 35                  40                  45

Asp Gly His Tyr Gly Ala Leu Ser Ile Ser Gln Tyr Ala Gly Arg Arg
 50                  55                  60

Arg Gln Arg Arg Lys Lys Arg Gly
 65                  70

<210> SEQ ID NO 113
<211> LENGTH: 63
<212> TYPE: PRT
<213> ORGANISM: artificial
<220> FEATURE:
<223> OTHER INFORMATION: PYC58D peptide (the retroinverted form of PYC58
      peptide all amino acids other than glycine are D-amino acids)

<400> SEQUENCE: 113

Tyr Arg Tyr Arg His Met Leu Gln Tyr Trp Ala Leu Ser Cys Pro Arg
1               5                   10                  15

Arg Arg Cys Leu Glu His Phe Leu Pro Thr Arg Leu His Gln Asp Gly
            20                  25                  30

Ser Asp Ile Gly Val Gln Gly Arg Arg Gln Arg Gly Val Leu Phe
         35                  40                  45

Ala Val Pro Gln Gln Ala Ala Val Ala Met Ile Ser Gln Tyr Ala
     50                  55                  60

<210> SEQ ID NO 114
<211> LENGTH: 74
<212> TYPE: PRT
<213> ORGANISM: artificial
<220> FEATURE:
<223> OTHER INFORMATION: PYC58D-TAT peptide (the retroinverted form of
      PYC58 peptide comprising an N-terminal tat basic region protein
      transduction domain wherein all amino acids other than glycine are
      D-amino acids)

<400> SEQUENCE: 114

Tyr Arg Tyr Arg His Met Leu Gln Tyr Trp Ala Leu Ser Cys Pro Arg
1               5                   10                  15

Arg Arg Cys Leu Glu His Phe Leu Pro Thr Arg Leu His Gln Asp Gly
            20                  25                  30

Ser Asp Ile Gly Val Gln Gly Arg Arg Gln Arg Gly Val Leu Phe
         35                  40                  45

Ala Val Pro Gln Gln Ala Ala Val Ala Met Ile Ser Gln Tyr Ala Gly
     50                  55                  60

Arg Arg Arg Gln Arg Arg Lys Lys Arg Gly
 65                  70

<210> SEQ ID NO 115
<211> LENGTH: 13
<212> TYPE: PRT
<213> ORGANISM: artificial
<220> FEATURE:
<223> OTHER INFORMATION: PYC59D peptide (the retroinverted form of PYC59
      peptide all amino acids other than glycine are D-amino acids)

<400> SEQUENCE: 115

Val Val Leu Val Val Val Val Ser Ile Ser Gln Tyr Ala
1               5                   10
```

```
<210> SEQ ID NO 116
<211> LENGTH: 24
<212> TYPE: PRT
<213> ORGANISM: artificial
<220> FEATURE:
<223> OTHER INFORMATION: PYC59D-TAT peptide (the retroinverted form of
      PYC59 peptide comprising an N-terminal tat basic region protein
      transduction domain wherein all amino acids other than glycine are
      D-amino acids)

<400> SEQUENCE: 116

Val Val Leu Val Val Val Val Ser Ile Ser Gln Tyr Ala Gly Arg Arg
1               5                   10                  15

Arg Gln Arg Arg Lys Lys Arg Gly
            20

<210> SEQ ID NO 117
<211> LENGTH: 17
<212> TYPE: PRT
<213> ORGANISM: artificial
<220> FEATURE:
<223> OTHER INFORMATION: PYC60D peptide (the retroinverted form of PYC60
      peptide all amino acids other than glycine are D-amino acids)

<400> SEQUENCE: 117

Cys Lys Ile Phe Ile Leu Arg Gly Ala Leu Ile Lys Pro Leu Gln Asn
1               5                   10                  15

Ala

<210> SEQ ID NO 118
<211> LENGTH: 28
<212> TYPE: PRT
<213> ORGANISM: artificial
<220> FEATURE:
<223> OTHER INFORMATION: PYC60D-TAT peptide (the retroinverted form of
      PYC60 peptide comprising an N-terminal tat basic region protein
      transduction domain wherein all amino acids other than glycine are
      D-amino acids)

<400> SEQUENCE: 118

Cys Lys Ile Phe Ile Leu Arg Gly Ala Leu Ile Lys Pro Leu Gln Asn
1               5                   10                  15

Ala Gly Arg Arg Arg Gln Arg Arg Lys Lys Arg Gly
            20                  25

<210> SEQ ID NO 119
<211> LENGTH: 64
<212> TYPE: PRT
<213> ORGANISM: artificial
<220> FEATURE:
<223> OTHER INFORMATION: PYC66D peptide (the retroinverted form of PYC66
      peptide all amino acids other than glycine are D-amino acids)

<400> SEQUENCE: 119

Tyr Arg Tyr Arg His Met Leu Gln Tyr Trp Thr Leu Ser Cys Pro Arg
1               5                   10                  15

Arg Arg Cys Gln Gln Ala His Ala Thr Asn Lys Pro Ser Ile Ala Gln
            20                  25                  30

Gly Glu Leu Trp Ile Thr Gly Arg Asp Ala His Tyr Val Gly Thr Leu
        35                  40                  45

Ala Lys Ile Leu Thr Ser Lys Gly Ala Gly Ile Ile Ser Gln Tyr Ala
    50                  55                  60

<210> SEQ ID NO 120
<211> LENGTH: 75
```

```
<212> TYPE: PRT
<213> ORGANISM: artificial
<220> FEATURE:
<223> OTHER INFORMATION: PYC66D-TAT peptide (the retroinverted form of
      PYC66 peptide comprising an N-terminal tat basic region protein
      transduction domain wherein all amino acids other than glycine are
      D-amino acids)

<400> SEQUENCE: 120

Tyr Arg Tyr Arg His Met Leu Gln Tyr Trp Thr Leu Ser Cys Pro Arg
1               5                   10                  15

Arg Arg Cys Gln Gln Ala His Ala Thr Asn Lys Pro Ser Ile Ala Gln
                20                  25                  30

Gly Glu Leu Trp Ile Thr Gly Arg Asp Ala His Tyr Val Gly Thr Leu
            35                  40                  45

Ala Lys Ile Leu Thr Ser Lys Gly Ala Gly Ile Ile Ser Gln Tyr Ala
        50                  55                  60

Gly Arg Arg Gln Arg Arg Lys Lys Arg Gly
65                  70                  75

<210> SEQ ID NO 121
<211> LENGTH: 20
<212> TYPE: PRT
<213> ORGANISM: artificial
<220> FEATURE:
<223> OTHER INFORMATION: JNK inhibitory peptide IB-1

<400> SEQUENCE: 121

Asp Thr Tyr Arg Pro Lys Arg Pro Thr Thr Leu Asn Leu Phe Pro Gln
1               5                   10                  15

Val Pro Arg Ser
            20

<210> SEQ ID NO 122
<211> LENGTH: 21
<212> TYPE: PRT
<213> ORGANISM: artificial
<220> FEATURE:
<223> OTHER INFORMATION: JNK inhibitory peptide IB-2

<400> SEQUENCE: 122

Glu Glu Pro His Lys His Arg Pro Thr Thr Leu Arg Leu Thr Thr Leu
1               5                   10                  15

Gly Ala Gln Asp Ser
            20

<210> SEQ ID NO 123
<211> LENGTH: 19
<212> TYPE: PRT
<213> ORGANISM: artificial
<220> FEATURE:
<223> OTHER INFORMATION: Generic IB JNK inhibitory peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(15)
<223> OTHER INFORMATION: Xaa can be any naturally occurring amino acid
<220> FEATURE:
<221> NAME/KEY: misc_feature
<222> LOCATION: (19)..(19)
```

```
-continued

<223> OTHER INFORMATION: Xaa can be any naturally occurring amino acid

<400> SEQUENCE: 123

Xaa Arg Pro Thr Thr Leu Xaa Leu Xaa Xaa Xaa Xaa Xaa Xaa Xaa Gln
1               5                   10                  15

Asp Ser Xaa

<210> SEQ ID NO 124
<211> LENGTH: 19
<212> TYPE: PRT
<213> ORGANISM: artificial
<220> FEATURE:
<223> OTHER INFORMATION: Generic IB JNK inhibitory peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(15)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 124

Xaa Arg Pro Thr Thr Leu Xaa Leu Xaa Xaa Xaa Xaa Xaa Xaa Xaa Gln
1               5                   10                  15

Asp Thr Xaa

<210> SEQ ID NO 125
<211> LENGTH: 20
<212> TYPE: PRT
<213> ORGANISM: artificial
<220> FEATURE:
<223> OTHER INFORMATION: Retro-inverted generic IB JNK inhibitory
      peptide (wherein each amino acid other than glycine is a D amino
      acid)
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 125

Xaa Ser Asp Gln Xaa Xaa Xaa Xaa Xaa Xaa Xaa Leu Xaa Leu Thr Thr
1               5                   10                  15

Pro Arg Xaa Leu
            20

<210> SEQ ID NO 126
<211> LENGTH: 20
<212> TYPE: PRT
<213> ORGANISM: artificial
```

```
<220> FEATURE:
<223> OTHER INFORMATION: Retro-inverted generic IB JNK inhibitory
      peptide (wherein each amino acid other than glycine is a D amino
      acid)
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 126

Xaa Thr Asp Gln Xaa Xaa Xaa Xaa Xaa Xaa Xaa Leu Xaa Leu Thr Thr
1               5                   10                  15

Pro Arg Xaa Leu
            20

<210> SEQ ID NO 127
<211> LENGTH: 23
<212> TYPE: PRT
<213> ORGANISM: artificial
<220> FEATURE:
<223> OTHER INFORMATION: Retro-inverted IB-1 JNK inhibitory peptide
      (wherein each amino acid other than glycine is a D amino acid)

<400> SEQUENCE: 127

Thr Asp Gln Ser Arg Pro Val Gln Pro Phe Leu Asn Leu Thr Thr Pro
1               5                   10                  15

Arg Lys Pro Arg Tyr Thr Asp
            20

<210> SEQ ID NO 128
<211> LENGTH: 22
<212> TYPE: PRT
<213> ORGANISM: artificial
<220> FEATURE:
<223> OTHER INFORMATION: Retro-inverted IB-2 JNK inhibitory peptide
      (wherein each amino acid other than glycine is a D amino acid)

<400> SEQUENCE: 128

Ser Asp Gln Ala Gly Leu Thr Thr Leu Arg Leu Thr Thr Pro Arg His
1               5                   10                  15

Lys His Pro Glu Glu Leu
            20

<210> SEQ ID NO 129
<211> LENGTH: 11
<212> TYPE: PRT
<213> ORGANISM: artificial
<220> FEATURE:
<223> OTHER INFORMATION: TI-JIP peptide

<400> SEQUENCE: 129

Arg Pro Lys Arg Pro Thr Thr Leu Asn Leu Phe
1               5                   10

<210> SEQ ID NO 130
<211> LENGTH: 11
```

```
<212> TYPE: PRT
<213> ORGANISM: artificial
<220> FEATURE:
<223> OTHER INFORMATION: Retro-inverted TI-JIP peptide (wherein each
      amino acid other than glycine is a D amino acid)

<400> SEQUENCE: 130

Phe Leu Asn Leu Thr Thr Pro Arg Lys Pro Arg
1               5                   10

<210> SEQ ID NO 131
<211> LENGTH: 19
<212> TYPE: PRT
<213> ORGANISM: artificial
<220> FEATURE:
<223> OTHER INFORMATION: JNK inhibitory peptide

<400> SEQUENCE: 131

Arg Pro Lys Arg Pro Thr Thr Leu Asn Leu Phe Pro Gln Val Pro Arg
1               5                   10                  15

Ser Gln Asp

<210> SEQ ID NO 132
<211> LENGTH: 19
<212> TYPE: DNA
<213> ORGANISM: artificial
<220> FEATURE:
<223> OTHER INFORMATION: AP-1 decoy oligonucleotide

<400> SEQUENCE: 132
gcttgatgag tcagccgga                                                   19

<210> SEQ ID NO 133
<211> LENGTH: 33
<212> TYPE: DNA
<213> ORGANISM: artificial
<220> FEATURE:
<223> OTHER INFORMATION: Dz13 DNAzyme

<400> SEQUENCE: 133
cgggaggaag gctagctaca acgagaggcg ttg                                   33

<210> SEQ ID NO 134
<211> LENGTH: 21
<212> TYPE: DNA
<213> ORGANISM: artificial
<220> FEATURE:
<223> OTHER INFORMATION: c-Jun specific siRNA

<400> SEQUENCE: 134
cagcttcctg cctttgtaat t                                                21

<210> SEQ ID NO 135
<211> LENGTH: 19
<212> TYPE: DNA
<213> ORGANISM: artificial
<220> FEATURE:
<223> OTHER INFORMATION: JNK specific siRNA

<400> SEQUENCE: 135
cgtggattta tggtctgtg                                                   19

<210> SEQ ID NO 136
<211> LENGTH: 19
<212> TYPE: DNA
<213> ORGANISM: artificial
```

```
<220> FEATURE:
<223> OTHER INFORMATION: JNK specific siRNA

<400> SEQUENCE: 136
agaatgtcct accttctct                                                    19

<210> SEQ ID NO 137
<211> LENGTH: 10
<212> TYPE: PRT
<213> ORGANISM: artificial
<220> FEATURE:
<223> OTHER INFORMATION: HIV tat basic region protein transduction
      domain

<400> SEQUENCE: 137

Gly Arg Lys Lys Arg Arg Gln Arg Arg Arg
1               5                   10

<210> SEQ ID NO 138
<211> LENGTH: 11
<212> TYPE: PRT
<213> ORGANISM: artificial
<220> FEATURE:
<223> OTHER INFORMATION: HIV tat basic region protein transduction
      domain

<400> SEQUENCE: 138

Gly Arg Lys Lys Arg Arg Gln Arg Arg Arg Pro
1               5                   10

<210> SEQ ID NO 139
<211> LENGTH: 12
<212> TYPE: PRT
<213> ORGANISM: artificial
<220> FEATURE:
<223> OTHER INFORMATION: HIV tat basic region protein transduction
      domain

<400> SEQUENCE: 139

Gly Arg Lys Lys Arg Arg Gln Arg Arg Arg Pro Pro
1               5                   10

<210> SEQ ID NO 140
<211> LENGTH: 13
<212> TYPE: PRT
<213> ORGANISM: artificial
<220> FEATURE:
<223> OTHER INFORMATION: HIV tat basic region protein transduction
      domain

<400> SEQUENCE: 140

Gly Arg Lys Lys Arg Arg Gln Arg Arg Arg Pro Pro Gln
1               5                   10

<210> SEQ ID NO 141
<211> LENGTH: 11
<212> TYPE: PRT
<213> ORGANISM: artificial
<220> FEATURE:
<223> OTHER INFORMATION: HIV tat basic region protein transduction
      domain

<400> SEQUENCE: 141

Gly Arg Lys Lys Arg Arg Gln Arg Arg Arg Gly
1               5                   10

<210> SEQ ID NO 142
```

```
<211> LENGTH: 12
<212> TYPE: PRT
<213> ORGANISM: artificial
<220> FEATURE:
<223> OTHER INFORMATION: HIV tat basic region protein transduction
      domain

<400> SEQUENCE: 142

Gly Arg Lys Lys Arg Arg Gln Arg Arg Pro Gly
1               5                   10

<210> SEQ ID NO 143
<211> LENGTH: 13
<212> TYPE: PRT
<213> ORGANISM: artificial
<220> FEATURE:
<223> OTHER INFORMATION: HIV tat basic region protein transduction
      domain

<400> SEQUENCE: 143

Gly Arg Lys Lys Arg Arg Gln Arg Arg Pro Pro Gly
1               5                   10

<210> SEQ ID NO 144
<211> LENGTH: 14
<212> TYPE: PRT
<213> ORGANISM: artificial
<220> FEATURE:
<223> OTHER INFORMATION: retroinverted HIV tat basic region protein
      transduction domain wherein all amino acids other than glycine are
      D-amino acids

<400> SEQUENCE: 144

Gly Arg Lys Lys Arg Arg Gln Arg Arg Pro Pro Gln Gly
1               5                   10

<210> SEQ ID NO 145
<211> LENGTH: 10
<212> TYPE: PRT
<213> ORGANISM: artificial
<220> FEATURE:
<223> OTHER INFORMATION: retroinverted HIV tat basic region protein
      transduction domain wherein all amino acids other than glycine are
      D-amino acids

<400> SEQUENCE: 145

Arg Arg Arg Gln Arg Arg Lys Lys Arg Gly
1               5                   10

<210> SEQ ID NO 146
<211> LENGTH: 11
<212> TYPE: PRT
<213> ORGANISM: artificial
<220> FEATURE:
<223> OTHER INFORMATION: retroinverted HIV tat basic region protein
      transduction domain wherein all amino acids other than glycine are
      D-amino acids

<400> SEQUENCE: 146

Pro Arg Arg Arg Gln Arg Arg Lys Lys Arg Gly
1               5                   10

<210> SEQ ID NO 147
<211> LENGTH: 12
<212> TYPE: PRT
<213> ORGANISM: artificial
<220> FEATURE:
<223> OTHER INFORMATION: retroinverted HIV tat basic region protein
      transduction domain wherein all amino acids other than glycine are
```

```
        D-amino acids

<400> SEQUENCE: 147

Pro Pro Arg Arg Arg Gln Arg Arg Lys Lys Arg Gly
1               5                   10

<210> SEQ ID NO 148
<211> LENGTH: 13
<212> TYPE: PRT
<213> ORGANISM: artificial
<220> FEATURE:
<223> OTHER INFORMATION: retroinverted HIV tat basic region protein
      transduction domain wherein all amino acids other than glycine are
      D-amino acids

<400> SEQUENCE: 148

Gln Pro Pro Arg Arg Arg Gln Arg Arg Lys Lys Arg Gly
1               5                   10

<210> SEQ ID NO 149
<211> LENGTH: 11
<212> TYPE: PRT
<213> ORGANISM: artificial
<220> FEATURE:
<223> OTHER INFORMATION: retroinverted HIV tat basic region protein
      transduction domain wherein all amino acids other than glycine are
      D-amino acids

<400> SEQUENCE: 149

Gly Arg Arg Arg Gln Arg Arg Lys Lys Arg Gly
1               5                   10

<210> SEQ ID NO 150
<211> LENGTH: 12
<212> TYPE: PRT
<213> ORGANISM: artificial
<220> FEATURE:
<223> OTHER INFORMATION: retroinverted HIV tat basic region protein
      transduction domain wherein all amino acids other than glycine are
      D-amino acids

<400> SEQUENCE: 150

Gly Pro Arg Arg Arg Gln Arg Arg Lys Lys Arg Gly
1               5                   10

<210> SEQ ID NO 151
<211> LENGTH: 13
<212> TYPE: PRT
<213> ORGANISM: artificial
<220> FEATURE:
<223> OTHER INFORMATION: retroinverted HIV tat basic region protein
      transduction domain wherein all amino acids other than glycine are
      D-amino acids

<400> SEQUENCE: 151

Gly Pro Pro Arg Arg Arg Gln Arg Arg Lys Lys Arg Gly
1               5                   10

<210> SEQ ID NO 152
<211> LENGTH: 14
<212> TYPE: PRT
<213> ORGANISM: artificial
<220> FEATURE:
<223> OTHER INFORMATION: retroinverted HIV tat basic region protein
      transduction domain wherein all amino acids other than glycine are
      D-amino acids

<400> SEQUENCE: 152
```

-continued

Gly Gln Pro Pro Arg Arg Arg Gln Arg Arg Lys Lys Arg Gly
1               5                   10

<210> SEQ ID NO 153
<211> LENGTH: 27
<212> TYPE: PRT
<213> ORGANISM: artificial
<220> FEATURE:
<223> OTHER INFORMATION: signal sequence peptide 1 protein transduction
      domain

<400> SEQUENCE: 153

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
                20                  25

<210> SEQ ID NO 154
<211> LENGTH: 16
<212> TYPE: PRT
<213> ORGANISM: artificial
<220> FEATURE:
<223> OTHER INFORMATION: signal sequence peptide 2 protein transduction
      domain

<400> SEQUENCE: 154

Ala Ala Val Ala Leu Leu Pro Ala Val Leu Leu Ala Leu Leu Ala Pro
1               5                   10                  15

<210> SEQ ID NO 155
<211> LENGTH: 26
<212> TYPE: PRT
<213> ORGANISM: artificial
<220> FEATURE:
<223> OTHER INFORMATION: transportan protein transduction domain

<400> SEQUENCE: 155

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
                20                  25

<210> SEQ ID NO 156
<211> LENGTH: 18
<212> TYPE: PRT
<213> ORGANISM: artificial
<220> FEATURE:
<223> OTHER INFORMATION: amphiphilic model peptide protein transduction
      domain

<400> SEQUENCE: 156

Lys Leu Ala Leu Lys Leu Ala Leu Lys Ala Leu Lys Ala Ala Leu Lys
1               5                   10                  15

Leu Ala

<210> SEQ ID NO 157
<211> LENGTH: 9
<212> TYPE: PRT
<213> ORGANISM: artificial
<220> FEATURE:
<223> OTHER INFORMATION: polyarginine protein transduction domain

<400> SEQUENCE: 157

Arg Arg Arg Arg Arg Arg Arg Arg Arg
1               5

```
<210> SEQ ID NO 158
<211> LENGTH: 11
<212> TYPE: PRT
<213> ORGANISM: artificial
<220> FEATURE:
<223> OTHER INFORMATION: transdermal delivery peptide

<400> SEQUENCE: 158

Ala Cys Ser Ser Ser Pro Ser Lys His Cys Gly
1               5                   10

<210> SEQ ID NO 159
<211> LENGTH: 12
<212> TYPE: PRT
<213> ORGANISM: artificial
<220> FEATURE:
<223> OTHER INFORMATION: Kaposi fibroblast growth factor (FGF)
      hydrophobic peptide protein transduction domain

<400> SEQUENCE: 159

Ala Ala Val Leu Leu Pro Val Leu Leu Ala Ala Pro
1               5                   10

<210> SEQ ID NO 160
<211> LENGTH: 13
<212> TYPE: PRT
<213> ORGANISM: artificial
<220> FEATURE:
<223> OTHER INFORMATION: Kaposi fibroblast growth factor (FGF)
      hydrophobic peptide protein transduction domain

<400> SEQUENCE: 160

Gly Ala Ala Val Leu Leu Pro Val Leu Leu Ala Ala Pro
1               5                   10

<210> SEQ ID NO 161
<211> LENGTH: 12
<212> TYPE: PRT
<213> ORGANISM: artificial
<220> FEATURE:
<223> OTHER INFORMATION: retroinverted Kaposi fibroblast growth factor
      (FGF) hydrophobic peptide protein transduction domain (wherein
      each amino acid other than glycine is a D amino acid)

<400> SEQUENCE: 161

Pro Ala Ala Leu Leu Val Pro Leu Leu Val Ala Ala
1               5                   10

<210> SEQ ID NO 162
<211> LENGTH: 13
<212> TYPE: PRT
<213> ORGANISM: artificial
<220> FEATURE:
<223> OTHER INFORMATION: retroinverted Kaposi fibroblast growth factor
      (FGF) hydrophobic peptide protein transduction domain (wherein
      each amino acid other than glycine is a D amino acid)

<400> SEQUENCE: 162

Pro Ala Ala Leu Leu Val Pro Leu Leu Val Ala Ala Gly
1               5                   10

<210> SEQ ID NO 163
<211> LENGTH: 13
<212> TYPE: PRT
<213> ORGANISM: artificial
<220> FEATURE:
<223> OTHER INFORMATION: PYC 41 peptide
```

```
<400> SEQUENCE: 163

Val Ser Ile Asn Gln Glu His His Arg Leu Leu Pro Leu
1               5                   10

<210> SEQ ID NO 164
<211> LENGTH: 13
<212> TYPE: PRT
<213> ORGANISM: artificial
<220> FEATURE:
<223> OTHER INFORMATION: PYC41D peptide (wherein each amino acid other
      than glycine is a D amino acid)

<400> SEQUENCE: 164

Leu Pro Leu Leu Arg His His Glu Gln Asn Ile Ser Val
1               5                   10

<210> SEQ ID NO 165
<211> LENGTH: 24
<212> TYPE: PRT
<213> ORGANISM: artificial
<220> FEATURE:
<223> OTHER INFORMATION: PYC41D-tat peptide comprising a HIV tat basic
      region protien transduction domain (wherein each amino acid other
      than glycine is a D amino acid)

<400> SEQUENCE: 165

Leu Pro Leu Leu Arg His His Glu Gln Asn Ile Ser Val Gly Arg Arg
1               5                   10                  15

Arg Gln Arg Arg Lys Lys Arg Gly
                20
```